(12) United States Patent
Chavez et al.

(10) Patent No.: US 11,505,556 B2
(45) Date of Patent: Nov. 22, 2022

(54) HALOGENATED DERIVATIVES OF MORPHINANS AND USES THEREOF

(71) Applicant: Xalud Therapeutics, Inc., Berkeley, CA (US)

(72) Inventors: Raymond A. Chavez, Alameda, CA (US); Stephen Collins, Lake Forest, IL (US)

(73) Assignee: Xalud Therapeutics, Inc., Berkeley, CA (US)

( * ) Notice: Subject to any disclaimer, the term of this patent is extended or adjusted under 35 U.S.C. 154(b) by 0 days.

(21) Appl. No.: 16/772,108

(22) PCT Filed: Dec. 12, 2018

(86) PCT No.: PCT/US2018/065185
§ 371 (c)(1),
(2) Date: Jun. 11, 2020

(87) PCT Pub. No.: WO2019/118583
PCT Pub. Date: Jun. 20, 2019

(65) Prior Publication Data
US 2021/0087202 A1    Mar. 25, 2021

Related U.S. Application Data

(60) Provisional application No. 62/597,815, filed on Dec. 12, 2017.

(51) Int. Cl.
| | | |
|---|---|---|
| *C07D 489/00* | (2006.01) | |
| *A61K 31/485* | (2006.01) | |
| *A61P 25/02* | (2006.01) | |
| *A61P 25/04* | (2006.01) | |

(52) U.S. Cl.
CPC ............ *C07D 489/00* (2013.01); *A61P 25/02* (2018.01); *A61P 25/04* (2018.01); *C07B 2200/07* (2013.01)

(58) Field of Classification Search
CPC .. C07D 489/00; C07D 489/08; A61K 31/485; A61P 25/04; A61P 25/36
USPC ..................... 546/46, 44; 514/282
See application file for complete search history.

(56) References Cited

U.S. PATENT DOCUMENTS

| | | | | |
|---|---|---|---|---|
| 4,241,065 A | * | 12/1980 | Boswell, Jr. ......... | C07D 221/28 514/282 |
| 4,368,326 A | | 1/1983 | Rice | |
| 4,410,700 A | | 10/1983 | Rice | |
| 4,521,601 A | | 6/1985 | Rice | |
| 4,556,712 A | | 12/1985 | Rice | |
| 4,613,668 A | | 9/1986 | Rice | |
| 4,775,759 A | | 10/1988 | Rice et al. | |
| 5,008,449 A | | 4/1991 | Rice | |
| 5,668,285 A | | 9/1997 | Rice et al. | |
| 7,985,858 B2 | | 7/2011 | Grote et al. | |
| 8,067,596 B2 | | 11/2011 | Wang et al. | |

FOREIGN PATENT DOCUMENTS

| | | |
|---|---|---|
| EP | 0418591 A2 | 3/1991 |
| WO | WO 2009/059048 A2 | 5/2009 |
| WO | WO 2009/059050 A2 | 5/2009 |

OTHER PUBLICATIONS

Somogyi, G. et al.: Conversions of tosyl and mesyl derivatives of the morphine group, XXI. Acta Chimica Acad. Scient. Hungar., vol. 97, pp. 339-344, 1978.*
International Search Report and Written Opinion, dated Mar. 14, 2019, in connection with Application No. PCT/US2018/065185.
International Preliminary Report on Patentability, dated Jun. 25, 2020, in connection with Application No. PCT/US2018/065185.
Ellis et al., Systemic Administration of Propentofylline, Ibudilast, and (+)-naltrexone Each Reverses Mechanical Allodynia in a Novel Rat Model of Central Neuropathic Pain. J Pain. Apr. 2014;15(4):407-21. doi: 10.1016/j.jpain.2013.12.007. Epub Jan. 9, 2014.
Hutchinson et al., Evidence That Opioids May Have Toll-Like Receptor 4 and MD-2 Effects. Brain Behav Immun. Jan. 2010;24(1):83-95. doi: 10.1016/j.bbi.2009.08.004. Epub Aug. 11, 2009.
Hutchinson et al., Non-stereoselective Reversal of Neuropathic Pain by Naloxone and Naltrexone: Involvement of Toll-Like Receptor 4 (TLR4). Eur J Neurosci. Jul. 2008;28(1):20-9. doi: 10.1111/j.1460-9568.2008.06321.x.
Rothman et al., A brief study of the selectivity of norbinaltorphimine, (−)-cyclofoxy, and (+)-cyclofoxy among opioid receptor subtypes in vitro. Neuropeptides. Oct. 1988;12(3):181-7. doi: 10.1016/0143-4179(88)90052-2.
Extended European Search Report, dated May 11, 2022 for European Application No. EP 18889631.0.
Benyhe, S., Morphine: new aspects in the study of an ancient compound. Life Sci. 1994;55(13):969-79. doi: 10.1016/0024-3205(94)00631-8.
Simon et al., ChemInform Abstract: Morphine Alkaloids. Part 138. The First Preparation of 6[beta]-Bromocodeine and Morphine Derivatives. Kinetic vs. Thermodynamic Control. ChemInform. May 12, 1998;29(19):1. doi: 10.1002/chin.199819232.

* cited by examiner

*Primary Examiner* — Charanjit Aulakh
(74) *Attorney, Agent, or Firm* — Wolf, Greenfield & Sacks, P.C.

(57) ABSTRACT

The present invention encompasses improved morphian compositions and methods of use of the improved compositions for modulating neuropathic pain, opioid-induced glial activation, or a combination thereof beyond what is currently known in the art. The methods involve administering the compound of Formula I to a subject.

21 Claims, 43 Drawing Sheets

Figure 1
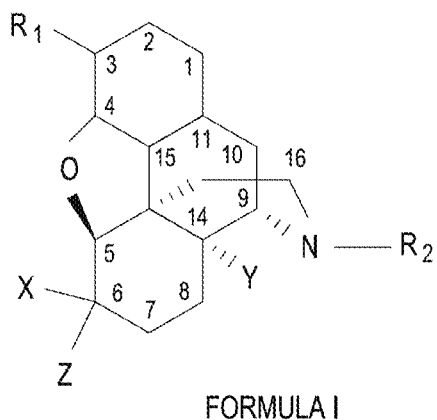
FORMULA I
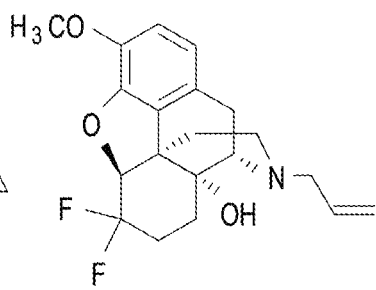
FORMULA II
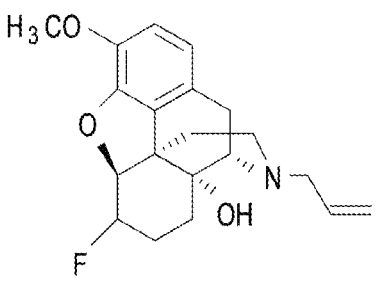
FORMULA III
FORMULA IV
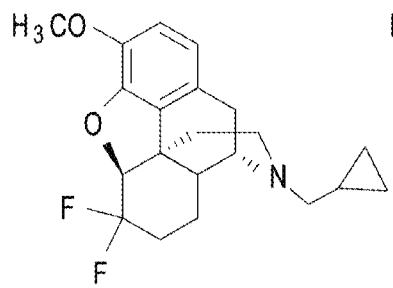
FORMULA V
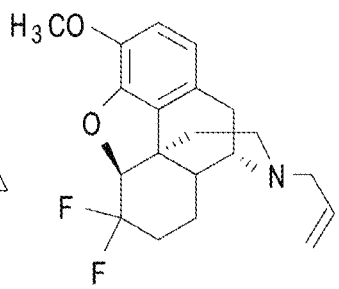
FORMULA VI
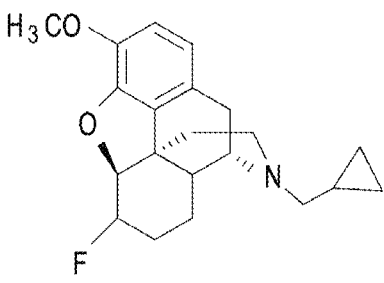
FORMULA VII ( XT-203 )
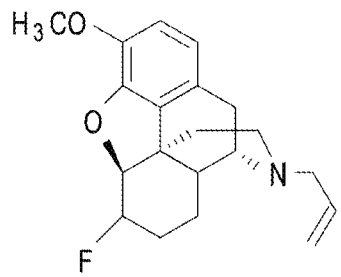
FORMULA VIII
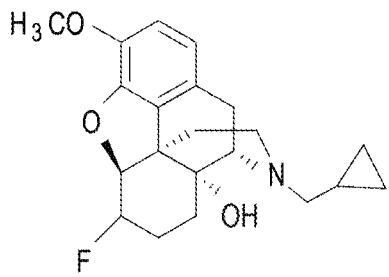
FORMULA IX
Figure 2A

FORMULA X

FORMULA XI

FORMULA XII

FORMULA XIII

FORMULA XIV

FORMULA XV

FORMULA XVI

FORMULA XVII

FORMULA XVIII

FORMULA XIX

FORMULA XX

FORMULA XXI

PE1
FORMULA XXII (XT-214)

PE2
FORMULA XXIII

PE3
FORMULA XXIV

PE4
FORMULA XXV (XT-210)

PE5
FORMULA XXVI (XT-213)

PE6
FORMULA XXVII (XT-215)

PE7
FORMULA XXVIII(XT-206)

PE8
FORMULA XXIX (XT-207)

PE9
FORMULA XXX (XT-211)

PE10
FORMULA XXXI (XT-216)

PE11
FORMULA XXXII (XT-209)

PE12
FORMULA XXXIII (XT-212)

PE13
FORMULA XXXIV (XT-208)

PE14
FORMULA XXXV (XT-217)

PE15
FORMULA XXXVI

| (+)-NTX | $t_{1/2}$ (min) |   | SE | XT-203 | $t_{1/2}$ (min) |   | SE | AK-17 | $t_{1/2}$ (min) |   | SE |
|---|---|---|---|---|---|---|---|---|---|---|---|
| RAT | 12.43 | ± | 0.53 | RAT | 13.15 | ± | 0.67 | RAT | 17.71 | ± | 0.00 |
| MONKEY | 38.89 | ± | 2.52 | MONKEY | 13.73 | ± | 1.26 | MONKEY | 19.18 | ± | 0.00 |
| DOG | 22.13 | ± | 1.09 | DOG | 24.30 | ± | 2.08 | DOG | 29.74 | ± | 0.00 |
| MOUSE | 28.80 | ± | 1.14 | MOUSE | 26.28 | ± | 1.92 | MOUSE | 20.05 | ± | 0.00 |
| HUMAN | 32.43 | ± | 1.45 | HUMAN | 54.27 | ± | 7.53 | HUMAN | 23.49 | ± | 2.47 |

Figure 9

HALOGENATED DERIVATIVES OF MORPHINANS AND USES THEREOF

RELATED APPLICATIONS

This application is a national stage filing under 35 U.S.C. § 371 of international PCT application, PCT/US2018/065185, filed Dec. 12, 2018, which claims priority under 35 U.S.C. § 119(e) to U.S. Provisional Application, U.S. Ser. No. 62/597,815, filed Dec. 12, 2017, each of which is incorporated herein by reference.

GOVERNMENT SUPPORT

This invention was made with Government support under contract W81XWH-14-C-0097 awarded by the Department of Defense. The Government has certain rights in this invention.

FIELD OF THE INVENTION

The field of the invention encompasses compositions and uses of halogenated derivatives of morphinans.

BACKGROUND OF THE INVENTION

In the following discussion, certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Conventionally, glia (astrocytes and microglia) were viewed as structural supports for neurons and important for maintaining central nervous system homeostasis. Glia were long overlooked in pain research due to their lack of axons and their yet-to-be discovered roles in cell-to-cell communication. However, a possible involvement of glia in varying pain states-including chronic and moderate to severe acute pain—has recently been investigated. Upon activation, the functions of microglia and astrocytes change in that they begin producing and releasing a variety of neuroexcitatory substances including reactive oxygen species, nitric oxide prostaglandins, excitatory amino acids, growth factors, and proinflammatory cytokines, such as IL-1, IL-6, and tumor necrosis factor. Traditional pain therapies typically have targeted transmission of the pain signal between neurons with limited success. It is therefore of interest in the art to modify traditional pain therapies and to modulate or attenuate glial activation, thereby blocking the downstream consequences of such activation. The present invention provides compositions and methods of using such compositions that address these interests.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description, including those aspects illustrated in the accompanying drawings and defined in the appended claims.

One embodiment of the present invention encompasses a compound comprising the (+)-isomers of Formula I or a pharmaceutically acceptable salt thereof:

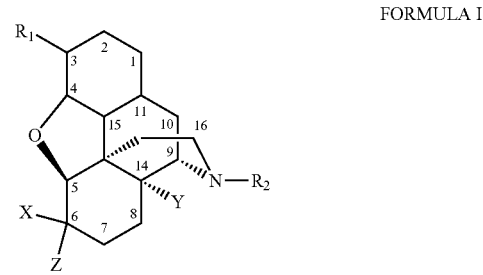

FORMULA I wherein:

$R_1$ is selected from the group consisting of hydroxyl, alkoxy, or aryloxy;

$R_2$ is selected from the group consisting of hydrogen, alkyl, alkynyl, alkenyl, alkoxy, alkylamide, alkylsulfamide, hydrocarbyl, substituted hydrocarbyl, cycloalkyl, alkylaryl, or substituted alkylaryl;

Y is selected from the group consisting of hydrogen or hydroxy;

X is selected from the group consisting of fluorine, chlorine, bromine or iodine; and Z is selected from the group consisting of hydrogen, fluorine; chlorine, bromine or iodine;

provided that when $R_1$ is hydroxyl, $R_2$ is not cyclopropylmethyl.

In certain embodiments, each bond between carbons 1 and 2, 3 and 4, 7 and 8, and 11 and 15 is selected from the group consisting of a single bond and a double bond. In certain embodiments, each bond between carbons 1 and 2, 3 and 4, and 11 and 15 is selected from the group consisting of a single bond and a double bond. In certain embodiments, Formula I further comprises an unsaturated double bond between carbons 7 and 8.

In certain aspects, the compound of Formula I is of the formula:

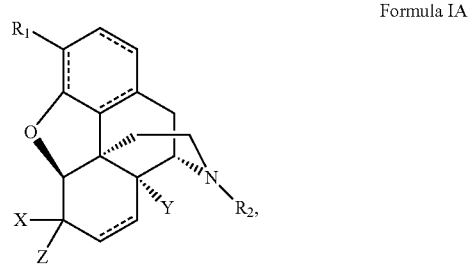

Formula IA or a pharmaceutically acceptable salt thereof.

In certain aspects, a compound of Formula I is of the formula:

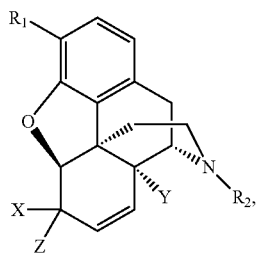

Formula IB or a pharmaceutically acceptable salt thereof.

In certain embodiments, a compound of Formula I is of the formula:

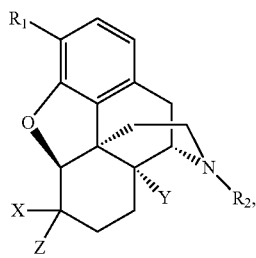

Formula IC or a pharmaceutically acceptable salt thereof.

In a certain aspects, $R_2$ is cyclopropylmethyl, propyl(2) ene, butyl, pentyl, hexyl, or phenethyl.

In yet another aspect, the compound of Formula I is one or more of Formulas II-XXXVI. In yet another aspect, the compound of Formula I is one or more of Formulas II-XXXVI or a pharmaceutically acceptable salt thereof.

An aspect of the invention is the compound Formula VII. Another aspect of the invention is the compound Formula IX. Other aspects of the invention include the compounds Formula XXII, Formula XXIII, Formula XXIV, Formula XXV, Formula XXVI, Formula XXVII, Formula XXVIII, Formula XXIX, Formula XXX, Formula XXXI, Formula XXXIII, Formula XXXIV, and Formula XXXV (shown herein in Table 1 and FIGS. 1 and 2A to 2G).

An aspect of the invention is the compound Formula VII or a pharmaceutically acceptable salt thereof. Another aspect of the invention is the compound Formula IX or a pharmaceutically acceptable salt thereof. Other aspects of the invention include the compounds Formula XXII, Formula XXIII, Formula XXIV, Formula XXV, Formula XXVI, Formula XXVII, Formula XXVIII, Formula XXIX, Formula XXX, Formula XXXI, Formula XXXIII, Formula XXXIV, and Formula XXXV (shown herein in Table 1 and FIGS. 1 and 2A to 2G), or pharmaceutically acceptable salts thereof.

In one aspect, carbons 1 and 2, 3 and 4, and 11 and 15 of Formula I have alternating double bonds to form an aromatic ring.

In yet another aspect, there is an unsaturated double bond between carbons 7 and 8 of Formula I.

One embodiment of the invention is a method for treating pain-including chronic and moderate to severe acute pain—in a subject comprising administering to the subject an effective amount of the compound of Formula I.

Other embodiments of the invention provide a method for potentiating the analgesic effects of an opioid in a subject comprising administering to the subject an effective amount of a compound of Formula I. In some aspects of this embodiment, the compound of Formula I is administered to the subject with an opioid compound; in other aspects of this embodiment, the compound of Formula I is administered to a subject after an opioid compound is administered to the subject; and in yet other aspects, the compound of Formula I is administered to a subject before an opioid compound is administered to a subject.

Another embodiment of the invention provides a method for reducing the risk of developing an opioid dependency in a subject during opioid therapy, comprising the step of administering to the subject who is on opioid therapy an effective amount of the compound of Formula I.

Yet another embodiment of the invention provides a method for treating a subject with a clinical condition associated with Toll-like receptor (TLR) glial activation comprising the step of administering to the subject an effective amount of the compound of Formula I. In some aspects of this embodiment, the Toll-like receptor (TLR) is TLR-4. Also, in some aspects of this embodiment, the clinical condition comprises acute nociceptive pain; neuropathic pain; other pain subtypes/mixed pain states, e.g., pain caused by burns, osteoarthritis, chemotherapy, trauma; acute and repetitive opioid analgesia; the reward effects of drug abuse, chronic pain, or other pain associated with opioid dependency. The details of certain embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE FIGURES

FIG. 1 shows Formula I.

FIGS. 2A to 2G show a number of exemplary species of Formula I.

FIG. 9 shows the results of a study in various species including a rat, monkey, dog, mouse, and human to determine the half-life of (+)-NTX, AK17, and XT-203 in these species.

DETAILED DESCRIPTION OF THE INVENTION

Figure 2B:
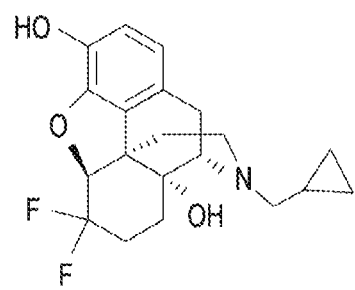
Figure 2B:
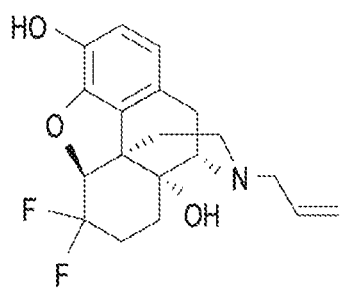
Figure 2B:
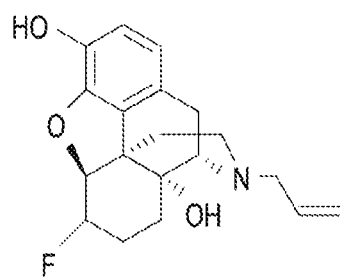
Figure 2B:
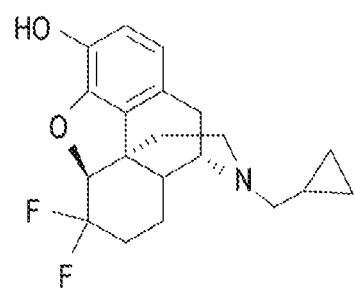
Figure 2B:
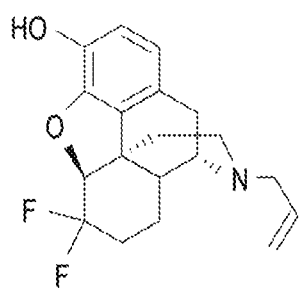
Figure 2B:
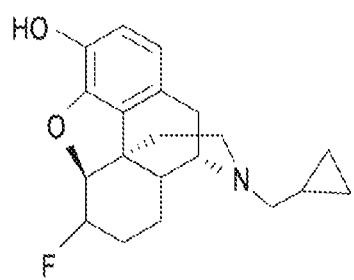
Figure 2B:
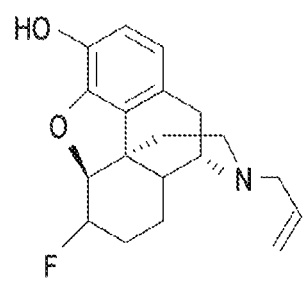
Figure 2C:
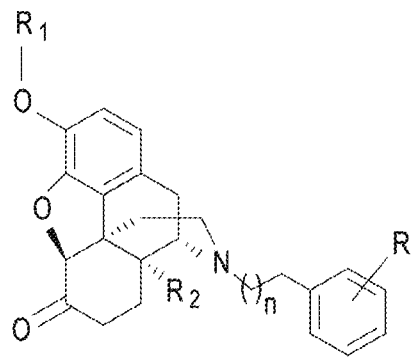
Figure 2C:
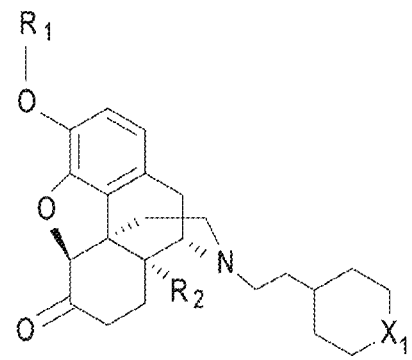
Figure 2C:
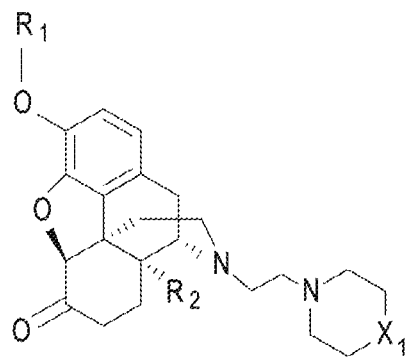
Figure 2C:
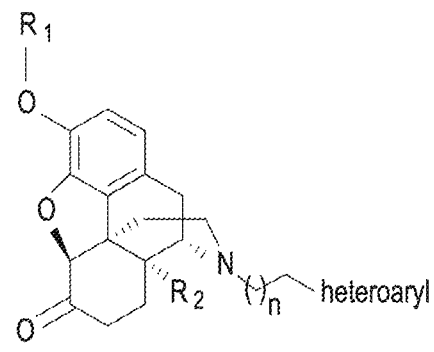
Figure 2C:
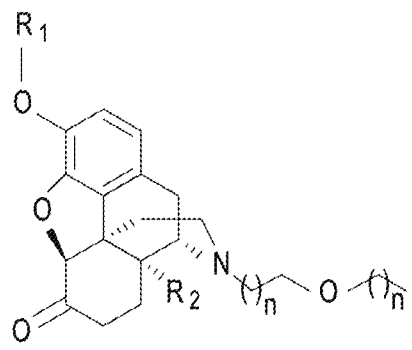
Figure 2D:
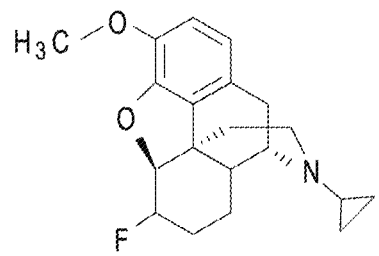
Figure 2D:
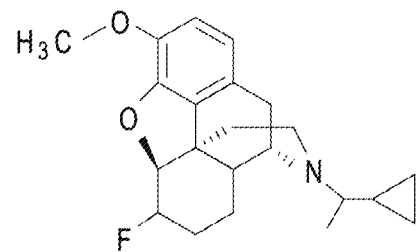
Figure 2D:
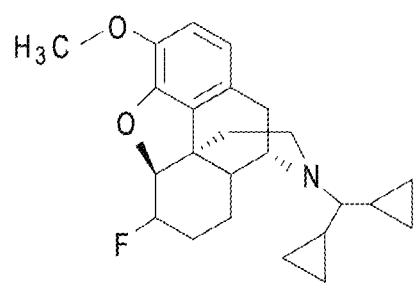
Figure 2D:
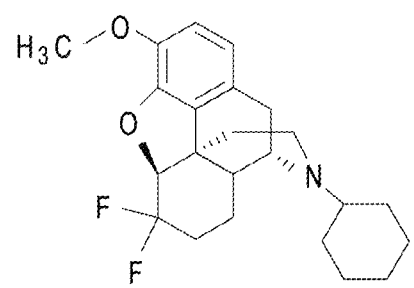
Figure 2D:
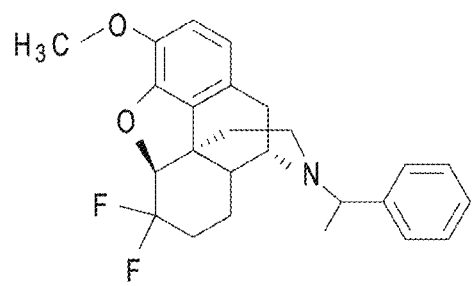
Figure 2D:
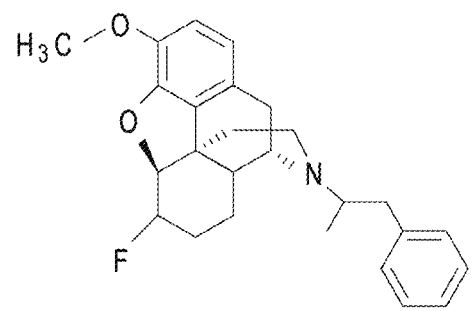
Figure 2E:
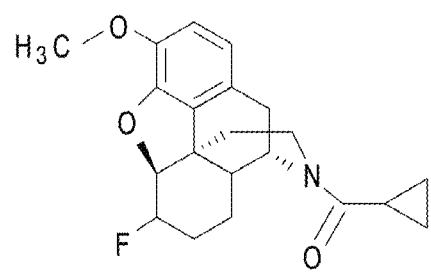
Figure 2E:
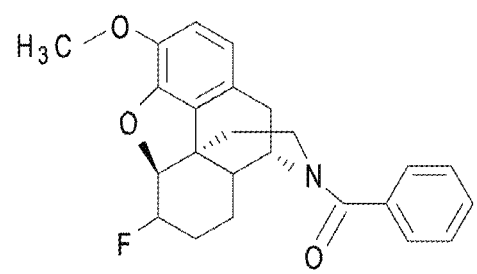
Figure 2E:
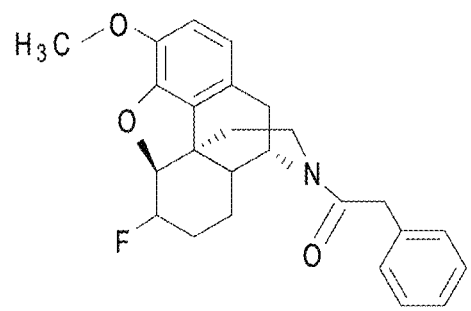
Figure 2E:
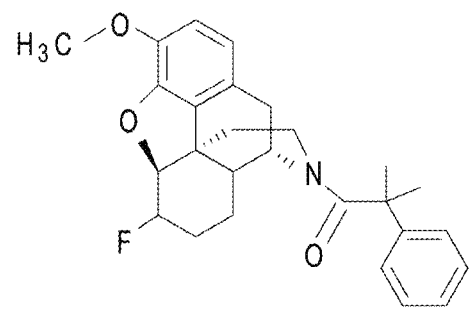
Figure 2F:
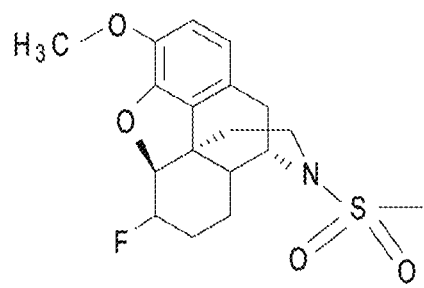
Figure 2F:
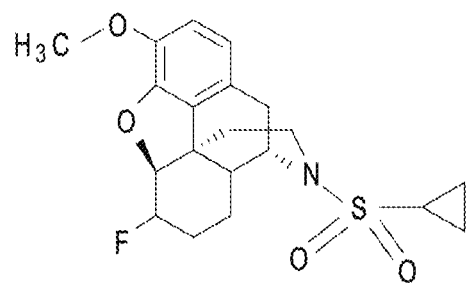
Figure 2F:
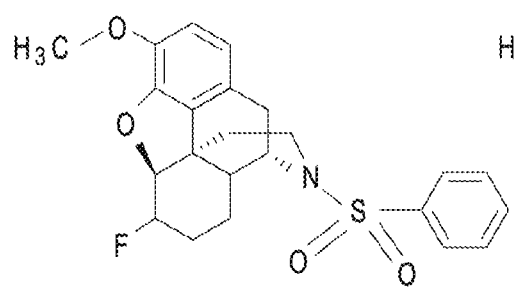
Figure 2F:
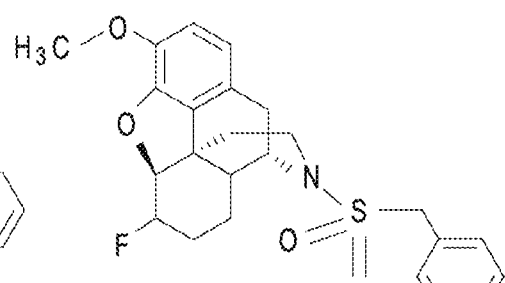
Figure 2G:
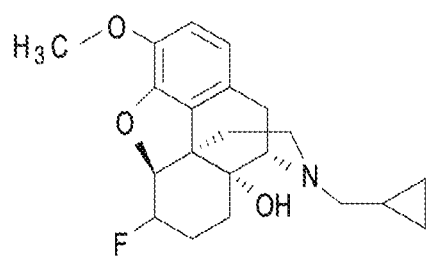

The methods described herein may employ, unless otherwise indicated, conventional techniques and descriptions of organic chemistry/small molecule synthesis and various methodologies for the treatment of pain and opioid tolerance, all of which are within the skill of those who practice in the art. Specific illustrations of suitable techniques can be had by reference to the examples herein. However, equivalent conventional procedures can, of course, also be used. Such conventional techniques and descriptions can be found in standard laboratory manuals such as Carey and Sundberg, *Advanced Organic Chemistry* (2005), Springer; Nicolaou and Sorenson, Classics in Total Synthesis I and II (1996, 2003), Wiley-VCH; Mahrwald, *Enantioselective Organocatalyzed Reactions* (2011), Springer; Harwood, Moody and Percy, *Experimental Organic Chemistry—Standard and Microscale* (1999), Blackwell; Zweifel and Nantz, *Modern Organic Synthesis* (2007), WH Freeman; Hoppenfeld, *Fundamentals of Pain Medicine: How to Diagnose and Treat your Patients* (2014), Lippincott Williams & Williams; Kim, *Pain Medicine Pocketpedia* (2012), Lippincott Williams & Williams; all of which are herein incorporated by reference in their entirety for all purposes. Before the present compositions, research tools and methods are described, it is to be understood that this invention is not limited to the specific methods, compositions, targets, and uses described, as such may, of course, vary. It is also to be understood that the terminology used herein is for the purpose of describing particular aspects only and is not intended to limit the scope of the present invention, which will be limited only by the appended claims.

Note that as used in the present specification and in the appended claims, the singular forms "a," "an," and "the" include plural referents unless the context clearly dictates otherwise. Thus, for example, reference to "a composition" refers to one composition, more than one composition, or mixtures of compositions, and reference to "an assay" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing formulations and methodologies that are described in the publication and that might be used in connection with the presently described invention.

Where a range of values is provided, it is understood that each intervening value between the upper and lower limit of that range and any other stated or intervening value in that stated range is encompassed within the invention. The upper and lower limits of these smaller ranges may independently be included in smaller ranges which are also encompassed within the invention, subject to any specifically excluded limit in the stated range. Where the stated range includes both of the limits, ranges excluding either of those included limits are also included in the invention.

In the following description, numerous specific details are set forth to provide a more thorough understanding of the present invention. However, it will be apparent to one of skill in the art upon reading the specification that the present invention may be practiced without one or more of these specific details. In other instances, well-known features and procedures well known to those skilled in the art have not been described in order to avoid obscuring the invention.

Definitions

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The disclosure additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn). In some embodiments, "alkyl" refers to a saturated linear monovalent hydrocarbon moiety of one to twelve, preferably one to six, carbon atoms or a saturated branched monovalent hydrocarbon moiety of three to twelve, preferably three to six, carbon atoms. Exemplary alkyl groups include, but are not limited to, methyl, ethyl, n-propyl, 2-propyl, tert-butyl, pentyl, and the like. "Alkylaryl" refers to a moiety of the formula —$R_1$—$R_2$, where $R_1$ is an alkyl group and $R_2$ is an aryl group. The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C), and the like. Additional examples of alkenyl include heptenyl (C$_7$), octenyl (C$_8$), octatrienyl (C), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$ or ) may be an (E)- or (Z)-double bond. In some embodiments, "alkenyl" refers to a linear monovalent hydrocarbon moiety of two to ten carbon atoms or a branched monovalent hydrocarbon moiety of three to ten carbon atoms, containing at least one double bond, e.g., ethenyl, propenyl, and the like.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

"Alkoxy" refers to a moiety of the formula —OR″, wherein R″ is an alkyl group as defined herein.

"Alkylamide" as used herein refers to a compound with the functional group RONR'$_2$, where R and R' are H or organic groups. "Alkylsulfamide" refers to a compound with the functional group RHNSO$_2$NH$_2$, where R is an organic group.

"Antagonist" refers to a compound or a composition that attenuates the effect of an agonist. The antagonist can bind reversibly or irreversibly to a region of the receptor in common with an agonist. An antagonist can also bind at a different site on the receptor. The term "antagonist" also includes a functional or physiological antagonist. A "functional antagonist" refers to a situation in which two agonists interact with different receptors and produce opposing effects. A "physiological agonist" describes the behavior of a substance that produces effects counteracting those of another substance using a mechanism that does not involve binding to the same receptor.

The term "aryl" refers to a radical of a monocyclic or polycyclic (e.g., bicyclic or tricyclic) 4n+2 aromatic ring system (e.g., having 6, 10, or 14 T electrons shared in a cyclic array) having 6-14 ring carbon atoms and zero heteroatoms provided in the aromatic ring system ("C$_{6-14}$ aryl"). In some embodiments, an aryl group has 6 ring carbon atoms ("C$_6$ aryl"; e.g., phenyl). In some embodiments, an aryl group has 10 ring carbon atoms ("C$_{10}$ aryl"; e.g., naphthyl such as 1-naphthyl and 2-naphthyl). In some embodiments, an aryl group has 14 ring carbon atoms ("C$_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted C$_{6-14}$ aryl. In certain embodiments, the aryl group is a substituted C$_{6-14}$ aryl. In some embodiments, "aryl" refers to a monovalent mono-, bi- or tricyclic aromatic hydrocarbon moiety of 6 to 15 ring atoms that is optionally substituted with one or more, preferably one, two, or three substituents within the ring structure. When two or more substituents are present in an aryl group, each substituent is independently selected.

"Aryloxy" refers to a moiety of the formula —OAr$^1$, wherein Ar$^1$ is aryl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{1-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C), cyclohexenyl (C), cyclohexadienyl (C), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" or "cycloalky" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{1-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl. In some embodiments, "cycloalkyl" refers to a non-aromatic, preferably saturated, monovalent mono- or bicyclic hydrocarbon moiety of three to ten ring carbons. The cycloalkyl can be optionally substituted with one or more, preferably one, two, or three substituents within the ring structure. When two or more substituents are present in a cycloalkyl group, each substituent is independently selected.

The term "derivative or an analog thereof" refers to those compounds that are derived from or have a similar core structure and retain all of the biological activity of the compound to which they are referred to.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

The terms "halo," "halogen" and "halide" are used interchangeably herein and refer to fluoro-, chloro-, bromo-, or iodo-groups.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Hydrocarbyl" refers to any univalent radical derived from a hydrocarbon.

"Hydroxy" refers to an —OH group. "Deshydroxy" refers to a lack of a hydroxy group at a position that typically has a hydroxyl group.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March Advanced Organic Chemistry 6th ed. (501-502). Exemplary leaving groups include, but are not limited to, halo (e.g., chloro, bromo, iodo), —OR$^{aa}$ (when the O atom is attached to a carbonyl group, wherein R$^{aa}$ is as defined herein), —O(C=O)R$^{LG}$, alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, or —O(SO)$_2$R$^{LG}$ (e.g., tosyl, mesyl, besyl), wherein R$^{LG}$ is optionally substituted alkyl, optionally substituted aryl, or optionally substituted heteroaryl. In some cases, the leaving group is a halogen. In some embodiments, the leaving group is I. In some embodiments, "leaving group" has the meaning conventionally used in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Neuropathic pain" refers to pain caused by damage or disease affecting the somatosensory nervous system (i.e., refers to pain resulting from injury to a nerve). Non-limiting examples of neuropathic pain include pain associated with or derived from spinal cord injury, multiple sclerosis, stroke, diabetes (e.g., peripheral diabetic neuropathy), sciatica, herpes zoster infection, HIV, neuralgia (e.g., post-herpetic neuralgia, trigeminal neuralgia), nutritional deficiencies, toxins, tumors, immune mediated disorders, physical trauma to a nerve trunk, cancer, chemotherapy (e.g., chemotherapy-induced pain such as chemotherapy-induced peripheral neuropathy), radiation injury, invasive medical procedures, surgery, non-specific lower back pain, carpal tunnel syndrome, fibroryalgia, and pain resulting from an inflammatory condition (e.g., a chronic inflammatory condition). Neuropathic pain typically is long-lasting or chronic and often develops days or months. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Neuropathic pain conditions can develop following neuronal injury and the resulting pain may persist for months or years. Neuronal injury may occur in the peripheral nerves, dorsal roots, spinal cord or certain regions in the brain. Neuropathic pain can result from a peripheral nerve disorder such as neuroma; nerve compression; nerve crush, nerve stretch or incomplete nerve transsection; mononeuropathy or polyneuropathy. Neuropathic pain can also result from a disorder such as dorsal root ganglion compression; inflammation of the spinal cord; contusion, tumor or hemisection of the spinal cord; tumors of the brainstem, thalamus or cortex; or trauma to the brainstem, thalamus or cortex.

"Nociceptive pain" refers to pain caused by stimuli being detected by nociceptors in the body (i.e., pain caused by acute tissue injury involving small cutaneous nerves or small nerves in muscle or connective tissue). Nociceptors are primarily found in the skin, joints, and walls of organs. Non-limiting examples of nociceptive pain include pain associated with or derived from bruises, burns, fractures, overuse or joint damage (e.g., arthritis, sprains), radiculopathy, pinched nerve, tumor, headache, laceration, surgery, and cancer.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

"Opioid" or "opioid compound" are used interchangeably and refer to a substance that binds to a opioid receptor. Opioid receptors are principally found in the central and peripheral nervous system and the gastrointestinal tract. Opioid receptors are distributed widely in the brain, in the spinal cord, on peripheral neurons, and digestive tract. In some embodiments, the opioid receptor is a μ-, δ-, or κ-opioid receptor. In certain embodiments, the opioid receptor is a μ-opioid receptor.

"Pharmaceutically acceptable excipient" refers to an excipient that is useful in preparing a pharmaceutical composition that is generally safe, non-toxic, and may include excipient that is acceptable for veterinary use as well as human pharmaceutical use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. In certain embodiments, "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion, or coordinates with an organic base such as ethanolamine, diethanolamine, triethanolamine, tromethamine, N-methylglucamine, and the like.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred. The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, and the like.

"Protecting group" refers to a moiety, except alkyl groups, that when attached to a reactive group in a molecule masks, reduces or prevents that reactivity. Examples of protecting groups can be found in Greene and Wuts, *Protective Groups in Organic Synthesis*, 3rd edition, John Wiley & Sons, New York (1999), and Harrison and Harrison et al., *Compendium of Synthetic Organic Methods*, Vols. 1-8, John Wiley and Sons (1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. A "corresponding protecting group" means an appropriate protecting group corresponding to the heteroatom (i.e., N, O, P or S) to which it is attached.

The terms "subject", "individual" or "patient"" may be used interchangeably herein and refer to a mammal, and in some embodiments, a human. A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal "Disease," "disorder," and "condition" are used interchangeably herein.

The term "administer," "administering," or "administration" refers to implanting, absorbing, ingesting, injecting, inhaling, or otherwise introducing a compound described herein, or a composition thereof, in or on a subject.

A "therapeutically effective amount" means the amount of a compound that, when administered to a mammal for treating a disease, is sufficient to effect such treatment for the disease. The "therapeutically effective amount" will vary depending on the compound, the disease and its severity, and the age, weight, etc., of the mammal to be treated.

As used herein, and unless otherwise specified, the terms "treat," "treating" and "treatment" contemplate an action that occurs while a subject is suffering from the specified disease or condition, which reduces the severity of the disease or condition, or retards or slows the progression of the disease or condition (i.e., "therapeutic treatment"), and also contemplates an action that occurs before a subject begins to suffer from the specified disease or condition (i.e., "prophylactic treatment"). "Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms. When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction that produces the indicated and/or the desired product may not necessarily result directly from the combination of two reagents which were initially added, i.e., there may be one or more intermediates which are produced in the mixture which ultimately leads to the formation of the indicated and/or the desired product.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted"

alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any one of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. The disclosure is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_1$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_1$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^d$d substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3{}^+$X$^-$, —NH(C$_{1-6}$ alkyl)$_2{}^+$X$^-$, —NH$_2$(C$_{1-6}$ alkyl)$^+$X$^-$, —NH$_3{}^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

The term "amino" refers to the group —NH$_2$. The term "substituted amino," by extension, refers to a monosubstituted amino, a disubstituted amino, or a trisubstituted amino. In certain embodiments, the "substituted amino" is a mono-substituted amino or a disubstituted amino group.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{aa}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$ alkynyl, $C_{3-10}$ carbocyclyl, 3-14 membered heterocyclyl, $C_{6-14}$ aryl, and 5-14 membered heteroaryl, or two RC groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is a nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3- dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide(Mtr), 2,4,6-trimethoxybenzenesulfonamide(Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3^+$X$^-$, —P(OR$^{cc}$)$_2$, —P(OR$^{cc}$)$_3^+$X$^-$, —P(=O) (R$^{aa}$)$_2$, —P(=O)(OR$^{cc}$)$_2$, and —P(=O)(N(R$^{bb}$) 2)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl(MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and Claims. The invention is not intended to be limited in any manner by the above exemplary listing of substituents.

As used herein, the term "salt" refers to any and all salts, and encompasses pharmaceutically acceptable salts.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

These and other aspects and uses of the invention will be described in the detailed description.

The present invention encompasses compositions and uses of halogenated derivatives of morphinans; specifically, the (+)-isomers of Formula I or a pharmaceutically acceptable salt thereof:

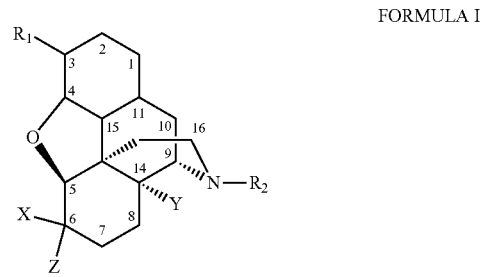

FORMULA I wherein:
R$_1$ is selected from the group consisting of hydroxyl, alkoxy, or aryloxy;
R$_2$ is selected from the group consisting of hydrogen, alkyl, alkynyl, alkenyl, alkoxy, alkylamide, alkylsulfamide, hydrocarbyl, substituted hydrocarbyl, cycloalkyl, alkylaryl, or substituted alkylaryl;
Y is selected from the group consisting of hydrogen or hydroxy;
X is selected from the group consisting of fluorine, chlorine, bromine or iodine; and
Z is selected from the group consisting of hydrogen, fluorine, chlorine, bromine or iodine;
provided that when R$_1$ is hydroxyl, R$_2$ is not cyclopropylmethyl.

In some aspects, in Formula I each bond between carbons 1 and 2, 3 and 4, 7 and 8, and 11 and 15 is selected from the group consisting of a single bond and a double bond In some aspects, Formula I also includes an unsaturated double bond between carbons 7 and 8 of Formula I. In some aspects, Formula I also includes an unsaturated double bond between carbons 1 and 2, 3 and 4, and 11 and 5 of Formula I to form an aromatic ring.

Due to the ability of neurons to transmit pain, neurons have been the primary intentional target of the majority of pharmacotherapies to treat pain developed to date. Generally, it was believed that opioids modulate pain solely by acting at neuronal opioid receptors, and that opioid antagonists likewise exert their effects solely on neurons. Furthermore, it was conventionally believed that the detrimental (e.g., tolerance, hyperalgesia, dependence, and reward, etc.) and beneficial (e.g., analgesia, cough suppressant, etc.) actions of opioids are mediated via very similar and potentially inseparable mechanisms, reliant on neuronal opioid receptors. In contrast, however, it has been shown that immunocompetent cells of the central nervous system, glia, their receptors, and their secreted signaling factors are involved in pain processing and opioid pharmacodynamics. In particular, glia have been shown to have a role in initiating and maintaining increased pain in response to peripheral nerve injury. Recently, it has been suggested that glia can also modulate the analgesic actions of chronically administered opioids. Accordingly, aspects of the invention provide pharmacological targeting (e.g., modulation) of glia to modulate (e.g., reduce or eliminate) pain and enhance efficacy of opioids.

It has also been shown that opioids cause direct glial activation in a non-classical opioid receptor fashion, via opioid-induced activation of a class of pattern recognition receptors termed Toll-like Receptors (TLRs). (See, e.g., Hutchinson, et al., Eur. J. Neurosci., 28(1):20-29 (2008); Hutchinson, et al., Brain, Behavior, and Immunity, 24:83-95 (2009); Ellis, et al., J. Pain, 15(4):407-21 (2014); and Watkins and Hutchinson WO2009/059050). TLRs are significant mediators of neuropathic pain, opioid tolerance, opioid dependence, and opioid reward. Thus, in some instances antagonizing TLRs reverses neuropathic pain, and potentiates opioid and non-opioid analgesia. Accordingly, some aspects of the invention relate to attenuating glial activation by antagonizing or blocking TLRs (e.g., TLR2, TLR4, other TLRs) that can bind to either opioid analgesics, non-opioid analgesics, or endogenous danger signals known to be TLR agonists, or a combination thereof, or generally reducing glial activation. That is, reduction of glial activation reduces exaggerated pain states, enhances opioid analgesia, and reduces the development of opioid tolerance, dependence and reward.

However, opioid compounds currently known in the art have pharmacokinetic issues; that is, it is of interest in the art to slow the metabolic breakdown of these compounds and to improve bioavailability. The opioid compounds of the present invention—that is, the compounds of Formula I—address the pharmacokinetic issues in two ways. First, in all compounds of Formula I at least one halogen molecule (e.g., fluorine) is positioned at C6 of the compound of Formula I (see FIG. 1, Table 1). Second, in certain embodiments, the compound of Formula I employs longer or more sterically-hindering N-derivative chains positioned at C9 (e.g., see FIG. 1 and FIGS. 2A to 2G, particularly Formulas XVI-XX, Table 1). Accordingly, aspects of the invention provide methods for improving bioavailability for modulating neuropathic pain, opioid-induced glial activation, or a combination thereof beyond what is currently known in the art by administering the compound of Formula I to a subject.

TABLE 1

Exemplary Formula and Compounds

| Formula | Name | Structure |
|---|---|---|
| IA | | 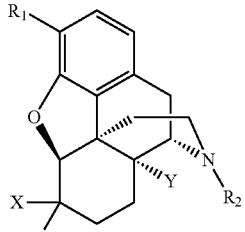 |
| IB | | 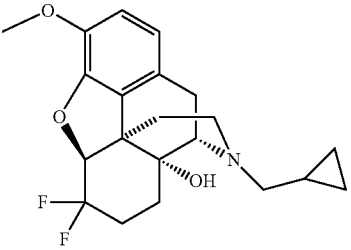 [SMILES: COc1ccc2c3c1O[C@@H]1C(F)(F)CC[C@]4(O)[C@H](C2)N(CC2CC2)CC[C@@]314] |

TABLE 1-continued

Exemplary Formula and Compounds

| Formula | Name | Structure |
|---|---|---|
| IC | | 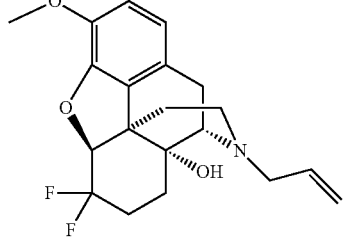 |
| II | | 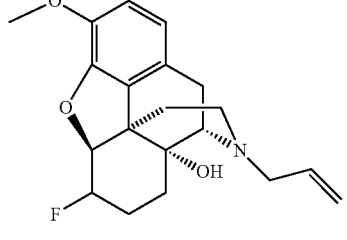 |
| III | | 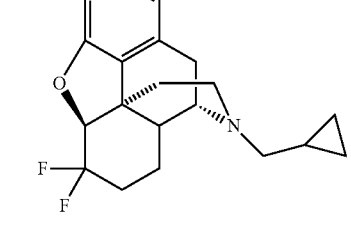 |
| IV | | 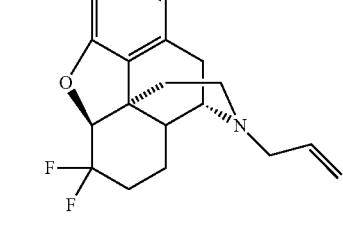 |
| V | | 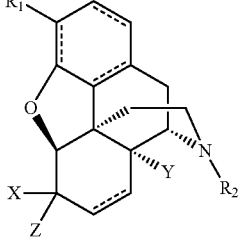 |
| VI | | 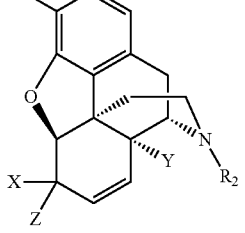 |

TABLE 1-continued
Exemplary Formula and Compounds
| Formula | Name | Structure |
|---|---|---|
| VII | XT-203 | 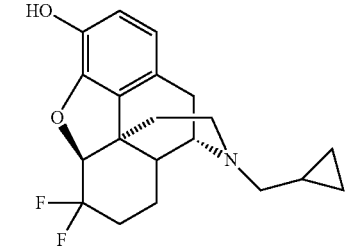 |
| VIII | | 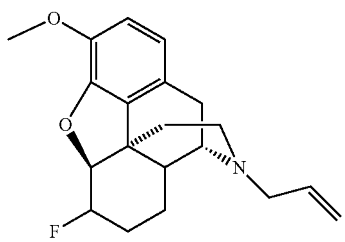 [SMILES: C=CCN1CC[C@@]23c4c5ccc(OC)c4O[C@@H]2C(F)CCC3[C@@H]1C5] |
| IX | | 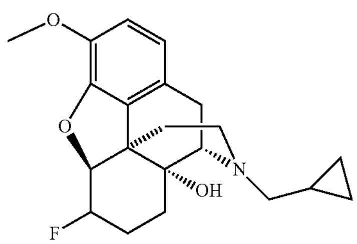 [SMILES: COc1ccc2c3c1O[C@@H]1C(F)CC[C@]4(O)[C@H](C2)N(CC2CC2)CC[C@@]314] |
| X | | 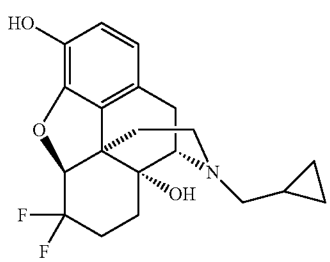 [SMILES: Oc1ccc2c3c1O[C@@H]1C(F)(F)CC[C@]4(O)[C@H](C2)N(CC2CC2)CC[C@@]314] |
| XI | | 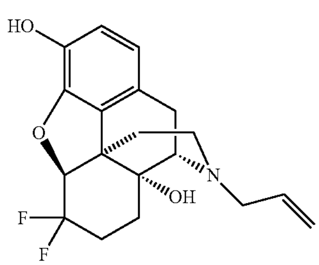 [SMILES: C=CCN1CC[C@@]23c4c5ccc(O)c4O[C@@H]2C(F)(F)CC[C@]3(O)[C@@H]1C5] |
| XII | | 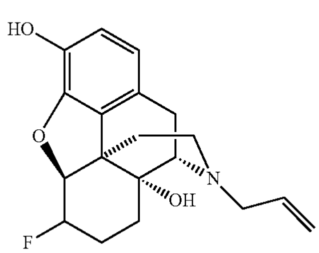 [SMILES: C=CCN1CC[C@@]23c4c5ccc(O)c4O[C@@H]2C(F)CC[C@]3(O)[C@@H]1C5] |
| XIII | | 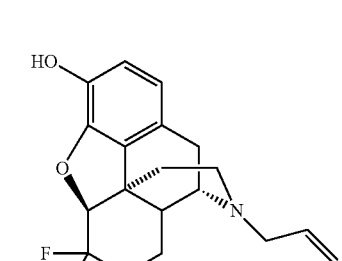 |
| XIV | | |
| XV | | |
| XVI | | |
| XVII | | |

TABLE 1-continued

Exemplary Formula and Compounds

| Formula | Name | Structure |
|---|---|---|
| XVIII | | (structure) |
| XIX | | (structure) |
| XX | | (structure) |
| XXI | | (structure) |
| XXII | XT-214 | (structure) |
| XXIII | | (structure) |
| XXIV | | (structure) |
| XXV | XT-210 | (structure) |
| XXVI | XT-213 | (structure) |
| XXVII | XT-215 | (structure) |

TABLE 1-continued

Exemplary Formula and Compounds

| Formula | Name | Structure |
|---|---|---|
| XXVIII | XT-206 | 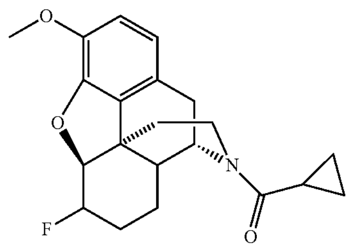 [SMILES: COc1ccc2c3c1O[C@@H]1C(F)CCC4[C@H](C2)N(C(=O)C2CC2)CC[C@]341] |
| XXIX | XT-207 | 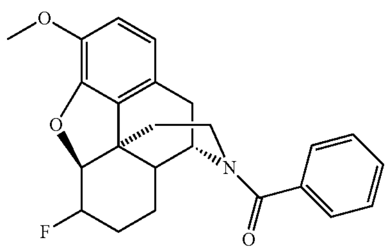 [SMILES: COc1ccc2c3c1O[C@@H]1C(F)CCC4[C@H](C2)N(C(=O)c2ccccc2)CC[C@]341] |
| XXX | XT-211 | 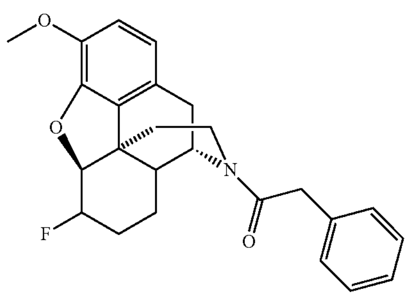 [SMILES: COc1ccc2c3c1O[C@@H]1C(F)CCC4[C@H](C2)N(C(=O)Cc2ccccc2)CC[C@]341] |
| XXXI | XT-216 | 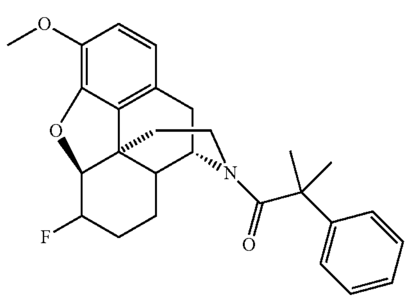 [SMILES: COc1ccc2c3c1O[C@@H]1C(F)CCC4[C@H](C2)N(C(=O)C(C)(C)c2ccccc2)CC[C@]341] |
| XXXII | XT-209 | 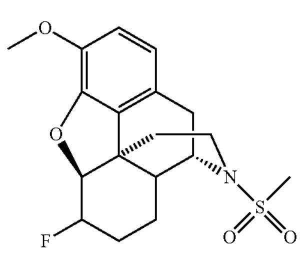 |
| XXXIII | XT-212 | 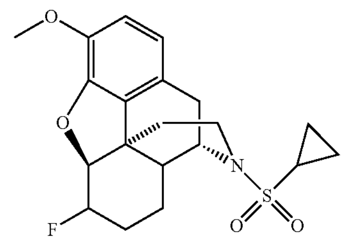 [SMILES: COc1ccc2c3c1O[C@@H]1C(F)CCC4[C@H](C2)N(S(=O)(=O)C2CC2)CC[C@]341] |
| XXXIV | XT-208 | 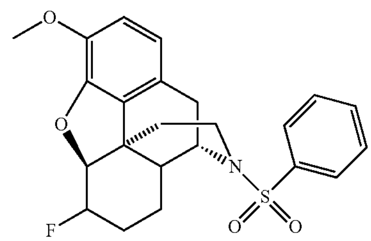 [SMILES: COc1ccc2c3c1O[C@@H]1C(F)CCC4[C@H](C2)N(S(=O)(=O)c2ccccc2)CC[C@]341] |
| XXXV | XT-217 | 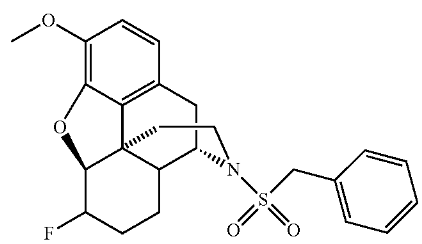 [SMILES: COc1ccc2c3c1O[C@@H]1C(F)CCC4[C@H](C2)N(S(=O)(=O)Cc2ccccc2)CC[C@]341] |
| XXXVI | | 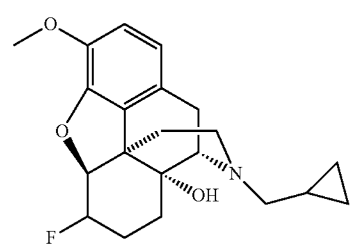 [SMILES: COc1ccc2c3c1O[C@@H]1C(F)CC[C@]4(O)[C@H](C2)N(CC2CC2)CC[C@@]314] |

In certain embodiments, a compound is of Formula I. In certain embodiments, a compound of Formula I is the (+)-isomer. In some embodiments, a compound of Formula I is the (−)-isomer.

In certain embodiments, $R_1$ is methoxy. In some embodiments, $R_1$ is hydroxyl. In certain embodiments, $R_1$ is ethoxy. In certain embodiments, $R_1$ is $C_{1-6}$-alkoxy (e.g., propoxy, butoxy, pentoxy, isopropoxy). In some embodiments, $R_1$ is phenoxy. In some embodiments, $R_1$ is naphthoxy.

In some embodiments, $R_2$ is methyl. In certain embodiments, $R_2$ is selected from the group consisting of ethyl, n-propyl, isopropyl, n-butyl, tert-butyl, sec-butyl, isobutyl, n-pentyl, neopentyl, tert-pentyl, isopentyl, sec-pentyl, 3-pentyl, sec-isopentyl, n-hexyl, or hexyl. In certain embodiments, $R_2$ is cyclopropylmethyl. In some embodiments, $R_2$ is dicyclopropylmethyl or 1-cyclopropylethyl. In certain embodiments, $R_2$ is 2-propenyl. In some embodiments, $R_2$ is cyclohexyl. In certain embodiments, $R_2$ is 1-phenylethyl or 1-methyl-2-phenyl-ethyl. In certain embodiments, $R_2$ is benzyl. In some embodiments, $R_2$ is

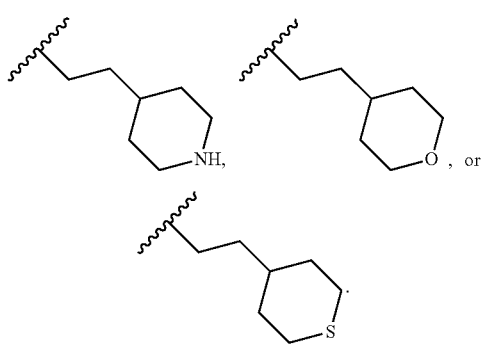

In certain embodiments, R₂ is

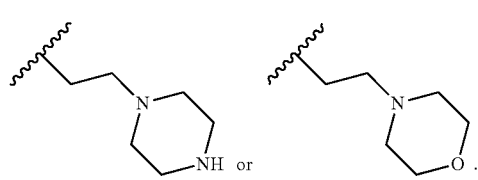 [SMILES: *CCN1CCNCC1 ; *CCN1CCOCC1]

In some embodiments, R₂ is

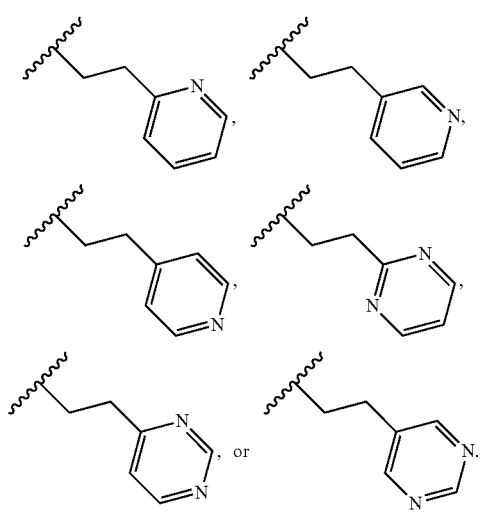

In certain embodiments, R₂ is

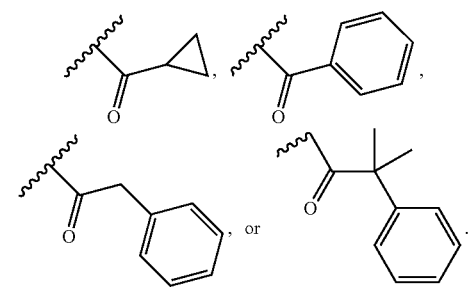

In some embodiments, R₂ is

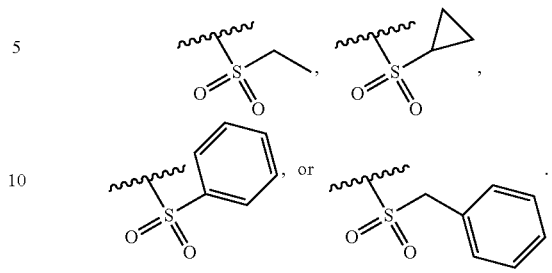

In certain embodiments, R₂ is

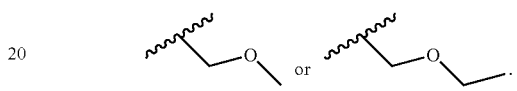

In some embodiments, Y is hydrogen. In certain embodiments, Y is hydroxyl.

In certain embodiments, X is fluorine. In some embodiments, X is chlorine. In certain embodiments, X is bromine. In some embodiments, X is iodine.

In some embodiments, Z is hydrogen. In certain embodiments, Z is fluorine. In some embodiments, Z is chlorine. In certain embodiments, Z is bromine. In some embodiments, Z is iodine.

In some embodiments, X is fluorine, and Z is hydrogen. In certain embodiments, X is fluorine, and Z is fluorine. In some embodiments, X is chlorine, and Z is hydrogen. In certain embodiments, X is chlorine, and Z is chlorine. In certain embodiments, X is fluorine, and Z is chlorine. In some embodiments, R₁ is methoxy, R₂ is cyclopropylmethyl, Y is hydrogen, X is fluorine, and Z is hydrogen. In certain embodiments, R₁ is methoxy, R₂ is cyclopropylmethyl, Y is hydroxy, X is fluorine, and Z is hydrogen. In some embodiments, R₁ is methoxy, R₂ is cyclopropyl, Y is hydrogen, X is fluorine, and Z is hydrogen.

In certain embodiments, Formula I contains a single bond between carbons 7 and 8. In some embodiments, Formula I contains a double bond between carbons 7 and 8.

In certain embodiments, Formula I contains a single bond between carbons 1 and 2. In certain embodiments, Formula I contains a single bond between carbons 3 and 4. In certain embodiments, Formula I contains a single bond between carbons 11 and 15. In certain embodiments, Formula I contains a single bond between carbons 1 and 2, 3 and 4, and 11 and 15. In certain embodiments, Formula I contains a double bond between carbons 1 and 2. In certain embodiments, Formula I contains a double bond between carbons 3 and 4. In certain embodiments, Formula I contains a double bond between carbons 11 and 15. In certain embodiments, Formula I contains a double bond between carbons 1 and 2, 3 and 4, and 11 and 15.

In certain embodiments, Formula I contains a double bond between carbons 1 and 2, 3 and 4, and 11 and 15 and a single bond between carbons 7 and 8. In some embodiments, Formula I contains a double bond between carbons 1 and 2, 3 and 4, 11 and 15 and a double bond between carbons 7 and 8

In certain embodiments, a compound of Formula I is of the formula:

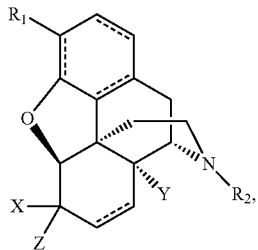

Formula IA or a pharmaceutically acceptable salt thereof

In certain embodiments, each ═══ is independently a single bond. In certain embodiments, each ═══ is independently a double bond. In certain embodiments, each ═══ is a single bond. In some embodiments, each ═══ is a double bond. In certain embodiments, each ═══ between carbons 1 and 2, 3 and 4, and 11 and 15 of Formula 1 is a double bond.

In certain embodiments, a compound of Formula I is of the formula:

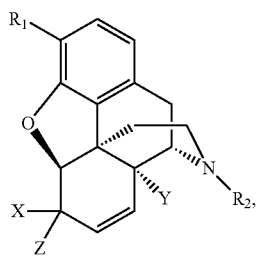

Formula IB or a pharmaceutically acceptable salt thereof

In certain embodiments, a compound of Formula I is of the formula:

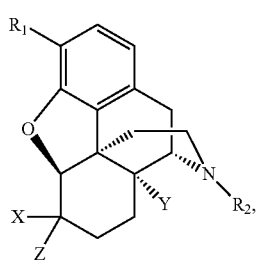

Formula IC or a pharmaceutically acceptable salt thereof

In certain embodiments, a compound of Formula I is of one of the following formulae:

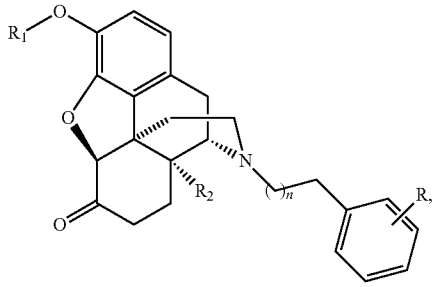

Formula XVII

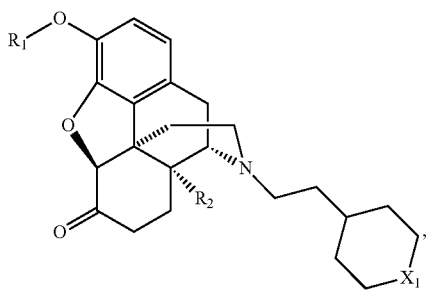

Formula XVIII

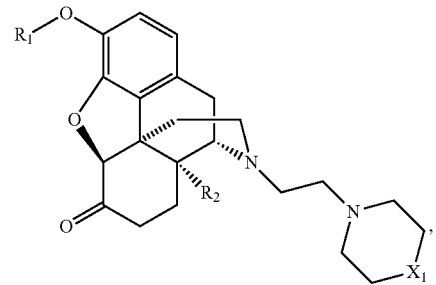

Formula XIX

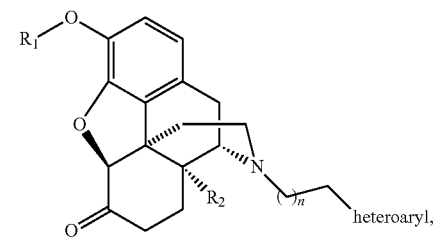

Formula XX

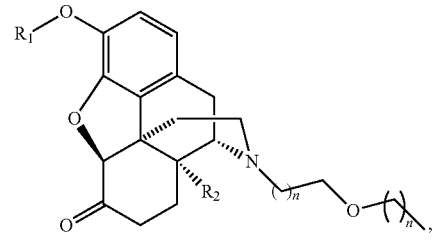

Formula XXI or pharmaceutically acceptable salts thereof

In some embodiments, n is 0. In certain embodiments, n is 1. In some embodiments, n is 2, 3, 4, or 5.

In certain embodiments, $X_1$ is NH. In some embodiments, $X_1$ is O. In certain embodiments, $X_1$ is S. In certain embodiments, $X_1$ is $C(R^a)_2$ wherein each $R^a$ is independently hydrogen, $C_1$-$C_4$ alkyl, phenyl, hydroxyl, and $C_1$-$C_4$-alkoxyl.

In certain embodiments, R is hydrogen. In certain embodiments, R is halogen. In certain embodiments, R is —F. In certain embodiments, R is —Cl, —Br, or —F. In certain embodiments, R is —$NO_2$. In certain embodiments, R is —CN. In certain embodiments, R is —$OR^4$. In certain embodiments, R is —$OR^5$. In certain embodiments, R is —$OR^e$ (e.g. —OH, —OMe, —O($C_{1-6}$ alkyl)). In certain embodiments, R is —OH. In certain embodiments, R is —$OR^e$, and $R^e$ is an oxygen protecting group. In certain embodiments, R is —$N(R^e)_2$ (e.g., —$NH_2$, —$NMe_2$, —NH($C_{1-6}$ alkyl)). In certain embodiments, R is —$NHR^e$, and $R^e$ is a nitrogen protecting group. In certain embodiments, R is optionally substituted acyl (e.g., —C(=O)($R^e$), —C(=O)O($R^e$), —C(=O)NH($R^e$), —C(=O)N($R^e)_2$). In some embodiments, R is —C(=O)OMe. In some embodiments, R is —C(=O)OH. In certain embodiments, R is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, R is optionally substituted $C_{1-6}$ alkyl. In certain embodiments, R is substituted methyl. In certain embodiments, R is substituted ethyl, propyl, or butyl. In certain embodiments, R is unsubstituted $C_{1-6}$ alkyl. In certain embodiments, R is unsubstituted methyl. In certain embodiments, R is unsubstituted ethyl, propyl, or butyl. In certain embodiments, R is optionally substituted alkenyl, e.g., optionally substituted $C_{2-6}$ alkenyl. In certain embodiments, R is vinyl, allyl, or prenyl. In certain embodiments, R is optionally substituted alkynyl, e.g., $C_{2-6}$ alkynyl. In certain embodiments, R is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments R is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, R is optionally substituted aryl, e.g., optionally substituted phenyl. In certain embodiments, R is optionally substituted heteroaryl, e.g., optionally substituted 5-6 membered heteroaryl, or optionally substituted 9-10 membered bicyclic heteroaryl. In certain embodiments, R is optionally substituted aralkyl, e.g., optionally substituted benzyl. In certain embodiments, R is optionally substituted heteroaralkyl, e.g., methyl substituted with a 5-6-membered heteroaryl ring.

In some embodiments, heteroaryl is selected from the group selected from pyrrolyl, furanyl, thiophenyl, imidazolyl, pyrazolyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, triazinyl, tetrazinyl, azepinyl, oxepinyl, thiepinyl, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, purinyl, naphthyridinyl, pteridinyl, quinolinyl, isoquinolinyl, cinnolinyl, quinoxalinyl, phthalazinyl, quinazolinyl, phenanthridinyl, dibenzofuranyl, carbazolyl, acridinyl, phenothiazinyl, phenoxazinyl and phenazinyl, in some embodiments, heteroaryl is pyridinyl or pyrimidinyl. In certain embodiments, heteroaryl is tetrazolyl or triaolyl. In certain embodiments, heteroaryl is quinolinyl or indolyl.

In certain embodiments, a compound of Formula I is of one of the following formula:

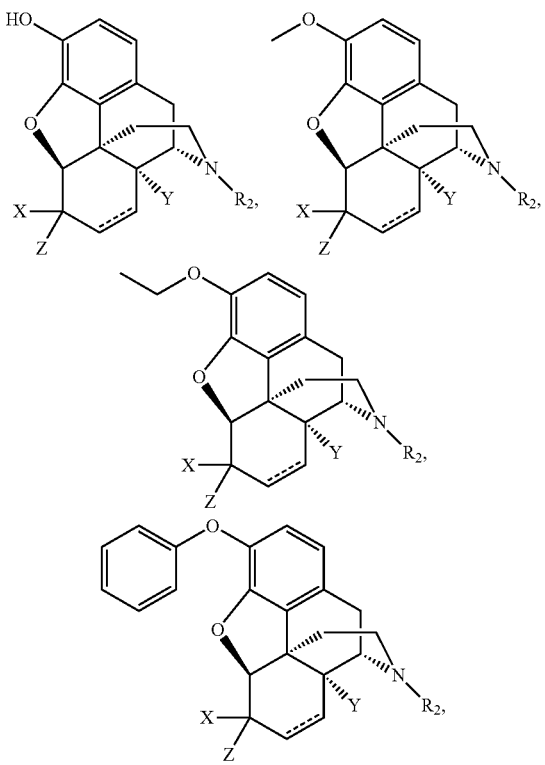

or a pharmaceutically acceptable salt thereof.

In certain embodiments, a compound of Formula I is of one of the following formula:

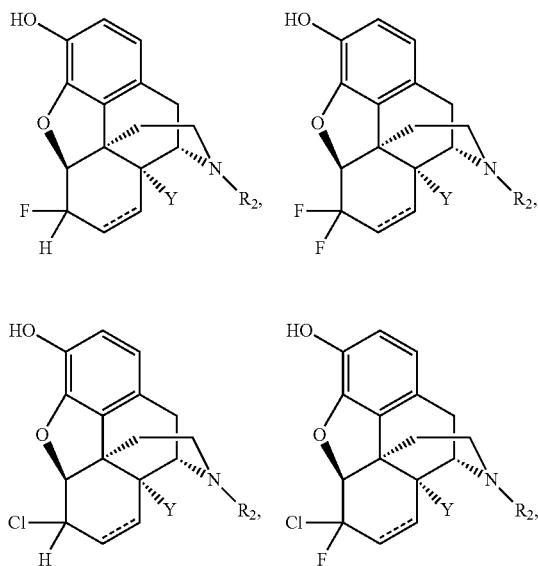

or a pharmaceutically acceptable salt thereof.

In certain embodiments, a compound of Formula I is of one of the following formula:
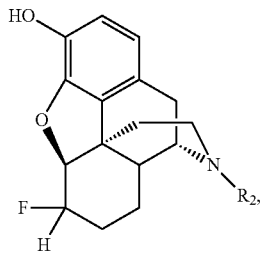 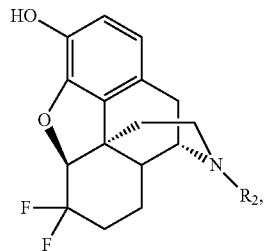
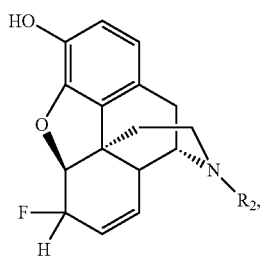 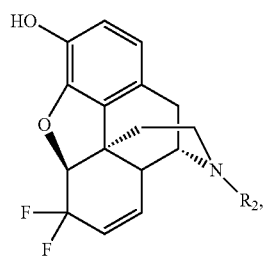
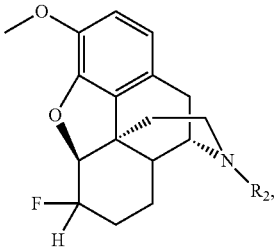 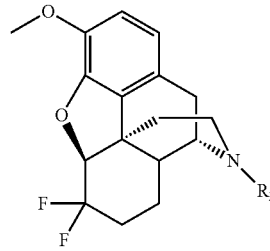
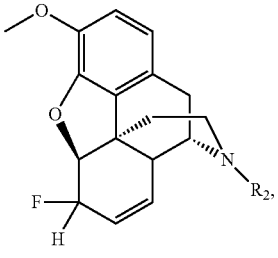 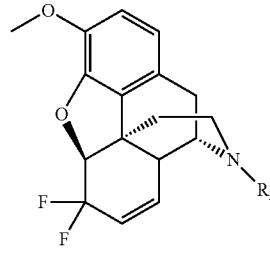
or a pharmaceutically acceptable salt thereof.
In certain embodiments, a compound of Formula I is of one of the following formula:
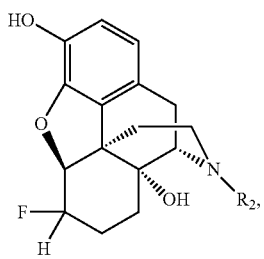 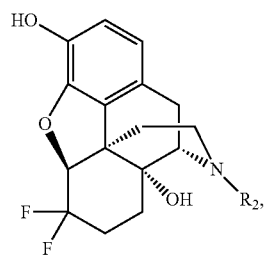
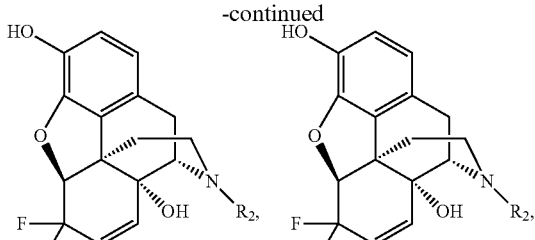
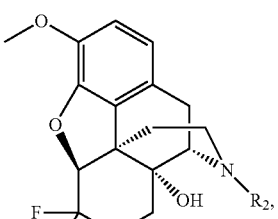 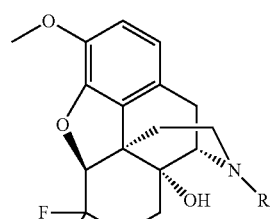
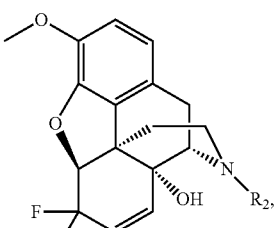 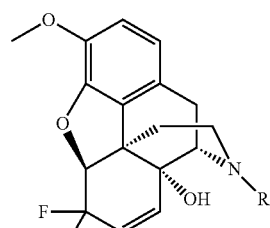
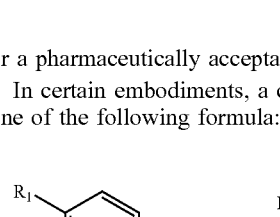 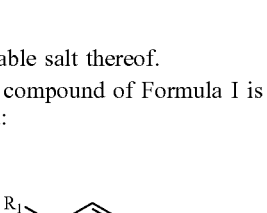
or a pharmaceutically acceptable salt thereof.
In certain embodiments, a compound of Formula I is of one of the following formula:
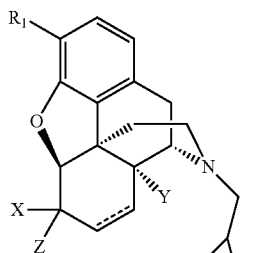 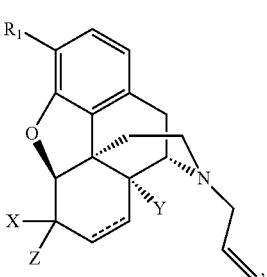
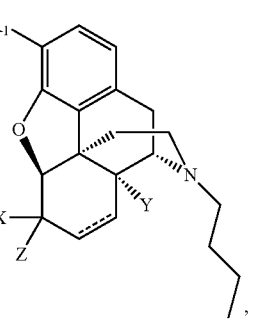 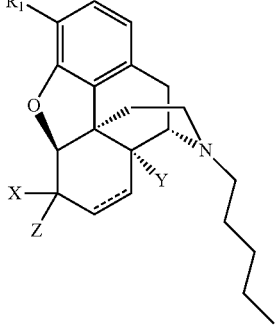

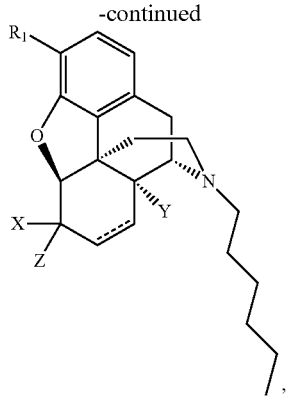
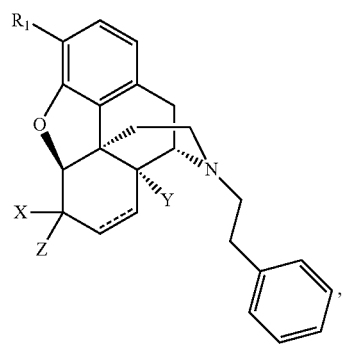
or a pharmaceutically acceptable salt thereof.
In certain embodiments, a compound of Formula I is of one of the following formula:
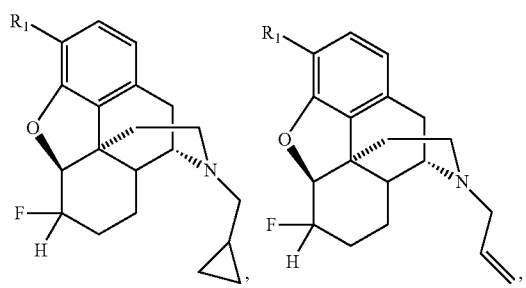
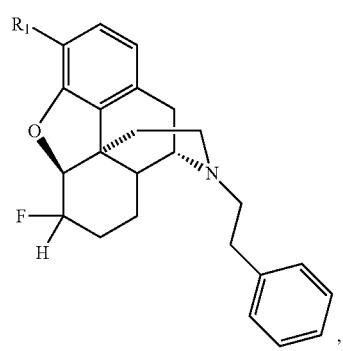
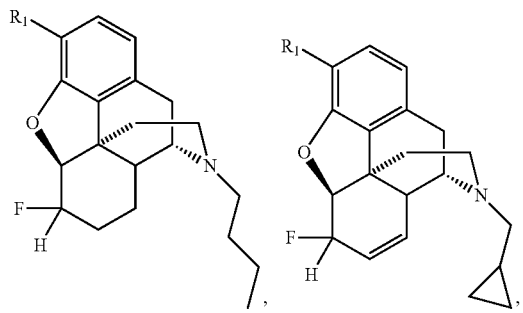
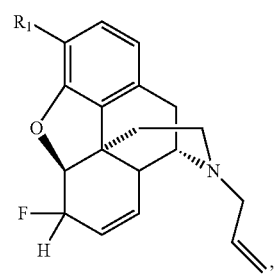
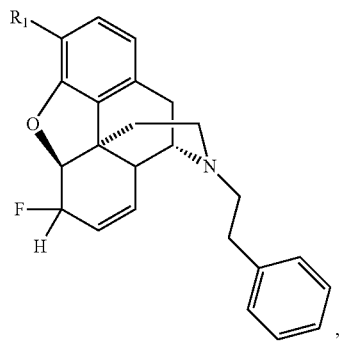
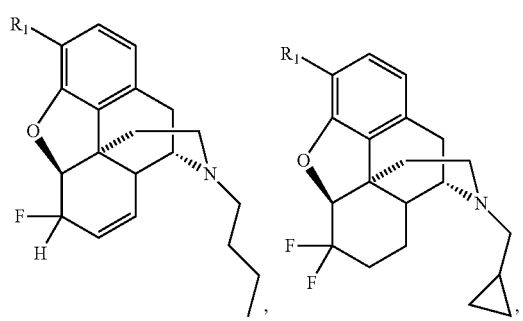
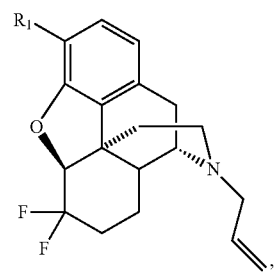

-continued
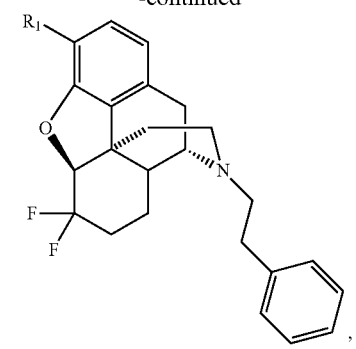
,
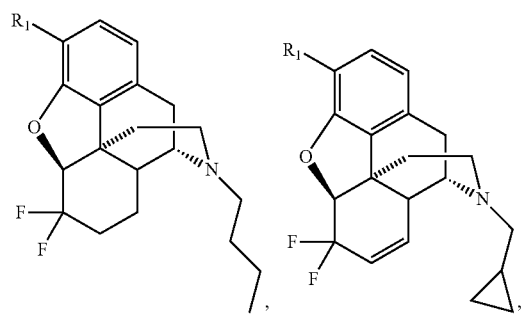
,
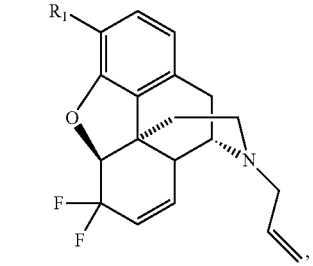
,
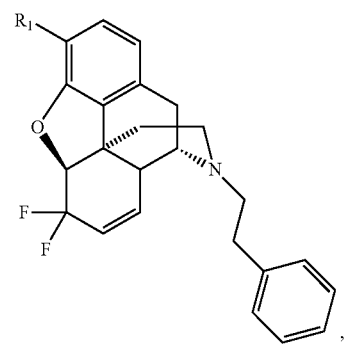
,
or a pharmaceutically acceptable salt thereof.
In certain embodiments, a compound of Formula I is of one of the following formula:
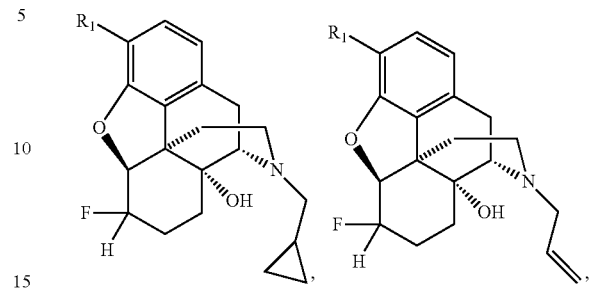
,
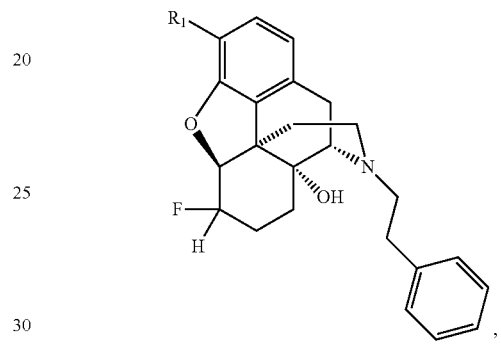
,
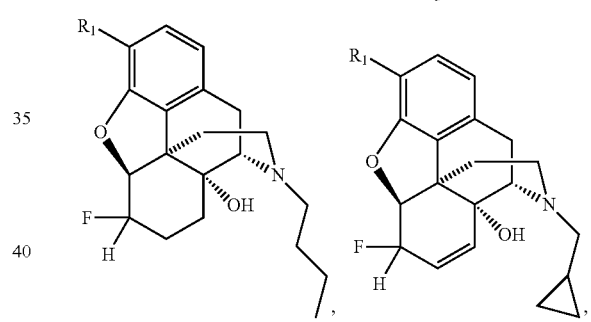
,
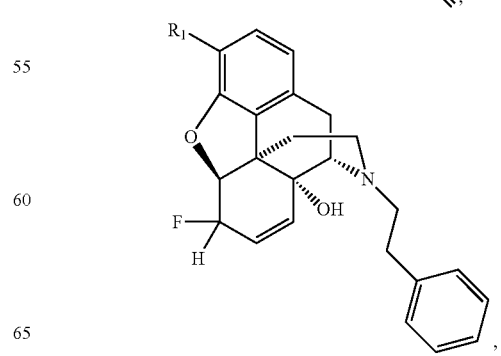
, -continued
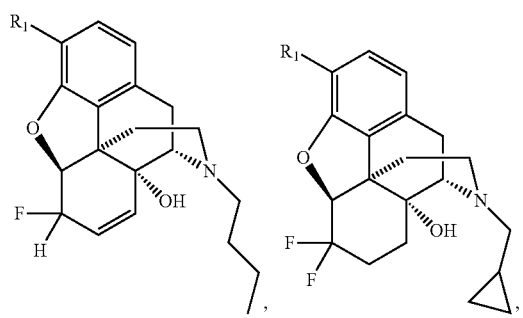
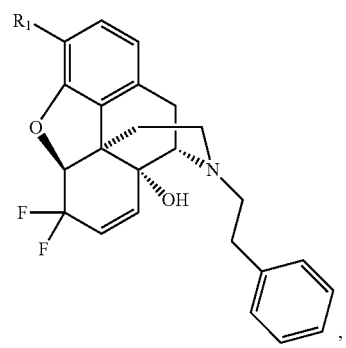
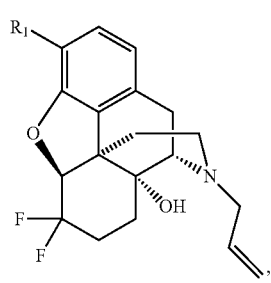
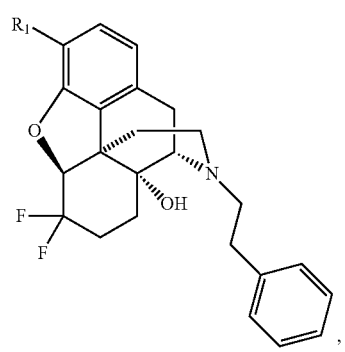
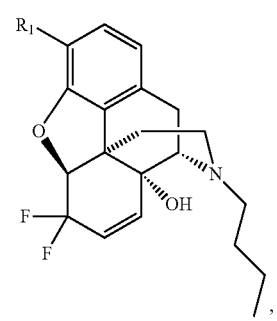
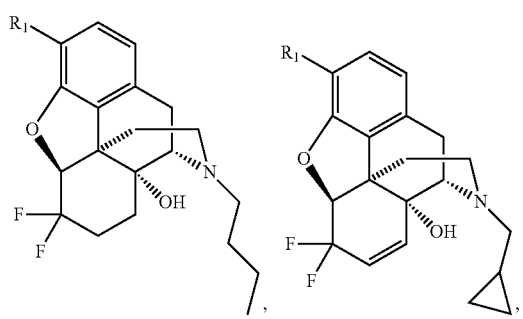
or a pharmaceutically acceptable salt thereof.
In certain embodiments, a compound of Formula I is of one of the following formula:
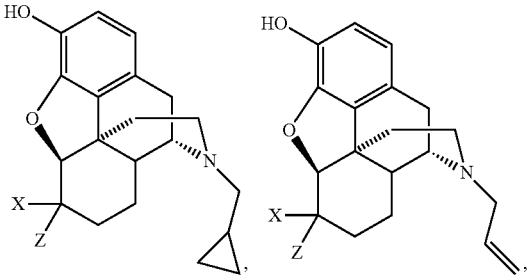
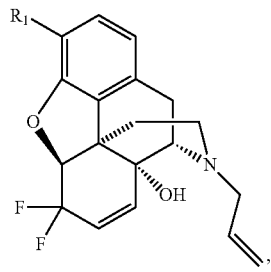
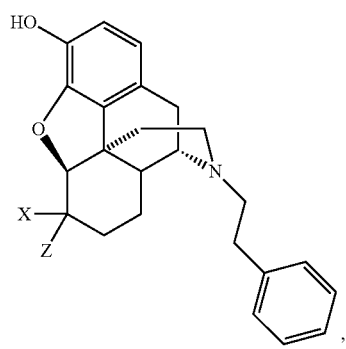

53
-continued
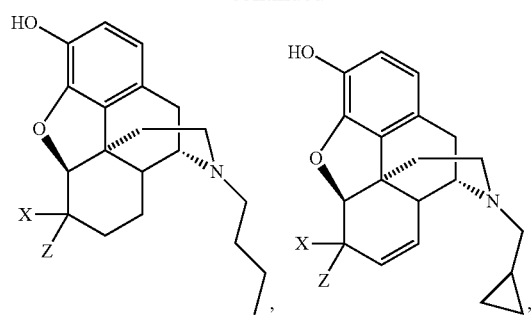
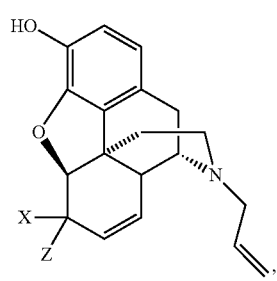
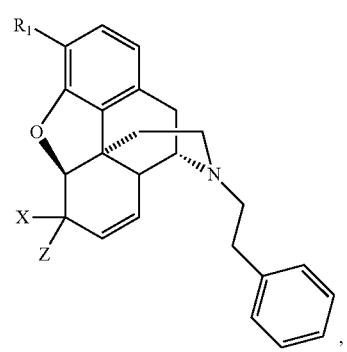
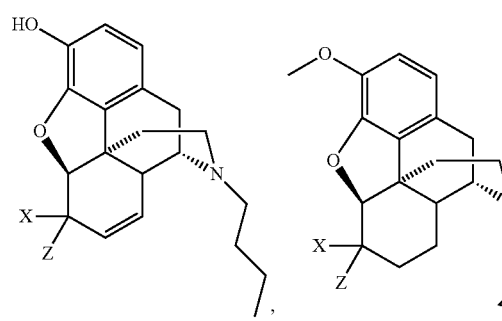
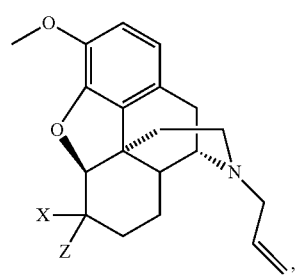
54
-continued
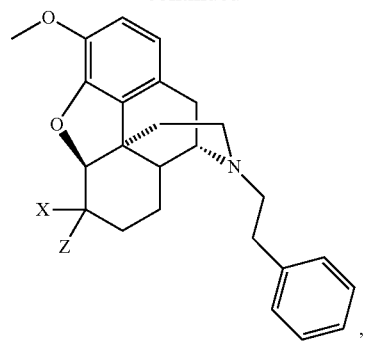
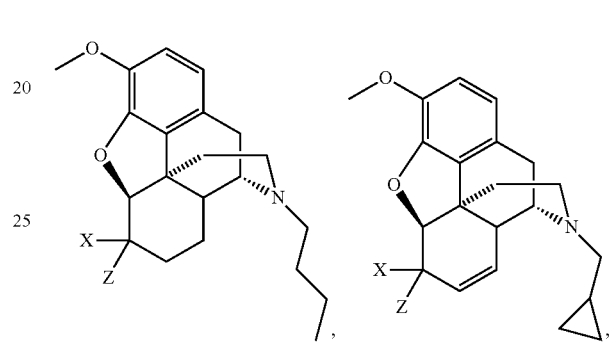
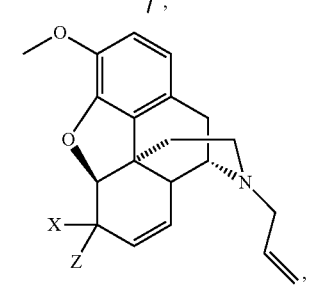
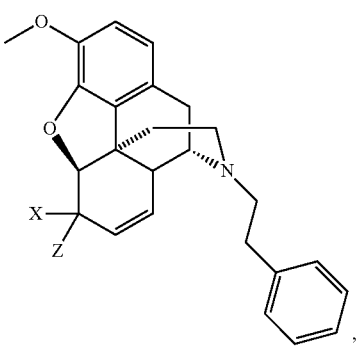
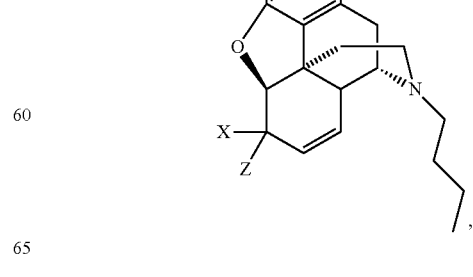
or a pharmaceutically acceptable salt thereof.

In certain embodiments, a compound of Formula I is of one of the following formula:
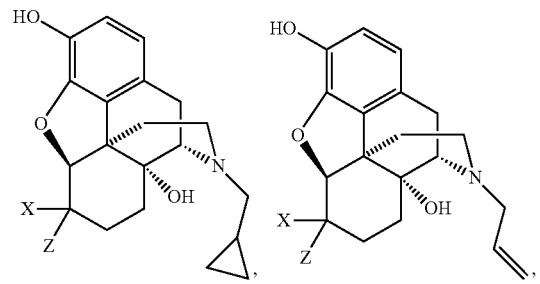
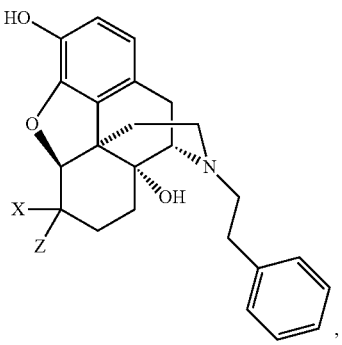
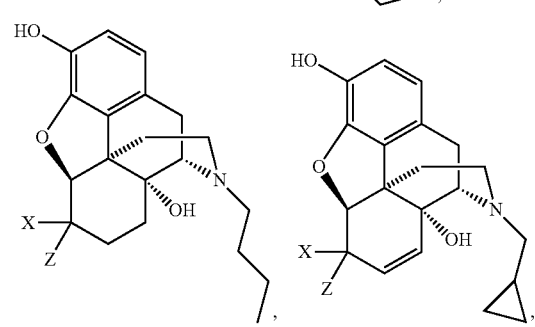
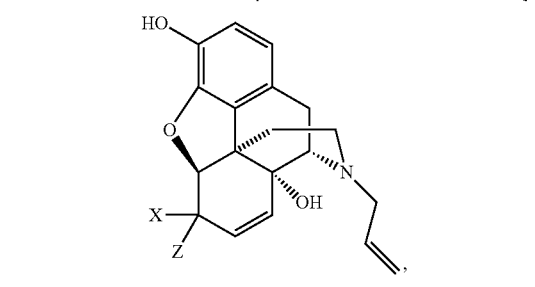
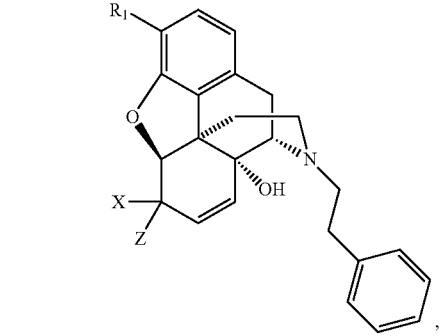
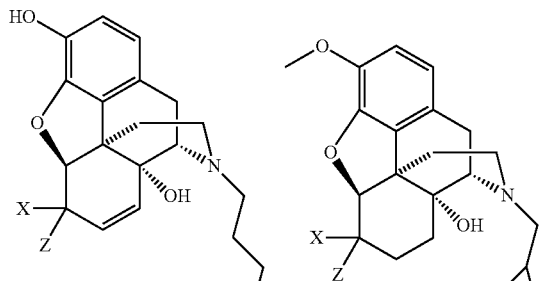
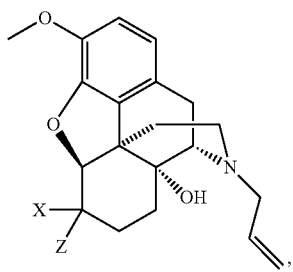
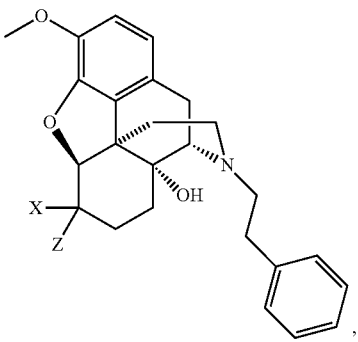

-continued
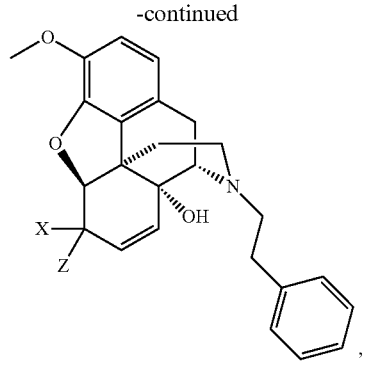
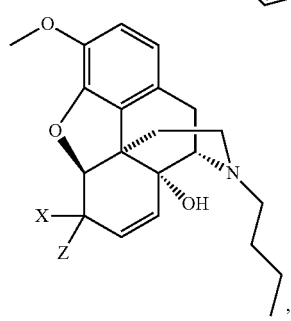
or a pharmaceutically acceptable salt thereof.
In certain embodiments, a compound of Formula I is of one of the following formulae:
Formula XXII
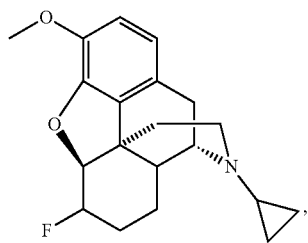
Formula XXV
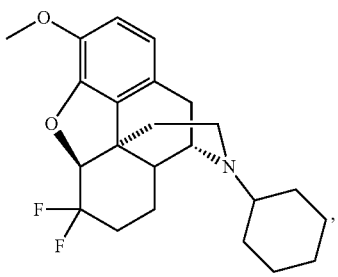
Formula XXVI
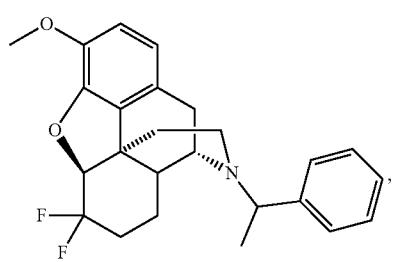
-continued
Formula XXVII
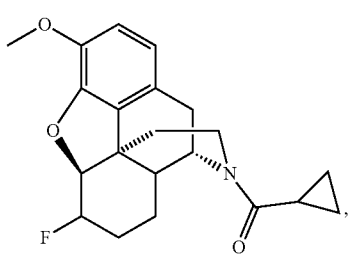
Formula XXVIII
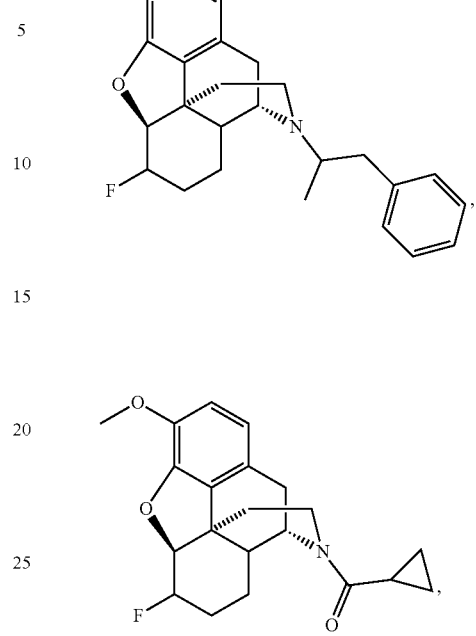
Formula XXIX
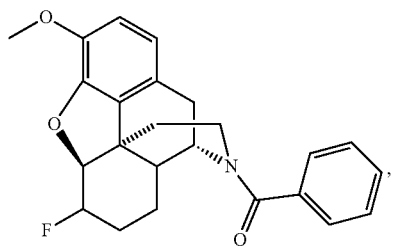
Formula XXX
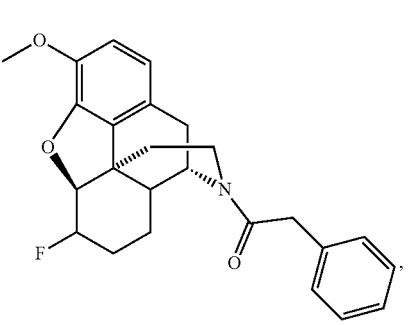
Formula XXXI
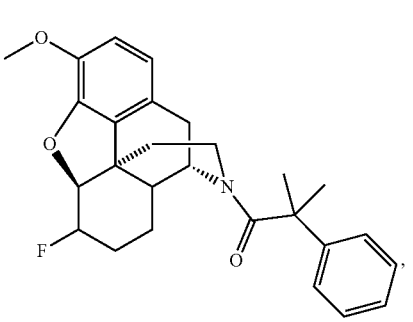

-continued

Formula XXXII
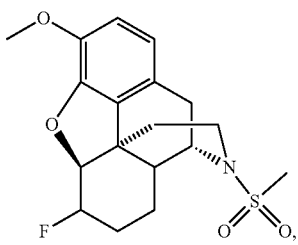

Formula XXXIII
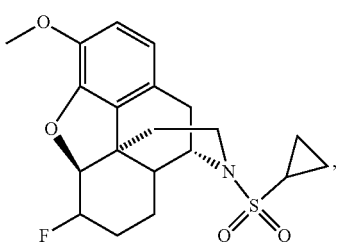

Formula XXXIV
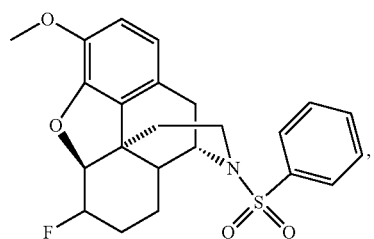

Formula XXXV
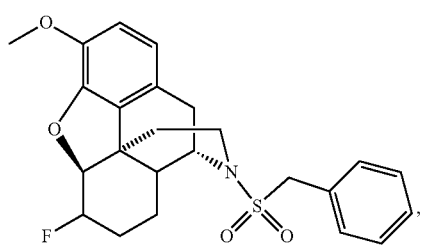

or a pharmaceutically acceptable salt thereof

In certain embodiments, a compound of Formula I is of the Formula VII:

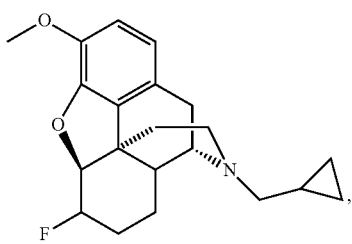

or a pharmaceutically acceptable salt thereof.

In certain embodiments, a compound of Formula I is of the Formula IX:

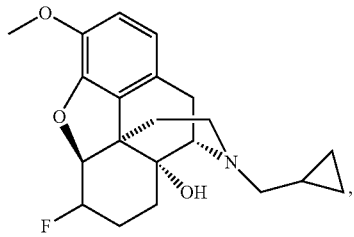 [SMILES: COc1ccc2c3c1O[C@@H]1C(F)CC[C@]4(O)[C@H](C2)N(CC2CC2)CC[C@@]314]

or a pharmaceutically acceptable salt thereof.

In certain embodiments, a compound of Formula I is of the Formula XXVIII:

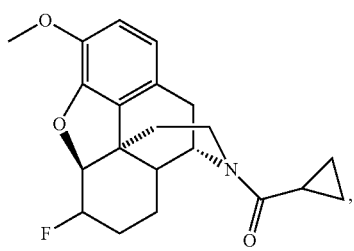 [SMILES: COc1ccc2c3c1O[C@@H]1C(F)CCC4[C@H](C2)N(C(=O)C2CC2)CC[C@]341]

or a pharmaceutically acceptable salt thereof.

In certain embodiments, a compound of Formula I is of the Formula XXXIII:

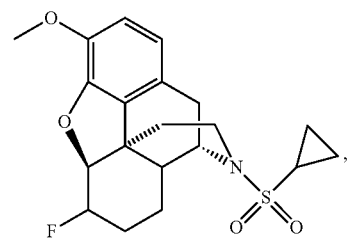 [SMILES: COc1ccc2c3c1O[C@@H]1C(F)CCC4[C@H](C2)N(S(=O)(=O)C2CC2)CC[C@]341]

or a pharmaceutically acceptable salt thereof.

Synthesis

Opium provides (−)-opioids, such as (−)-morphine, (−)-codeine, and (−)-thebaine, that are useful in the manufacture of medical narcotics. The vast majority of opiate chemistry published to date was developed using (−)-isomers of morphine, codeine, and thebaine from opium poppies and their transformation products, or from sinomenine that has the carbon-nitrogen skeleton antipodal to the opium derived-products. The procedures derived from opium products are applicable to the synthesis of the corresponding (+)-isomers as the required intermediates are now independently available either by total synthesis or from sinomenine (see below). Conversely, the procedures developed from the work with sinomenine are applicable to the synthesis of drugs with the natural opiate absolute configuration.

Exemplary opiate synthesis and intermediates are described in U.S. Pat. Nos. 4,368,326, 4,410,700, 4,556,712, 4,521,601, 4,613,668, 5,008,449 and 5,668,285 and European patent EP0418591A2, each of which is incorporated herein by reference. Procedures disclosed in these patents are applicable to the synthesis of the unnatural (+)-enantiomers. These unnatural enantiomers generally have (+)-optical rotation although some exceptions are known such as simonenine. Briefly, these procedures use commercially available starting materials such as 3-methoxyphenethylamine and 3-hydroxy-4-methoxyphenylacetic acid and provide either enantiomers of 1-bromo-nordihydrothebainone, dihydrothebainone, nordihydrocodeinone and dihydrocodeinone in about 40% overall yield. Either enantiomer of the entire spectrum of compounds described in the opiate chemistry art can be synthesized from the appropriate enantiomer of any one of the latter four compounds by applying published procedures.

Alternatively, (+)-dihydrocodeinone can be prepared from (−)-sinomenine, a commercially-available plant alkaloid with the same absolute configuration as the unnatural opiates. The availability of (+)-dihydrocodeinone either by total synthesis or from (−)-sinomenine thus provides two independent routes to this intermediate and to the entire spectrum of unnatural opiates using procedures published for compounds in both the (−)-series and the (+)-series.

Thus, compounds of the invention can be readily prepared from available starting materials using the procedures known for (+)-opioids. Various substituents on the compounds of the invention can be present in the starting compounds, added to any one of the intermediates or added after formation of the final products by known methods of substitution or conversion reactions. For example, nitro groups can be added by nitration and the nitro group can then be converted to other groups, such as amino by reduction, or a halogen by diazotization of the amino group and replacement of the diazo group with a halogen or simply by a halogenation reaction. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in Greene and Wuts, *Protecting Groups in Organic Synthesis,* 3rd ed., John Wiley & Sons, New York, 1999, and references cited therein, all of which are incorporated by reference in their entirety.

Some of the methods for producing various (+)-opioid compounds are disclosed in European Patent Application No. 90116248.7. In addition, one skilled in the art can use methods described for synthesis of (−)-opioid compounds; for example, there are a number of U.S. Patents (such as those described above) that provide procedures on how to produce (+)-opioid compounds by using enantiomers. Optimum reaction conditions may vary with the particular reactants or solvent used, but such conditions can be determined by one skilled in the art by routine optimization procedures.

Since the compounds of the invention can have certain substituents that are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to one of ordinary skill in the art. This would further be dependent on the ring involved.

In some instances, a racemic mixture of compounds of the invention can be prepared and the desired (+)-isomer can be resolved or separated (i.e., enantiomerically enriched) using any of the variety of chiral resolution methods known to one skilled in the art. Such resolution methods are described, for example, in the four volume compendium *Optical Resolution Procedures for Chemical Compounds: Optical Resolution Information Center*, Manhattan College, Riverdale, N.Y.; and in Jacques, Collet and Wilen, Enantiomers, Racemates and Resolutions, John Wiley & Sons, Inc., New York (1981), both of which are incorporated herein in their entirety.

The compounds of the invention form salts with acids when a basic amino function is present and salts with bases when an acid function, e.g., carboxylic acid or phosphonic acid, is present. All such salts are useful in the isolation and/or purification of the new products. Of particular value are the pharmaceutically acceptable salts with both acids and bases. Suitable acids include, for example, hydrochloric, oxalic, sulfuric, nitric, benzenesulfonic, toluenesulfonic, acetic, maleic, tartaric and the like which are pharmaceutically acceptable. Basic salts for pharmaceutical use include Na, K, Ca and Mg salts.

Figure 3A:
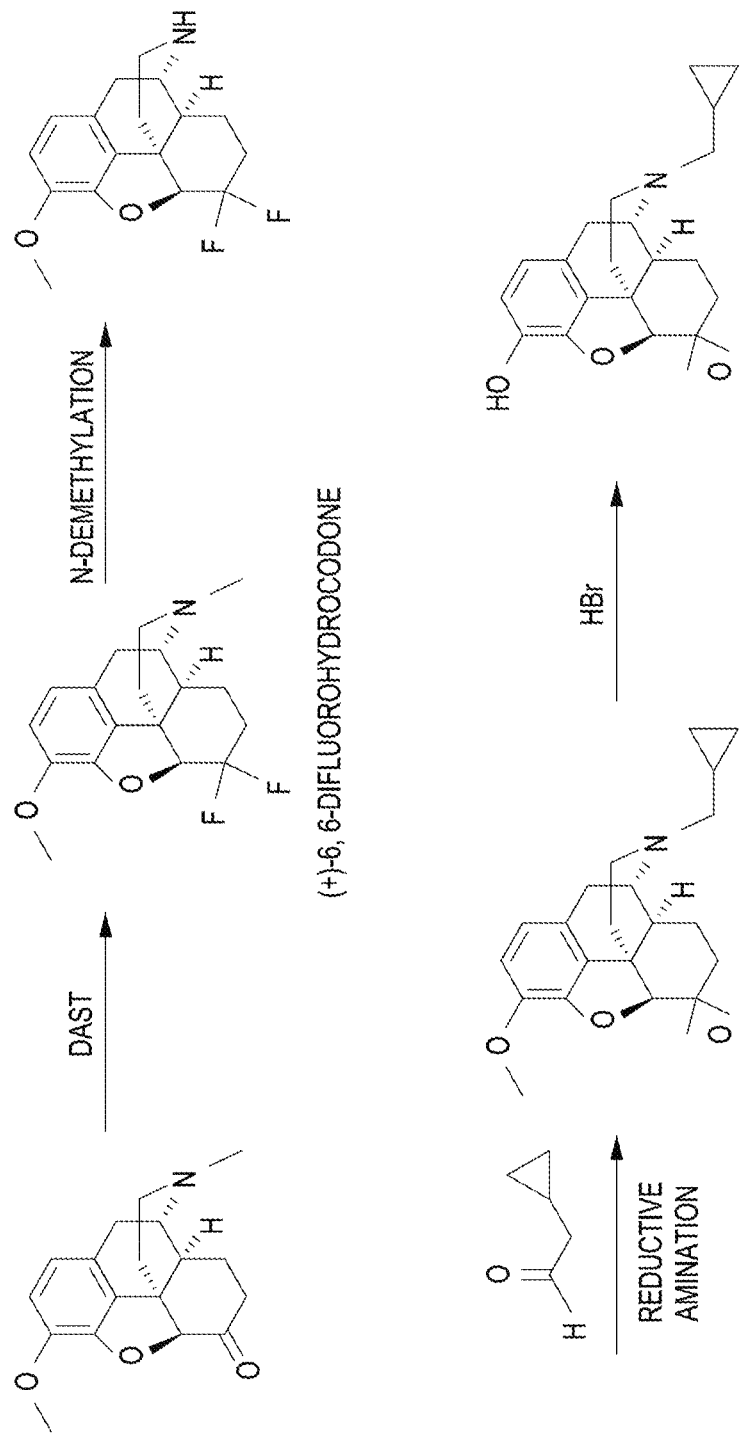
FIG. 3A shows a synthesis pathway of (+)-6,6-difluoro-deshydroxy-naltrexone.
Figure 3B:
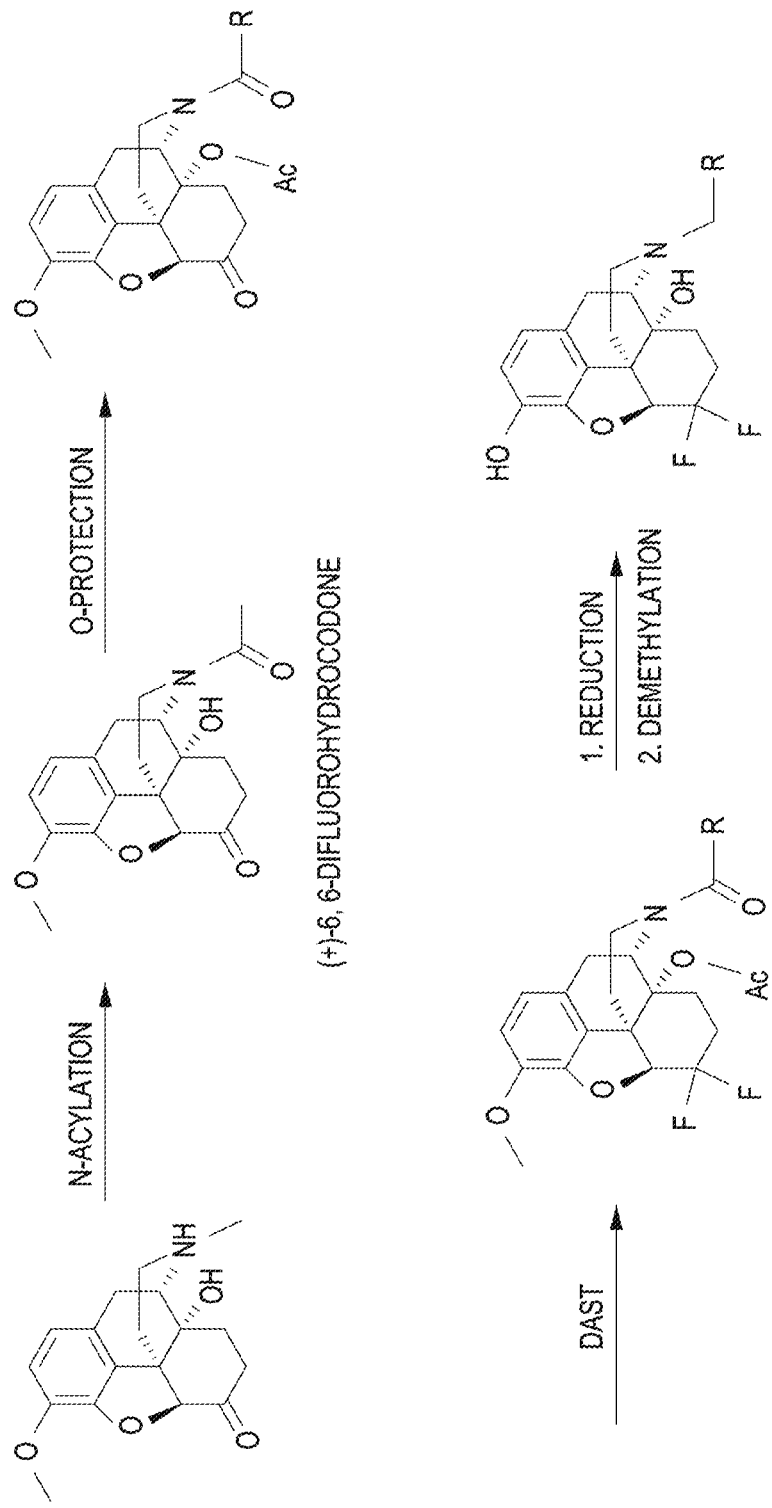
FIG. 3B shows a synthesis pathway that can be used to synthesize Formulas II, III, V, and VI of FIG. 2.
Figure 4:
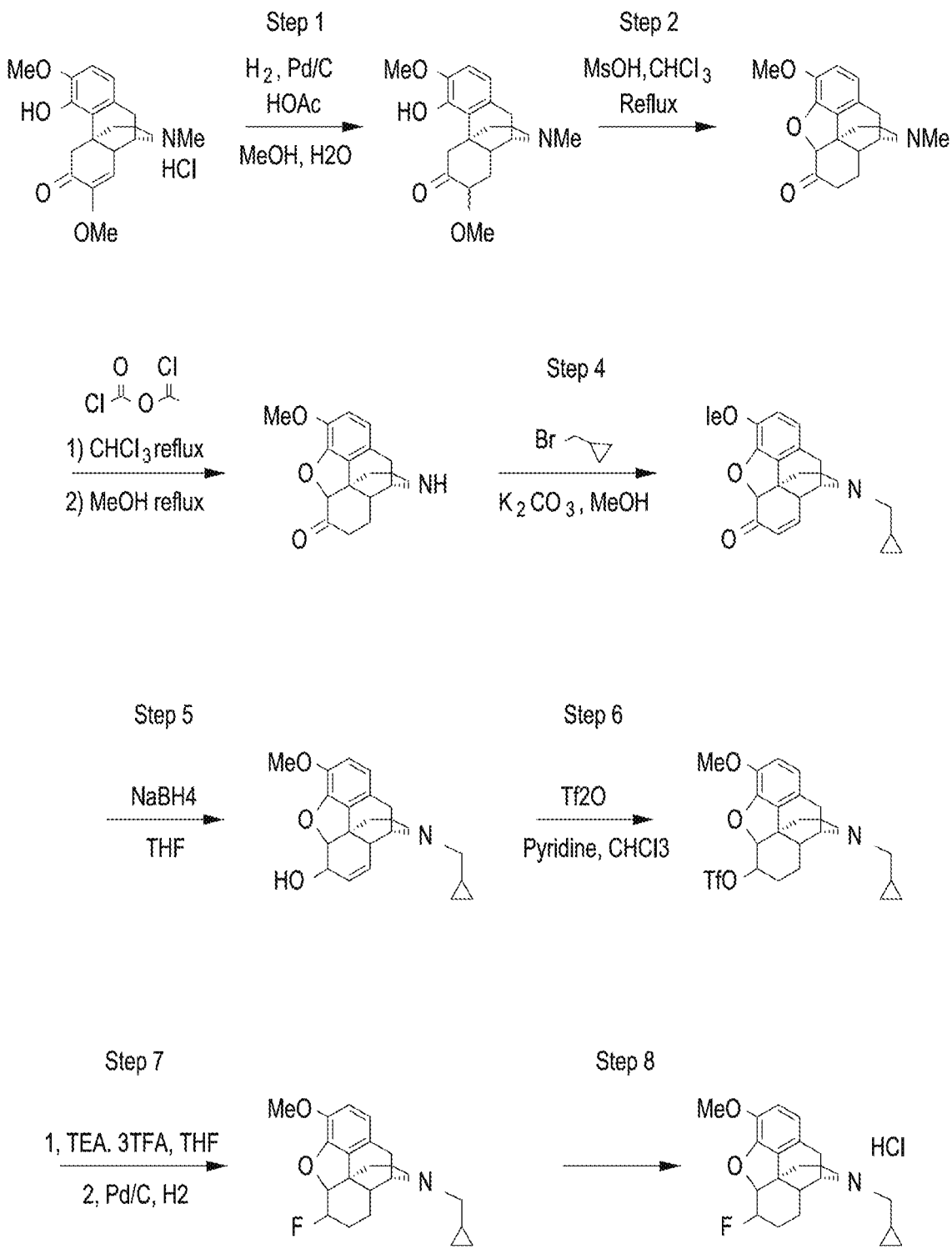
FIG. 4 shows an exemplary synthetic pathway that can be used to synthesize Formula VII (XT-203) of FIG. 2A.

FIGS. 3A and 3B show exemplary synthetic methodologies for preparing select halogenated morphians of Formula I. In these examples, the halogen is fluorine, and the chemistry involves fluorination of the 6-keto functionality of the (+)-morphians. FIG. 4 shows a synthesis scheme for XT-203 (shown in FIG. 2A as Formula VII).

Pharmaceutical Compositions

The compounds of the invention can be administered to a patient to achieve a desired physiological effect. Typically the patient is a mammal. The compound can be administered in a variety of forms adapted to the chosen route of administration, i.e., orally or parenterally. Parenteral administration includes administration by the following routes: intravenous; intramuscular; subcutaneous; intraocular; intrasynovial; transepithelially including transdermal, ophthalmic, sublingual and buccal; topically, including ophthalmic, dermal, ocular, rectal and nasal or pulmonary inhalation via insufflation and aerosol; intraperitoneal; and central (e.g., intrathecal, such as into the cerebrospinal fluid around the spinal cord, and intracerebral into brain or cerebrospinal fluid of the brain).

The active compound can be orally administered, for example, with an inert diluent or with an assimilable edible carrier, it can be enclosed in hard or soft shell gelatin capsules, or it can be compressed into tablets. For oral therapeutic administration, the active compound may be incorporated with an excipient. Such compositions and preparation can contain at least 25% of active compound. The percentage of the compositions and preparation can, of course, be varied and can conveniently be between about 25 to about 85% of the weight of the unit. The amount of active compound in the therapeutically useful compositions is such that a suitable dosage will be obtained. Preferred compositions or preparations according to the present invention are prepared such that an oral dosage unit form contains from about 68 to about 136 mg of active compound. Preferred compositions or preparations according to the present invention are prepared such that an oral dosage unit form contains from about 48 to about 300 mg of active compound.

The active compound can also be administered parenterally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that the compound can be delivered via a syringe. The compound preferably is formulated to be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride.

Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of the invention can be administered alone or in combination with pharmaceutically acceptable carriers, as noted above, the proportion of which is determined by the solubility and chemical nature of the compound, chosen route of administration and standard pharmaceutical practice.

A physician may determine the dosage of the present therapeutic agents that is the most suitable for prophylaxis or treatment and it will vary with the form of administration and the particular compound chosen, and the dosage will vary with the particular patient under treatment. The physician will generally wish to initiate treatment with small dosages by small increments until the optimum effect under the circumstances is reached. The actual doses to be administered depend on the results of both toxicology and efficacy studies, as well as the route of administration appropriate for the specific therapeutic condition or paradigm. For subcutaneous dosing, the therapeutic dosage can generally be from about 5 to 1500 mg/dose and can be administered in several different dosage units and more than once daily. For subcutaneous dosing, the therapeutic dosage can generally be from about 48 to 300 mg/dose and can be administered in several different dosage units and more than once daily. For subcutaneous dosing, the therapeutic dosage can generally be from about 0.8 to 100 mg/kg or about 10 to 30 mg/kg of body weight per day and can be administered in several different dosage units and more than once daily. For subcutaneous dosing, the therapeutic dosage can generally be from about 0.8 to 25 mg/kg of body weight per dose and can be administered in several different dosage units and more than once daily. For subcutaneous dosing, the therapeutic dosage can generally be from about 34 to about 677 mg/dose, and preferably from about 113 to about 508 mg/dose, or from about 0.5 to about 9.7 mg/Kg of body weight per dose and preferably from about 1.6 to about 7.3 mg/Kg of body weight per dose and can be administered in several different dosage units and more than once daily. For intraperitoneal dosing, the therapeutic dosage can generally be from about 17 to about 341 mg/dose, and preferably from about 57 to about 256 mg/dose, or from about 0.24 to about 4.88 mg/Kg of body weight per dose and preferably from about 0.81 to about 3.66 mg/Kg of body weight per dose and can be administered in several different dosage units and more than once daily. Higher dosages, on the order of about 2× to about 5× of the dosages described above, may be required for oral administration. The foregoing values represent projections based on animal studies, and may be readily adjusted based on the results of toxicology and efficacy studies to clinical requirements by one skilled in the Art.

For subcutaneous dosing, the therapeutic dosage can generally be from about 5 to 1500 mg/dose or 34 to about 677 mg/dose. Preferably the therapeutic dosage can generally be from about 113 to about 508 mg/dose or 48 to 300 mg/dose. The therapeutic dosage can generally be from about 0.8 to about 25 mg/kg, 0.5 to about 9.7 mg/kg, about 1.6 to about 7.3 mg/Kg, or about 10 to 30 mg/kg of body weight per dose and can be administered in several different dosage units and more than once daily. For intraperitoneal dosing, the therapeutic dosage can generally be from about 17 to about 341 mg/dose, and preferably from about 57 to about 256 mg/dose, or from about 0.24 to about 4.88 mg/Kg of body weight per dose and preferably from about 0.81 to about 3.66 mg/Kg of body weight per dose and can be administered in several different dosage units and more than once daily. Higher dosages, on the order of about 2× to about 5× of the dosages described above, may be required for oral administration. The foregoing values represent projections based on animal studies, and may be readily adjusted based on the results of toxicology and efficacy studies to clinical requirements by one skilled in the Art.

Methods of Use and Treatment

The present disclosure also provides methods of use of the compounds described herein in combination with an opioid and methods of treating a subject with the compounds described herein. In one aspect of the disclosure, the disclosure provides methods for potentiating the analgesic effects of an opioid. In another aspect, the disclosure provides methods for reducing the risk of developing an opioid dependency. In certain embodiments, the present disclosure provides methods for treating a subject with a clinical condition associated with Toll-like receptor glial activation. In some embodiments, the present disclosure provides methods for treating a subject suffering from or susceptible to neuropathic pain and/or nociceptive pain.

In one aspect of the disclosure, the disclosure provides methods for potentiating the analgesic effects of an opioid in a subject comprising administering to the subject an effective amount of a compound described herein. In some embodiments, a compound of Formula I is administered to the subject concurrently with an opioid compound. In certain embodiments, a compound of Formula I is administered to a subject after an opioid compound is administered to the subject. In some embodiments, a compound of Formula I is administered to a subject before an opioid compound is administered to a subject. In certain embodiments, a compound of Formula I is administered to a subject before an opioid is administered to a subject and also after the opioid compound is administered. In certain embodiments, a compound of Formula I is administered to a subject concurrently with an opioid, followed by additional administration of a compound of Formula 1 after the opioid compound has been administered. In some embodiments, a compound of Formula I is administered to a subject before and concurrently with an opioid compound. In some embodiments, a compound of Formula I is administered to the subject. In certain embodiments, a prodrug of a compound of Formula I is administered to the subject.

In another aspect of the disclosure, the disclosure provides methods for reducing the risk of developing an opioid dependency in a subject during opioid therapy, comprising the step of administering to the subject who is on opioid therapy an effective amount of a compound described herein. In some embodiments, a compound of Formula I is administered to the subject concurrently with an opioid compound. In other embodiments, a compound of Formula I is administered to the subject sequentially (e.g., before or after) with an opioid compound. In some embodiments, a compound of Formula I is administered to the subject. In certain embodiments, a prodrug of a compound of Formula I is administered to the subject.

Exemplary opioid compounds (e.g., the opioid being potentiated, the opioid being administered during opioid therapy, or the opioid a subject has a risk of developing a dependence on) include, but are not limited to Codeine, Morphine, Thebaine, Oripavine, Diacetylmorphine (morphine diacetate; heroin), Nicomorphine (morphine dinicotinate), Dipropanoylmorphine (morphine dipropionate), Diacetyldihydromorphine, Acetylpropionylmorphine, Desomorphine, Methyldesorphine, Dibenzoylmorphine, Dihydrocodeine, Ethylmorphine, Heterocodeine, Buprenorphine, Etorphine, Hydrocodone, Hydromorphone, Oxycodone, Oxymorphone, Fentanyl, Alphamethylfentanyl, Alfentanil, Sufentanil, Remifentanil, Carfentanyl, Ohmefentanyl, Pethidine (meperidine), Ketobemidone, MPPP, Allylprodine, Prodine, PEPAP, Promedol, Propoxyphene, Dextropropoxyphene, Dextromoramide, Bezitramide, Piritramide, Methadone, Dipipanone, Levomethadyl Acetate (LAAM), Difenoxin, Diphenoxylate, Loperamide, Dezocine, Pentazocine, Phenazo, Buprenorphine, Dihydroetorphine, Etorphine, Butorphanol, Nalbuphine, Levorphanol, Levomethorphan, Racemethorphan, Lefetamine, Menthol, Meptazinol, Mitragynine, Tilidine, Tramadol, Tapentadol, Eluxadoline, AP-237, and 7-Hydroxymitragynine.

In one aspect of the disclosure, the disclosure provides methods for treating a subject with a clinical condition associated with Toll-like receptor (TLR) glial activation comprising the step of administering to the subject an effective amount of a compound described herein. In some embodiments, a compound of Formula I is administered to the subject. In certain embodiments, a prodrug of a compound of Formula I is administered to the subject. In some embodiments, the Toll-like receptor is selected from the group consisting of TLR1, TLR2, TLR3, TLR4, TLR5, TLR6, TLR7, TLR8, TLR9, and TLR10. In certain embodiments, the Toll-like receptor is TLR-4. In some embodiments, the clinical condition comprises acute nociceptive pain, neuropathic pain, pain associated with neurological diseases, pain associated with neuronal damage, other pain subtypes/mixed pain states (e.g., pain caused by burns, osteoarthritis, chemotherapy, trauma) acute and repetitive opioid analgesia, the reward effects of drug abuse, chronic pain, or other pain associated with opioid dependency. In certain embodiments, the clinical condition comprises pain associated with a neurologic disease. In certain embodiments, the neurologic disease is selected from the group consisting of Alzheimer's disease, Parkinson's disease, amyotrophic lateral sclerosis, tauopathies, Huntington's disease, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. In some embodiments, the clinical condition comprises pain associated with neuronal damage.

In one aspect of the disclosure, the disclosure provides methods for treating a subject suffering from or susceptible to neuropathic pain, the method comprising administering to the subject an effective amount of the compound of claim 1. In certain embodiments, the neuropathic pain is due to multiple sclerosis. In some embodiments, the neuropathic pain is due to one or more of the following including spinal cord injury, multiple sclerosis, stroke, diabetes (e.g., peripheral diabetic neuropathy), sciatica, herpes zoster infection, HIV, neuralgia (e.g., post-herpetic neuralgia, trigeminal neuralgia), nutritional deficiencies, toxins, tumors, immune mediated disorders, physical trauma to a nerve trunk, cancer, chemotherapy (e.g., chemotherapy-induced pain, such as chemotherapy-induced peripheral neuropathy), radiation injury, invasive medical procedures, surgery, non-specific lower back pain, carpal tunnel syndrome, fibromyalgia, and pain resulting from an inflammatory condition (e.g., a chronic inflammatory condition). In certain embodiments, the neuropathic pain is due to cancer. In certain embodiments, the neuropathic pain is due to a neurologic disease. In certain embodiments, the neurologic disease is selected from the group consisting of Alzheimer's disease, Parkinson's disease, amyotrophic lateral sclerosis, tauopathies, Huntington's disease, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. In some embodiments, the neuropathic pain is due to neuronal damage.

In another aspect of the disclosure, the disclosure provides methods for treating a subject suffering from or susceptible to nociceptive pain, the method comprising administering to the subject an effective amount of the compound of claim 1. In certain embodiments, the nociceptive pain is associated with or derived from one or more of the following including bruises, burns, fractures, overuse or joint damage (e.g., arthritis, sprains), radiculopathy, pinched nerve, tumor, headache, laceration, surgery, and cancer. In some embodiments, the nociceptive pain is associated with or derived from joint damage, tumor, surgery, or cancer.

In some embodiments the effective amount is about 1500 mg. In some embodiments, the effective amount is about 1500 mg and is administered in 1 dose/day. In certain embodiments, the effective amount is about 1500 mg/dose and is administered twice, three times, or four times per day. In some embodiments, the effective amount per day is 6000 mg.

In some embodiments, the effective amount is from about 1 mg/day to about 1000 mg/day and is administered in one to several separate doses. In certain embodiments, the effective amount is from about 0 to 6000, 2.4 to 3000, 3 to 1000, 5 to 900, 10 to 800, 15 to 700, 20 to 600, or 25 to 550 mg/day and is administered in one to several separate doses. In some embodiments, the effective amount is from about 34 mg/day to about 510 mg/day and is administered in one to several separate doses. In certain embodiments, the effective amount is from about 68 to about 408 mg/day and is administered in one to several separate doses. In certain embodiments, the effective amount is about 75 to 350 mg/day, 90 to 300 mg/day, or 120 to 200 mg/day and is administered in one to several separate doses.

In certain embodiments, the effective amount is from about 48 mg/day to about 300 mg/day and is administered in one to several separate doses. In certain embodiments, the effective amount is from about 48 mg/day to about 300 mg/day and is administered in one dose. In certain embodiments, the effective amount is from about 48 mg/day to about 300 mg/day and is administered in two doses. In certain embodiments, the effective amount is from about 48 mg/day to about 300 mg/day and is administered in three doses. In certain embodiments, the effective amount is from about 48 mg/day to about 300 mg/day and is administered in four doses.

In certain embodiments, the effective amount is from about 48 mg/dose to about 300 mg/dose and is administered once to several times a day. In certain embodiments, the effective amount is from about 48 mg/dose to about 300 mg/dose and is administered in once per day. In certain embodiments, the effective amount is from about 48 mg/dose to about 300 mg/dose and is administered twice per day. In certain embodiments, the effective amount is from about 48 mg/dose to about 300 mg/dose and is administered three times per day. In certain embodiments, the effective amount is from about 48 mg/dose to about 300 mg/dose and is administered four time per day.

In certain embodiments, the effective amount is about 0.8 to 100 mg/kg of body weight per day and is administered in one to several separate doses. In certain embodiments, the effective amount is about 0.8 to 100 mg/kg of body weight per day and is administered in one dose. In certain embodiments, the effective amount is about 0.8 to 100 mg/kg of body weight per day and is administered in two doses. In certain embodiments, the effective amount is about 0.8 to 100 mg/kg of body weight per day and is administered in three doses. In certain embodiments, the effective amount is about 0.8 to 100 mg/kg of body weight per day and is administered in four doses.

In certain embodiments, the effective amount is about 0.8 to 25 mg/kg of body weight per day and is administered in one to several separate doses. In certain embodiments, the effective amount is about 0.8 to 25 mg/kg of body weight per day and is administered in one dose. In certain embodiments, the effective amount is about 0.8 to 25 mg/kg of body weight per day and is administered in two doses. In certain embodiments, the effective amount is about 0.8 to 25 mg/kg of body weight per day and is administered in three doses. In certain embodiments, the effective amount is about 0.8 to 25 mg/kg of body weight per day and is administered in four doses.

In some embodiments, the effective amount is about 0.5 to about 7.2 mg/kg of body weight per day and is administered in one to several separate doses. In some embodiments, the effective amount is about 1.0 to about 6 mg/kg of body weight per day and is administered in one to several separate doses. In certain embodiments, the effective amount is about 1.5 to 5.5, 2.0 to 5.0, or 2.5 to 4.5 mg/kg of body weight per day and is administered in one to several separate doses.

In certain embodiments, the effective amount is about 10 to about 30 mg/kg of body weight per day and is administered in one to several separate doses. In certain embodiments, the effective amount is about 10 to about 30 mg/kg of body weight per day and is administered in one dose. In certain embodiments, the effective amount is about 10 to about 30 mg/kg of body weight per day and is administered in two doses. In certain embodiments, the effective amount is about 10 to about 30 mg/kg of body weight per day and is administered in three doses. In certain embodiments, the effective amount is about 10 to about 30 mg/kg of body weight per day and is administered in four doses.

In certain embodiments, the effective amount is about 0.8 to about 5 mg/kg of body weight and is administered in one to several times per day. In certain embodiments, the effective amount is about 0.8 to about 5 mg/kg of body weight per dose and is administered once per day. In certain embodiments, the effective amount is about 0.8 to about 5 mg/kg of body weight per dose and is administered twice per day. In certain embodiments, the effective amount is about 0.8 to about 5 mg/kg of body weight per dose and is administered three times per day. In certain embodiments, the effective amount is about 0.8 to about 5 mg/kg of body weight per dose and is administered four times per day.

In certain embodiments, the effective amount is about 0.8 to about 5 mg/kg of body weight per day and is administered in one to several separate doses. In certain embodiments, the effective amount is about 0.8 to about 5 mg/kg of body weight per day and is administered in one dose. In certain embodiments, the effective amount is about 10.8 to about 5 mg/kg of body weight per day and is administered in two doses. In certain embodiments, the effective amount is about 0.8 to about 5 mg/kg of body weight per day and is administered in three doses. In certain embodiments, the effective amount is about 0.8 to about 5 mg/kg of body weight per day and is administered in four doses.

In some embodiments, the effective amount is administered in one dose per day. In certain embodiments, the effective amount is administered in two doses per day. In some embodiments, the effective amount is administered in three or four doses per day. In some embodiments, each dose is the same. In other embodiments, each dose is different. In certain embodiments, each sequential dose increases. In certain embodiments, each sequential dose decreases. In certain embodiments, dosing occurs daily and continues for many days. In certain embodiments, dosing occurs daily and continues for many months. In certain embodiments, dosing occurs daily and for many years. In certain embodiments, dosing occurs almost daily and continues for many days. In certain embodiments, dosing occurs almost daily and continues for many months. In certain embodiments, dosing occurs almost daily and for many years. In some embodiments, a compound of Formula I is administered to the subject. In certain embodiments, a prodrug of a compound of Formula I is administered to the subject.

Kits

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for potentiating the analgesic effects of an opioid in a subject. In certain embodiments, the kits are useful for reducing the risk of developing an opioid dependency in a subject. In certain embodiments, the kits are useful for treating a subject with a clinical condition associated with Toll-like receptor glial activation. In certain embodiments, the kits are useful for treating a subject suffering from or susceptible to neuropathic pain. In some embodiments, the kits are useful for treating a subject suffering from or susceptible to neuropathic pain caused by or associated with spinal cord injury, multiple sclerosis, stroke, diabetes, sciatica, herpes zoster infection, HIV, neuralgia, nutritional deficiencies, toxins, tumors, immune mediated disorders, physical trauma to a nerve trunk, cancer, chemotherapy, radiation injury, invasive medical procedures, surgery, non-specific lower back pain, carpal tunnel syndrome, fibrormyalgia, and a chronic inflammatory condition. In some embodiments, the kits are useful for treating a subject suffering from or susceptible to neuropathic pain caused by or associated with multiple sclerosis. In some embodiments, the kits are useful for treating a subject suffering from or susceptible to neuropathic pain caused by or associated with cancer. In some embodiments, the kits are useful for treating a subject suffering from or susceptible to neuropathic pain caused by or associated with chemotherapy. In certain embodiments, the kits are useful for treating a subject suffering from or susceptible to nociceptive pain.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information.

In certain embodiments, the kits and instructions provide for potentiating the analgesic effects of an opioid in a subject. In certain embodiments, the kits and instructions provide for reducing the risk of developing an opioid dependency in a subject. In certain embodiments, the kits and instructions provide for treating a subject with a clinical condition associated with Toll-like receptor glial activation. In certain embodiments, the kits and instructions provide for treating a subject suffering from or susceptible to neuropathic pain. In certain embodiments, the kits and instructions provide for treating a subject suffering from or susceptible to neuropathic pain caused by or associated with spinal cord injury, multiple sclerosis, stroke, diabetes, sciatica, herpes zoster infection, HIV, neuralgia, nutritional deficiencies, toxins, tumors, immune mediated disorders, physical trauma to a nerve trunk, cancer, chemotherapy, radiation injury, invasive medical procedures, surgery, non-specific lower back pain, carpal tunnel syndrome, fibromyalgia, and a chronic inflamatory condition. In certain embodiments, the kits and instructions provide for treating a subject suffering from or susceptible to neuropathic pain caused by or associated with multiple sclerosis. In certain embodiments, the kits and instructions provide for treating a subject suffering from or susceptible to neuropathic pain caused by or associated with cancer. In certain embodiments, the kits and instructions provide for treating a subject suffering from or susceptible to neuropathic pain caused by or associated with chemotherapy. In certain embodiments, the kits and instructions provide for treating a subject suffering from or susceptible to nociceptive pain. A kit described herein may include one or more additional pharmaceutical agents described herein as a separate composition.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Synthesis

The synthesis of the compounds disclosed herein was carried out as described in the Detailed Description (vide supra). FIGS. 3A and 3B show exemplary synthetic methodologies for preparing select halogenated morphians of Formula I. In these examples, the halogen is fluorine and the key chemistry involves fluorination of the 6-keto functionality of the (+)-morphians. FIG. 4 shows a synthesis scheme for XT-203. The compounds disclosed in Table 2 were synthesized utilizing analogous routes. The corresponding characterization data appears below in Table 2.

TABLE 2

Synthesis Routes and Characterization

Figure 17:
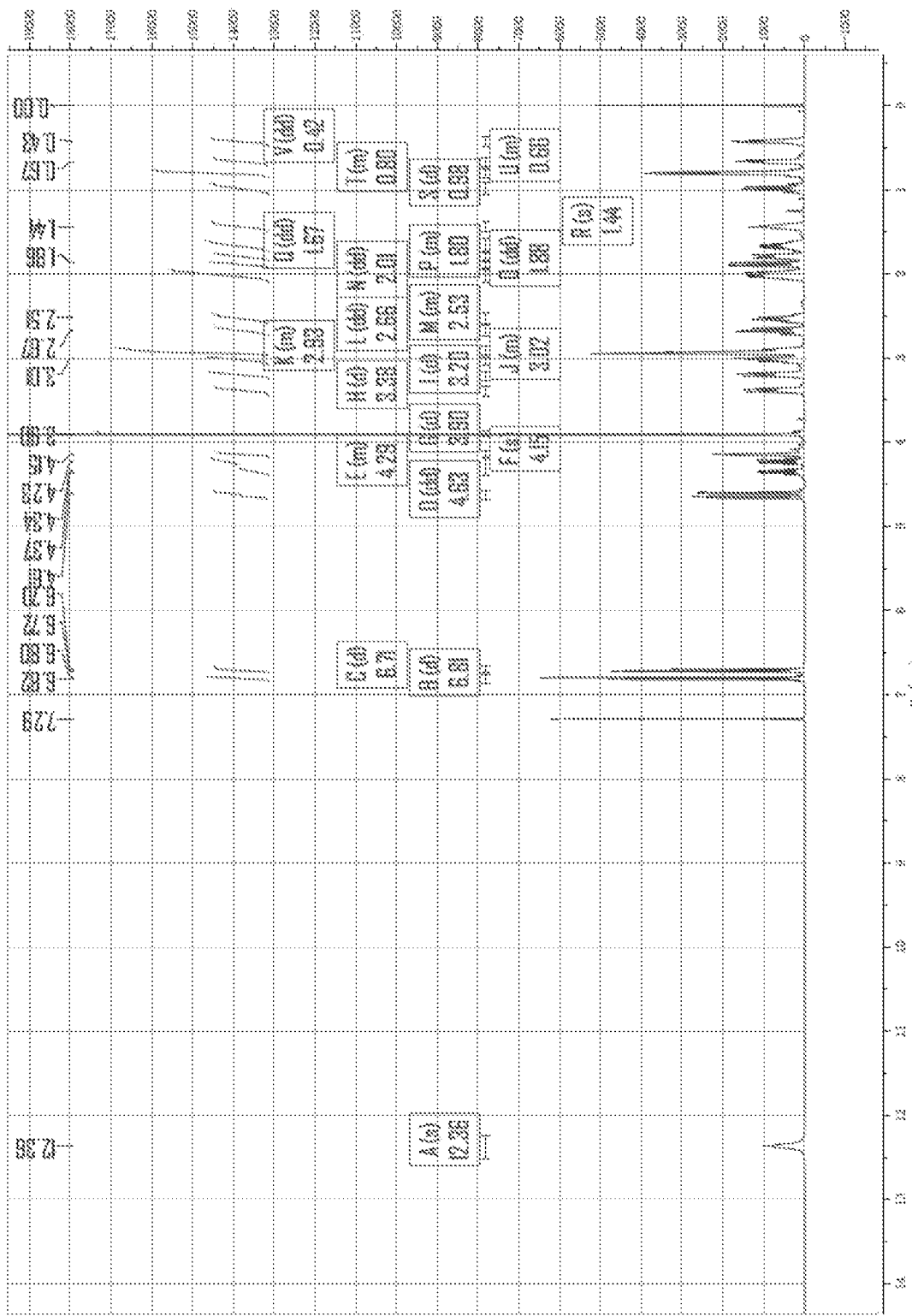
FIG. 17 shows a $^1$H NMR spectrum of XT-203 in $CDCl_3$.
Figure 18:
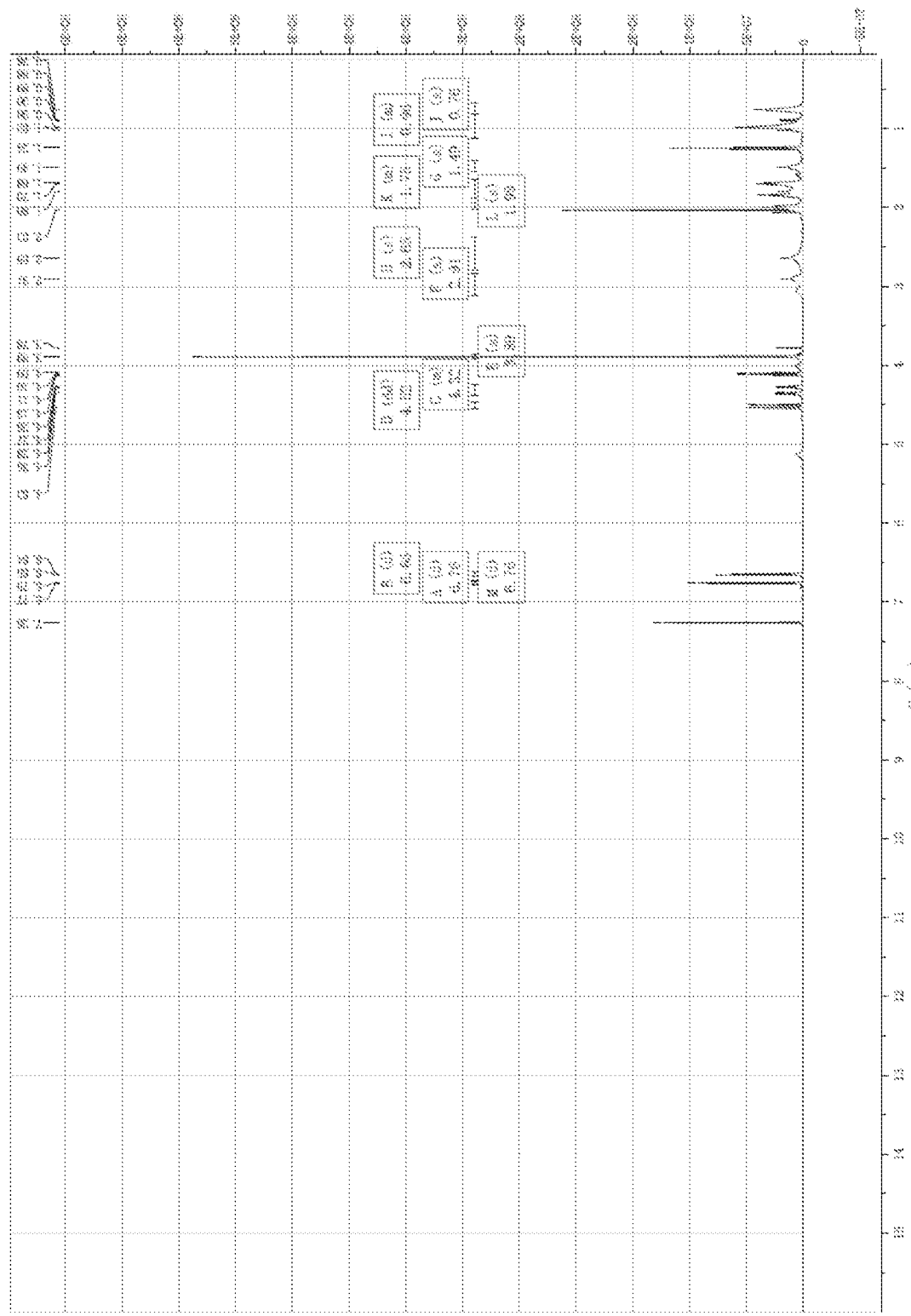
FIG. 18 shows a $^1$H NMR spectrum of XT-206 in $CDCl_3$.
Figure 19:
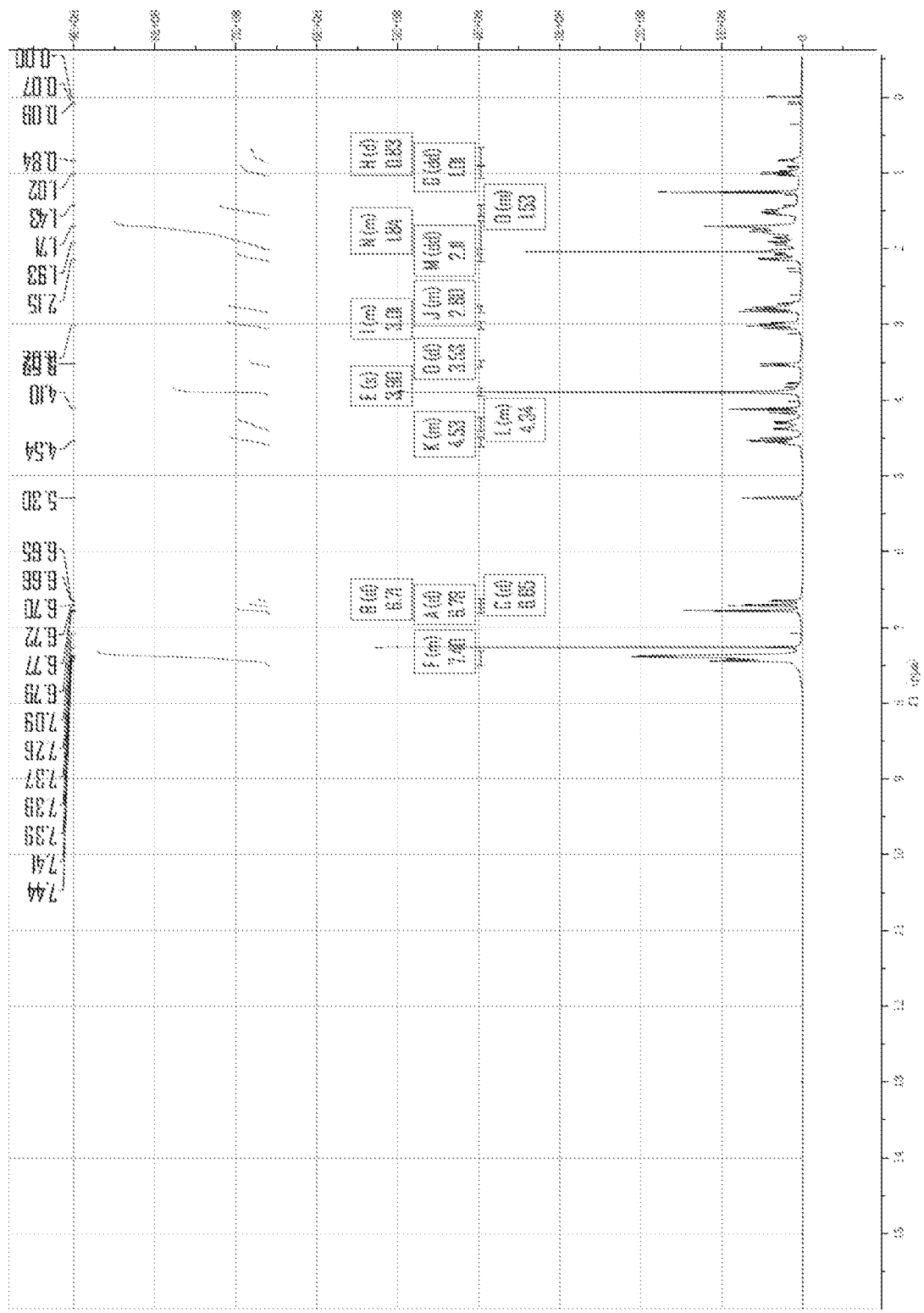
FIG. 19 shows a $^1$H NMR spectrum of XT-207 in $CDCl_3$.
Figure 20:
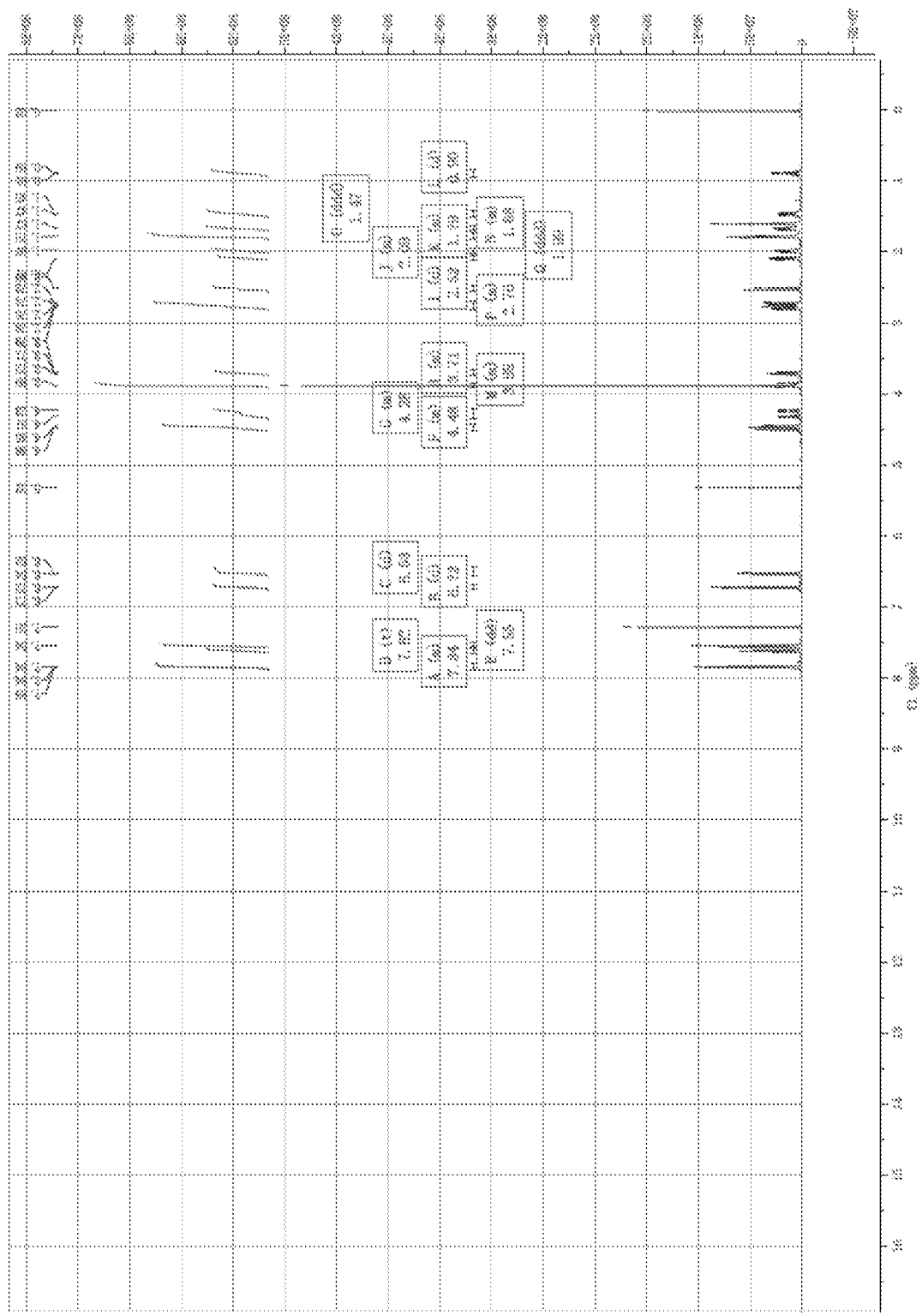
FIG. 20 shows a $^1$H NMR spectrum of XT-208 in $CDCl_3$.
Figure 21:
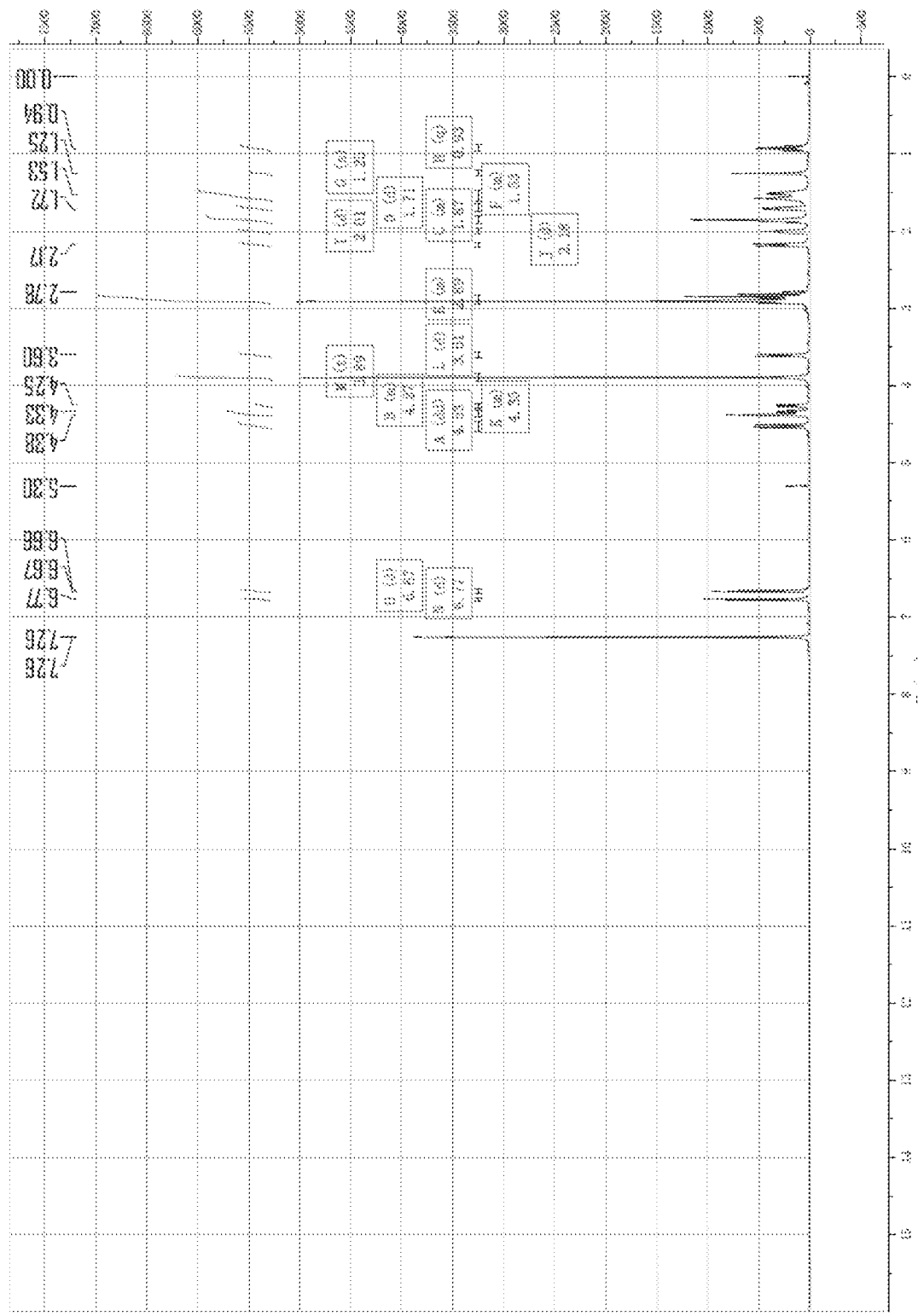
FIG. 21 shows a $^1$H NMR spectrum of XT-209 in $CDCl_3$.
Figure 22:
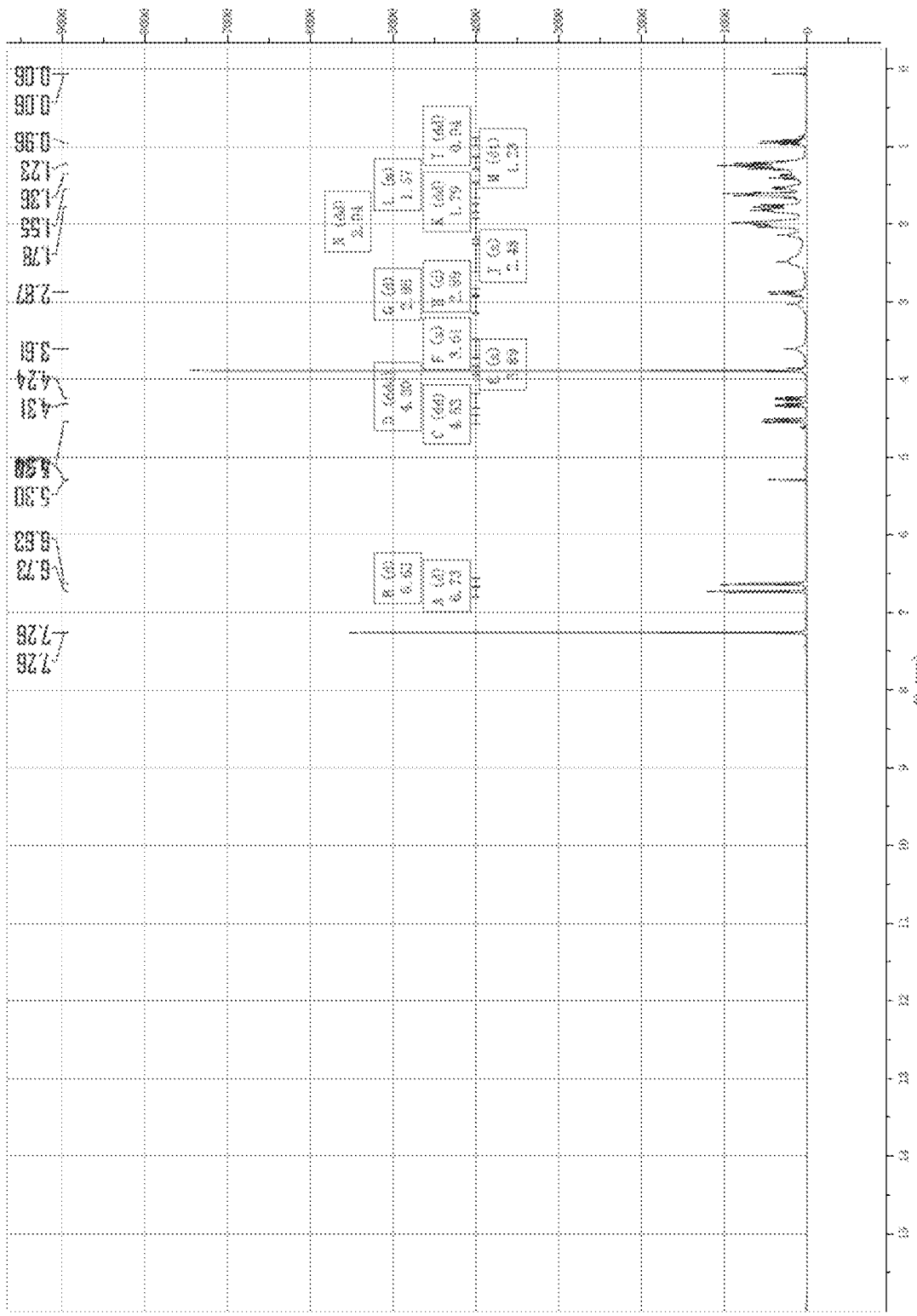
FIG. 22 shows a $^1$H NMR spectrum of XT-210 in $CDCl_3$.

| Name | Structure | Spectrum | Characterization Data |
|---|---|---|---|
| XT-203 | 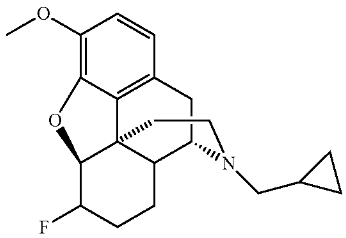 [SMILES: COc1ccc2c3c1O[C@@H]1C(F)CCC4[C@H](C2)N(CC2CC2)CC[C@]341] | FIG. 17 | $^1$H NMR (600 MHz, CDCl$_3$) δ 12.36 (s), 6.81 (d, J = 8.3 Hz), 6.71 (d, J = 8.3 Hz), 4.63 (d, J = 20.3, 6.2 Hz), 4.39-1.19 (m), 4.15 (s), 3.90 (d, J = 3.5 Hz), 3.38 (d, J = 11.7 Hz), 3.20 (d, J = 11.9 Hz), 3.08-2.99 (m), 2.97-2.85 (m), 2.66 (dd, J = 13.2, 4.2 Hz), 2.60-2.46 (m), 2.01 (dd, J = 13.3, 9.7 Hz), 1.88 (dd, J = 13.3, 2.6 Hz), 1.84-1.75 (m), 1.67 (dd, J = 12.7, 7.0 Hz), 1.44 (s), 0.98 (d, J = 12.9 Hz), 0.86-0.76 (m), 0.73-0.62 (m), 0.42 (dd, J = 8.8, 3.9 Hz). LCMS m/z: 344.1 [M + 1]. |
| XT-206 | 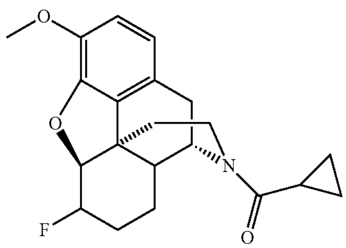 [SMILES: COc1ccc2c3c1O[C@@H]1C(F)CCC4[C@H](C2)N(C(=O)C2CC2)CC[C@]341] | FIG. 18 | $^1$H NMR (600 MHz, CDCl$_3$) δ 6.76 (d, J = 8.2 Hz), 6.76 (d, J = 8.2 Hz), 6.65 (d, J = 8.2 Hz), 4.52 (dd, J = 20.7, 6.1 Hz), 4.37-4.24 (m), 3.89 (s), 2.91 (s), 2.65 (s), 1.99 (s), 1.88-1.64 (m), 1.49 (s), 1.12-0.81 (m), 0.76 (s). LCMS m/z: 358.2 [M + 1]. |
| XT-207 | 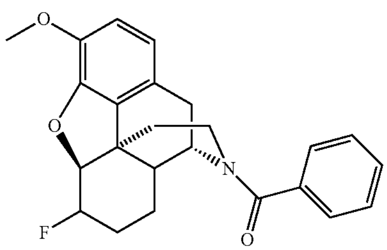 [SMILES: COc1ccc2c3c1O[C@@H]1C(F)CCC4[C@H](C2)N(C(=O)c2ccccc2)CC[C@]341] | FIG. 19 | $^1$H NMR (600 MHz, CDCl$_3$) δ 7.51-7.31 (m), 6.78 (d, J = 8.1 Hz), 6.71 (d, J = 8.1 Hz), 6.65 (d, J = 7.8 Hz), 4.61-4.49 (m), 4.41-4.24 (m), 3.90 (s), 3.53 (d, J = 14.0 Hz), 3.07-2.97 (m), 2.85-2.75 (m), 2.11 (dd, J = 35.3, 11.9 Hz), 2.02-1.64 (m), 1.57-1.43 (m), 1.01 (dd, J = 25.5, 12.8 Hz), 0.83 (d, J = 12.4 Hz). LCMS m/z: 394.1 [M + 1]. |
| XT-208 | 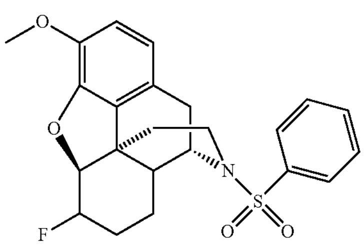 [SMILES: COc1ccc2c3c1O[C@@H]1C(F)CCC4[C@H](C2)N(S(=O)(=O)c2ccccc2)CC[C@]341] | FIG. 20 | $^1$H NMR (600 MHz, CDCl$_3$) δ 7.88-7.79 (m), 7.62 (t, J = 7.4 Hz), 7.55 (dd, J = 10.5, 4.8 Hz), 6.72 (d, J = 8.2 Hz), 6.53 (d, J = 8.2 Hz), 4.52-4.43 (m), 4.36-4.21 (m), 3.91-3.84 (m), 3.73-3.65 (m), 2.81-2.69 (m), 2.52 (d, J = 18.4 Hz), 2.11-2.05 (m), 1.99 (ddd, J = 9.7, 5.1, 2.4 Hz), 1.83-1.73 (m), 1.70-1.63 (m), 1.47 (ddd, J = 12.6, 7.1, 2.7 Hz), 0.90 (d, J = 12.9 Hz). LCMS m/z: 430.1 [M + 1]. |
| XT-209 | 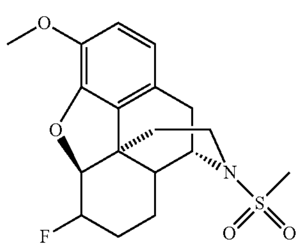 | FIG. 21 | $^1$H NMR (600 MHz, CDCl$_3$) δ 6.77 (d, J = 8.2 Hz), 6.67 (d, J = 8.1 Hz), 4.53 (dd, J = 20.6, 5.9 Hz), 4.41-4.33 (m), 4.29-4.23 (m), 3.89 (t, J = 6.1 Hz), 3.61 (d, J = 11.5 Hz), 2.95-2.84 (m), 2.18 (d, J = 12.6 Hz), 2.01 (d, J = 5.2 Hz), 1.91-1.80 (m), 1.71 (d, J = 13.4 Hz), 1.62-1.47 (m), 1.25 (s), 0.93 (q, J = 13.3 Hz). LCMS m/z: 368.1 [M + 1]. |
| XT-210 | 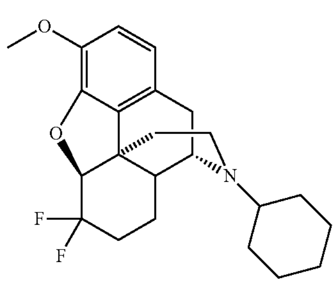 [SMILES: COc1ccc2c3c1O[C@@H]1C(F)(F)CCC4[C@H](C2)N(C2CCCCC2)CC[C@]341] | FIG. 22 | $^1$H NMR (600 MHz, CDCl$_3$) δ 6.73 (d, J = 8.2 Hz), 6.63 (d, J = 8.1 Hz), 4.53 (dd, J = 20.8, 5.9 Hz), 4.30 (ddd, J = 48.9, 12.1, 5.9 Hz), 3.89 (s), 3.61 (s), 2.98 (d, J = 57.3 Hz), 2.89 (d, J = 18.3 Hz), 2.48 (s), 2.04 (dd, J = 55.7, 44.5 Hz), 1.79 (dd, J = 29.5, 13.0 Hz), 1.66-1.47 (m), 1.23 (dt, J = 24.2, 12.7 Hz), 0.94 (dd, J = 25.9, 12.8 Hz). LCMS m/z: 372.2 [M + 1]. |

TABLE 2-continued

Synthesis Routes and Characterization

Figure 23:
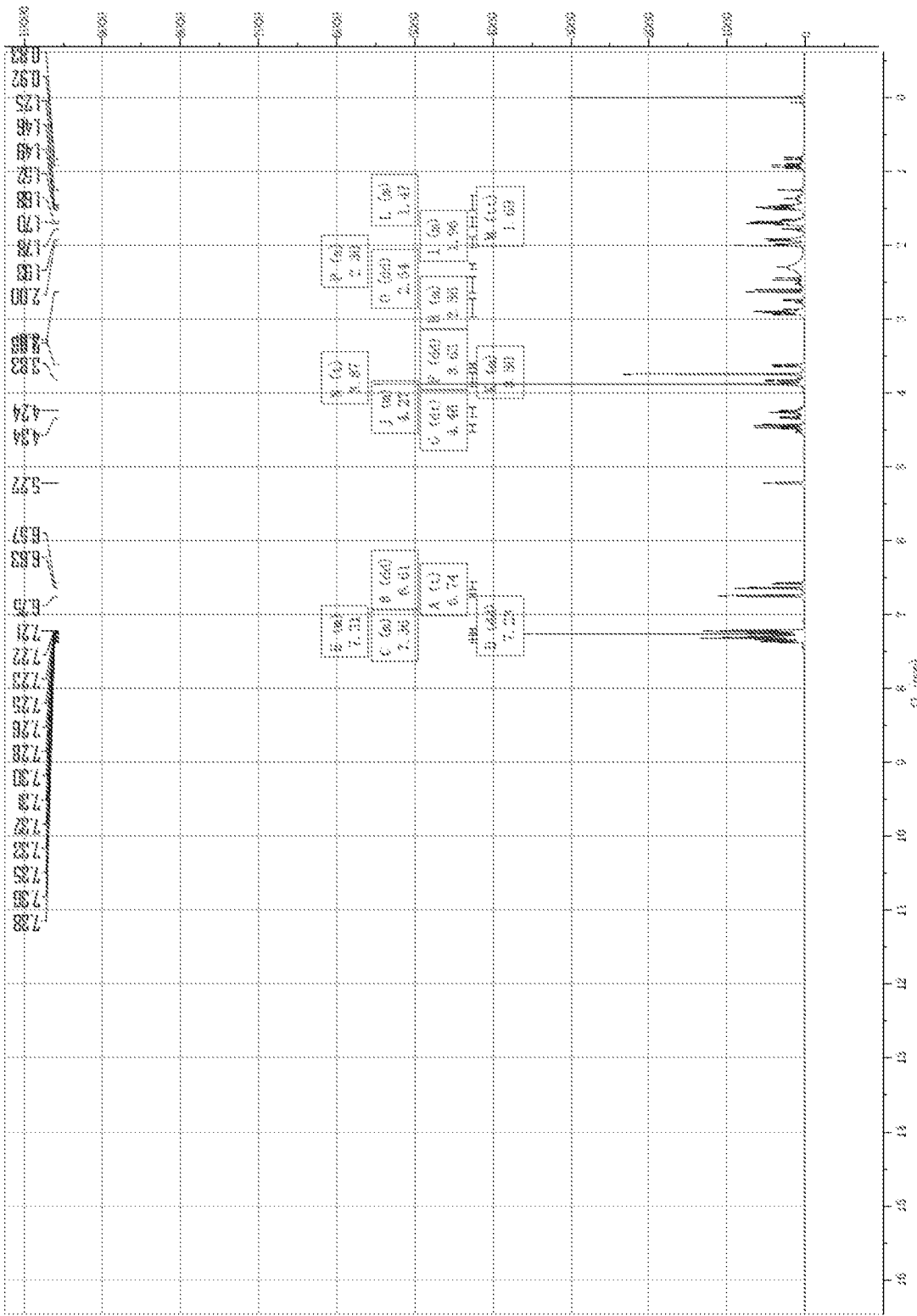
FIG. 23 shows a $^1$H NMR spectrum of XT-211 in $CDCl_3$.
Figure 24:
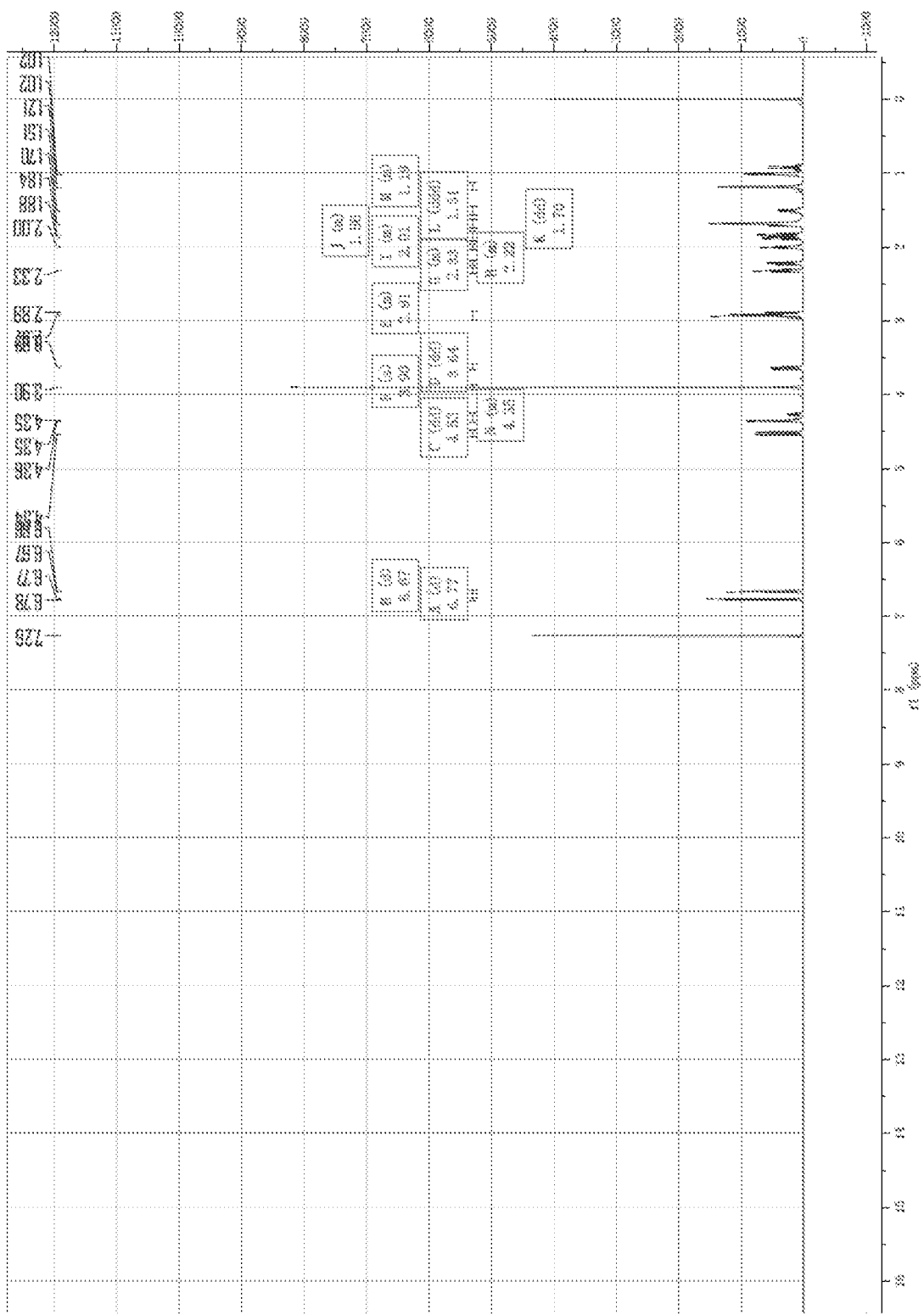
FIG. 24 shows a $^1$H NMR spectrum of XT-212 in $CDCl_3$.
Figure 25:
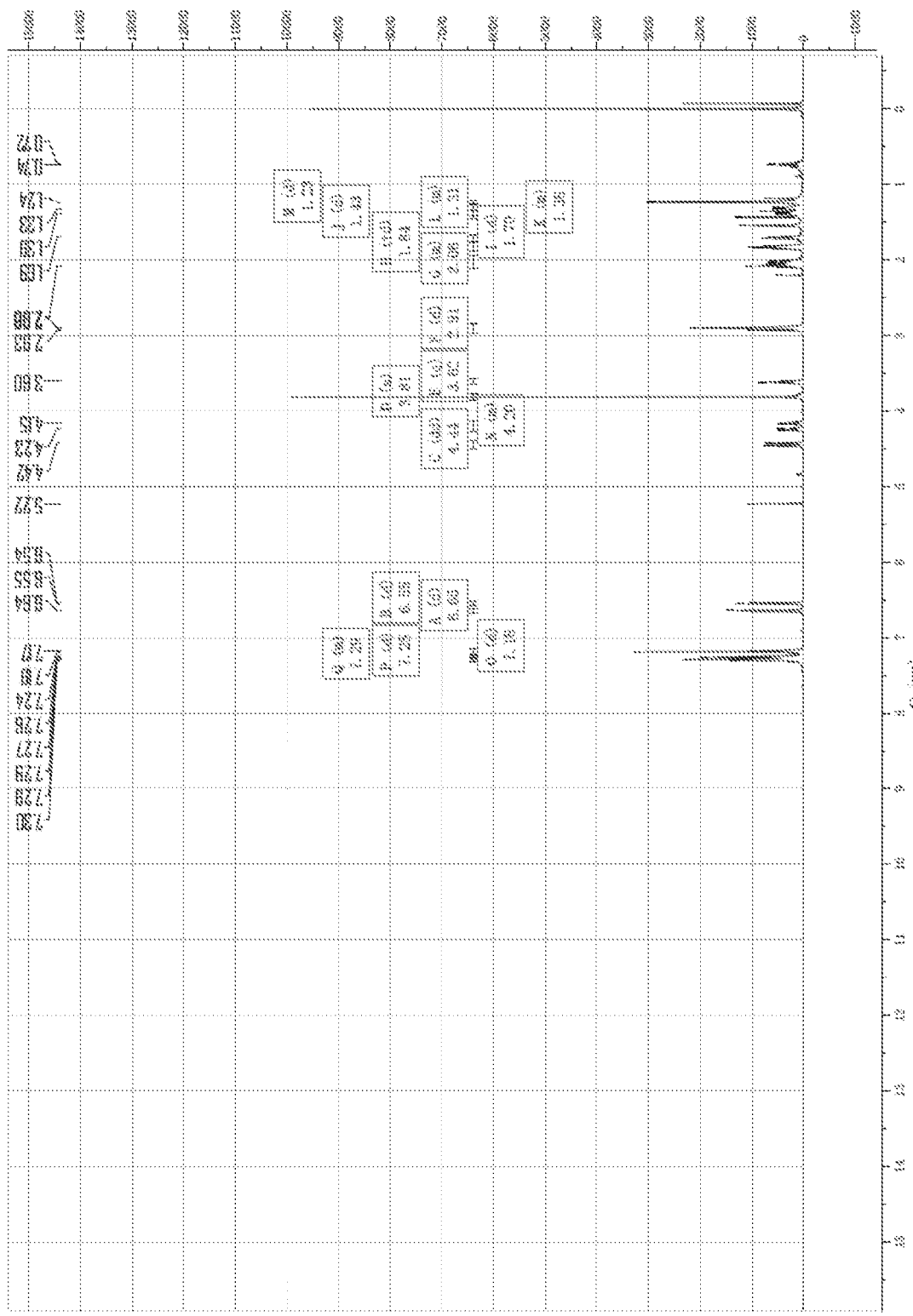
FIG. 25 shows a $^1$H NMR spectrum of XT-213 in $CDCl_3$.
Figure 26:
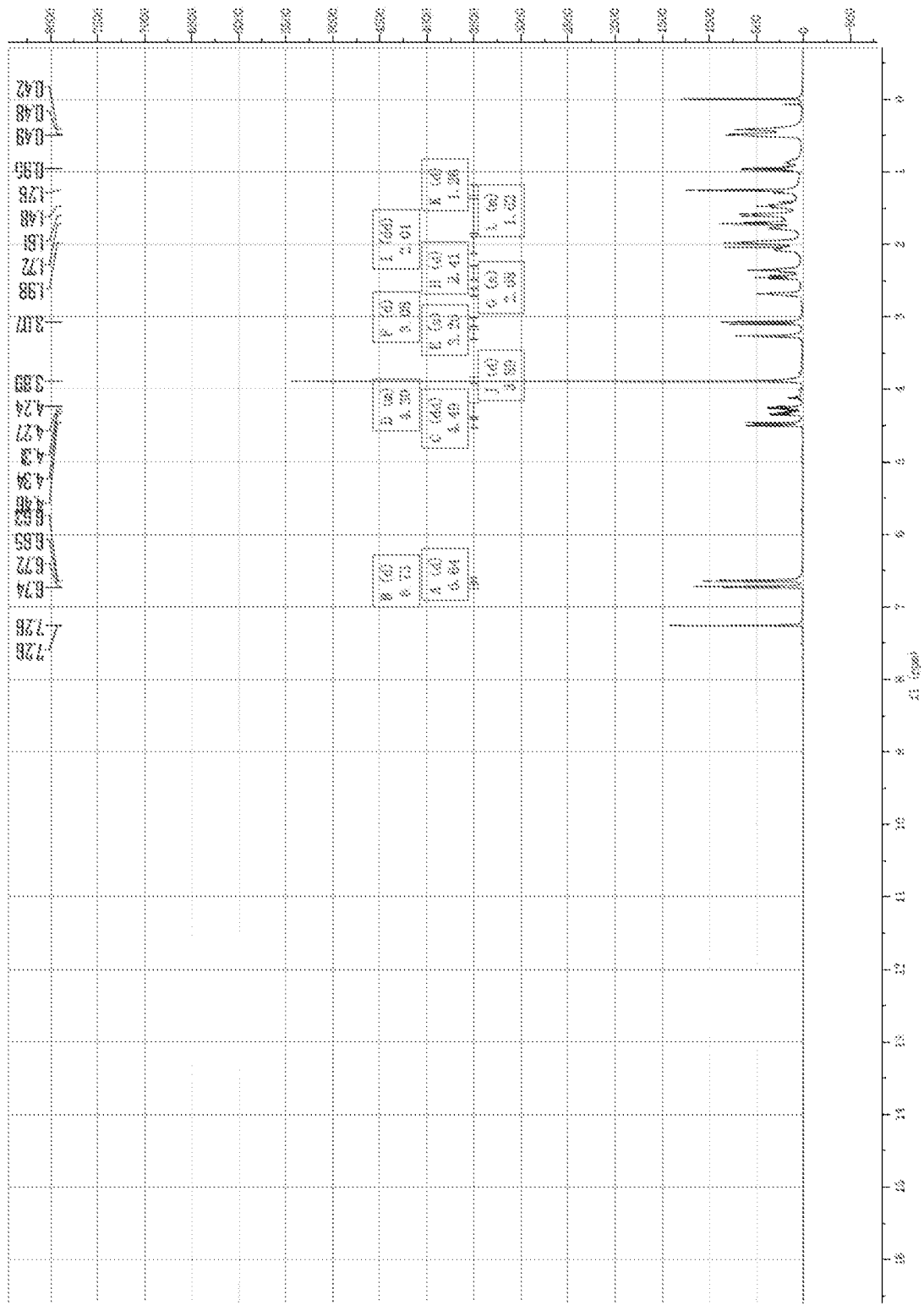
FIG. 26 shows a $^1$H NMR spectrum of XT-214 in $CDCl_3$.
Figure 27:
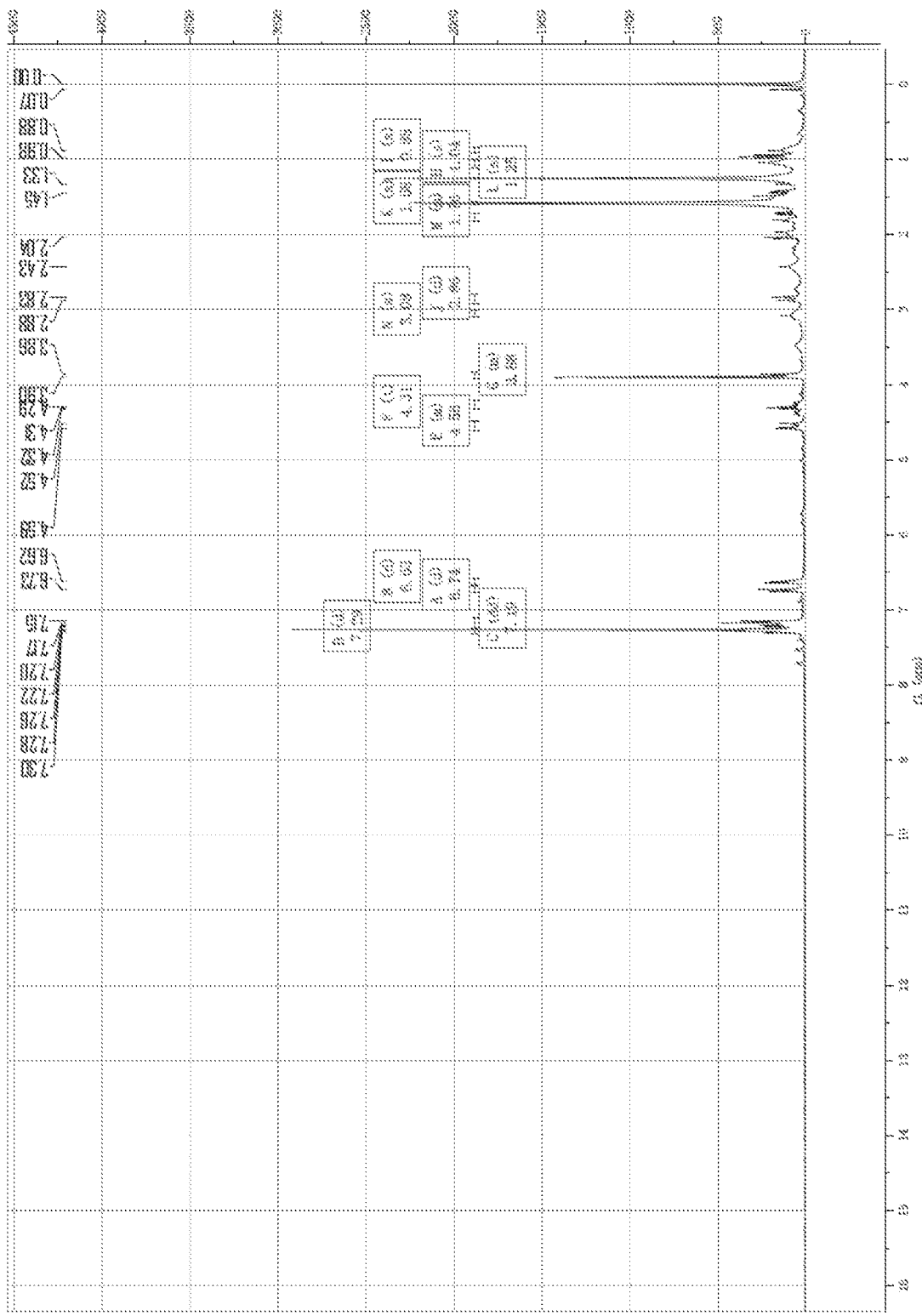
FIG. 27 shows a $^1$H NMR spectrum of XT-215 in $CDCl_3$.

| Name | Structure | Spectrum | Characterization Data |
|---|---|---|---|
| XT-211 | 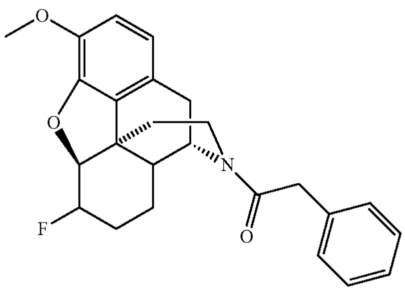 [SMILES: COc1ccc2c3c1O[C@@H]1C(F)CCC4[C@H](C2)N(C(=O)Cc2ccccc2)CC[C@]341] | FIG. 23 | $^1$H NMR (600 MHz, CDCl$_3$) 7.38-7.34 (m), 7.34-7.28 (m), 7.23 (dd, J = 13.5, 7.6 Hz), 6.74 (t, J = 7.2 Hz), 6.61 (dd, J = 38.5, 8.2 Hz), 4.46 (dt, J = 20.7, 6.2 Hz), 4.33-4.19 (m), 3.87 (t, J = 5.6 Hz), 3.85-3.73 (m), 3.63 (dd, J = 13.9, 4.5 Hz), 2.97-2.72 (m), 2.54 (dd, J = 95.6, 18.3 Hz), 2.30 (s), 2.04-1.88 (m), 1.69 (tt, J = 15.3, 7.5 Hz), 1.53-1.33 (m). LCMS m/z: 408.2 [M + 1]. |
| XT-212 | 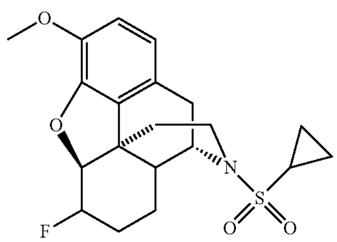 [SMILES: COc1ccc2c3c1O[C@@H]1C(F)CCC4[C@H](C2)N(S(=O)(=O)C2CC2)CC[C@]341] | FIG. 24 | 1H NMR (600 MHz, CDCl3) δ 6.77 (d, J = 8.2 Hz), 6.67 (d, J = 8.2 Hz), 4.53 (dd, J = 20.6, 6.1 Hz), 4.38-4.24 (m), 3.90 (s), 3.64 (dd, J = 13.3, 4.6 Hz), 2.98-2.88 (m), 2.35-2.29 (m), 2.26-2.19 (m), 2.04-1.97 (m), 1.91-1.79 (m), 1.70 (dd, J = 12.4, 8.4 Hz), 1.51 (ddd, J = 12.6, 7.1, 2.8 Hz), 1.23-1.13 (m). LCMS m/z: 394.1 [M + 1]. |
| XT-213 | 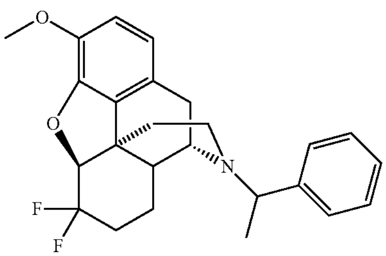 [SMILES: COc1ccc2c3c1O[C@@H]1C(F)(F)CCC4[C@H](C2)N(C(C)c2ccccc2)CC[C@]341] | FIG. 25 | $^1$H NMR (600 MHz, CDCl$_3$) δ 7.32-7.28 (m), 7.25 (d, J = 7.6 Hz), 7.18 (d, J = 7.3 Hz), 6.65 (d, J = 8.1 Hz), 6.55 (d, J = 8.1 Hz), 4.44 (dd, J = 21.0, 6.0 Hz), 4.27-1.13 (m), 3.81 (s), 3.62 (q, J = 6.3 Hz), 2.91 (d, J = 18.0 Hz), 2.12-1.95 (m), 1.84 (td, J = 12.2, 4.8 Hz), 1.70 (d, J = 11.9 Hz), 1.43 (d, J = 6.5 Hz), 1.41-1.34 (m), 1.33-1.27 (m), 1.23 (d, J = 6.4 Hz). LCMS m/z: 394.2 [M + 1]. |
| XT-214 | 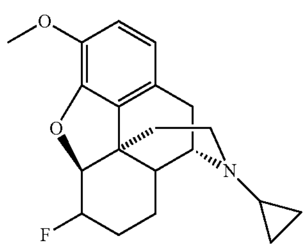 [SMILES: COc1ccc2c3c1O[C@@H]1C(F)CCC4[C@H](C2)N(C2CC2)CC[C@]341] | FIG. 26 | $^1$H NMR (600 MHz, CDCl$_3$) δ 6.73 (d, J = 8.1 Hz), 6.64 (d, J = 8.1 Hz), 4.49 (dd, J = 21.0, 5.9 Hz), 4.38-4.19 (m), 3.89 (d, J = 1.3 Hz), 3.26 (s), 3.08 (d, J = 18.2 Hz), 2.68 (s), 2.41 (d, J = 65.0 Hz), 2.01 (dd, J = 41.3, 6.6 Hz), 1.85-1.38 (m), 1.26 (d, J = 7.4 Hz). LCMS m/z: 330.1 [M + 1]. |
| XT-215 | 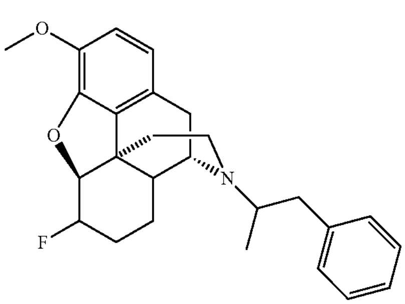 [SMILES: COc1ccc2c3c1O[C@@H]1C(F)CCC4[C@H](C2)N(C(C)Cc2ccccc2)CC[C@]341] | FIG. 27 | $^1$H NMR (600 MHz, CDCl$_3$) δ 7.29 (d, J = 7.2 Hz), 7.19 (dd, J = 20.2, 7.2 Hz), 6.74 (d, J = 8.2 Hz), 6.63 (d, J = 7.8 Hz), 4.61-4.48 (m), 4.31 (t, J = 6.7 Hz), 3.93-3.83 (m), 3.08 (s), 2.86 (d, J = 18.0 Hz), 1.82-1.72 (m), 1.58 (s), 1.25 (s), 1.04 (s), 0.88 (s). LCMS m/z: 408.2 [M + 1]. |

TABLE 2-continued

Synthesis Routes and Characterization

Figure 28:
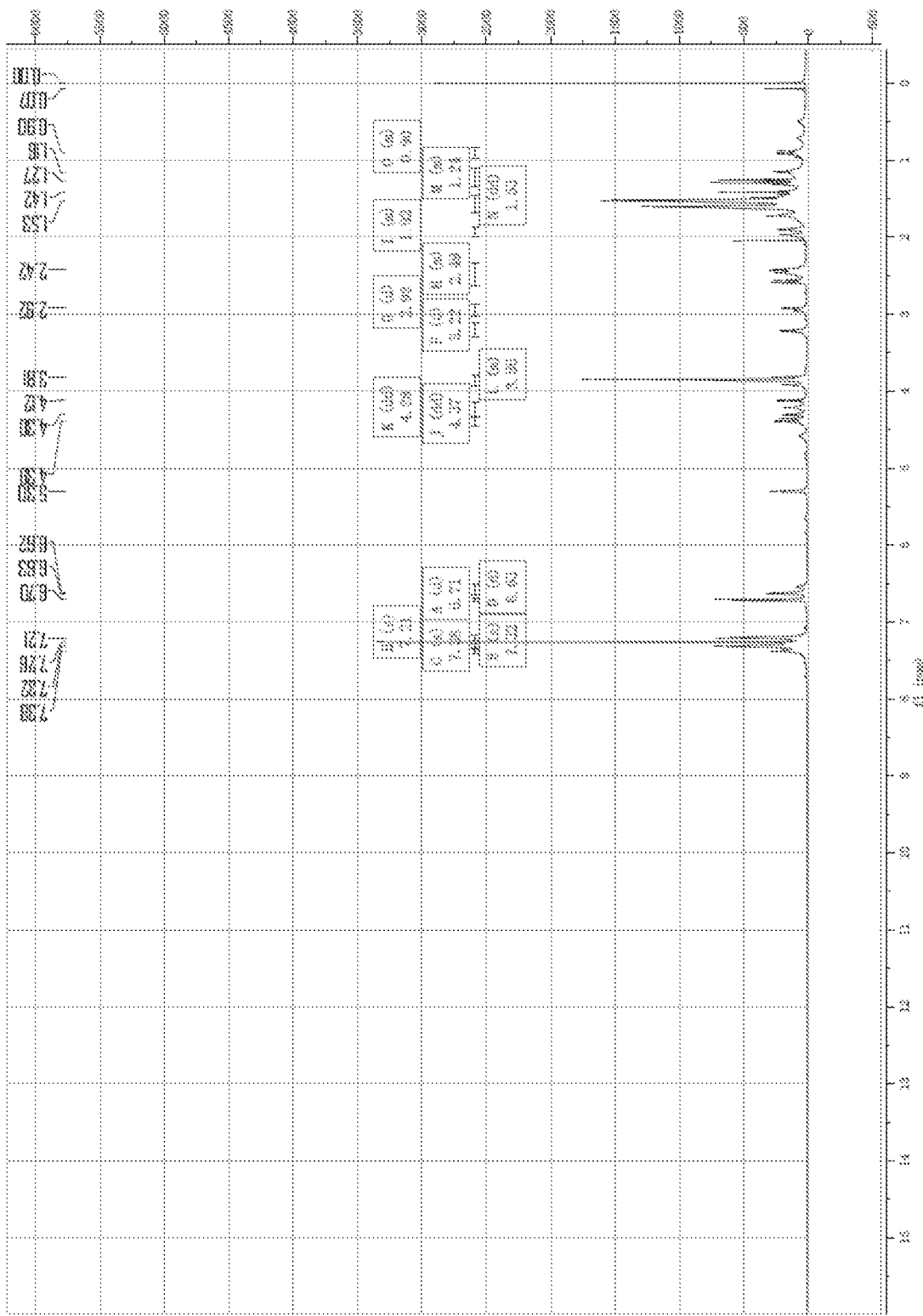
FIG. 28 shows a $^1$H NMR spectrum of XT-216 in $CDCl_3$.
Figure 29:
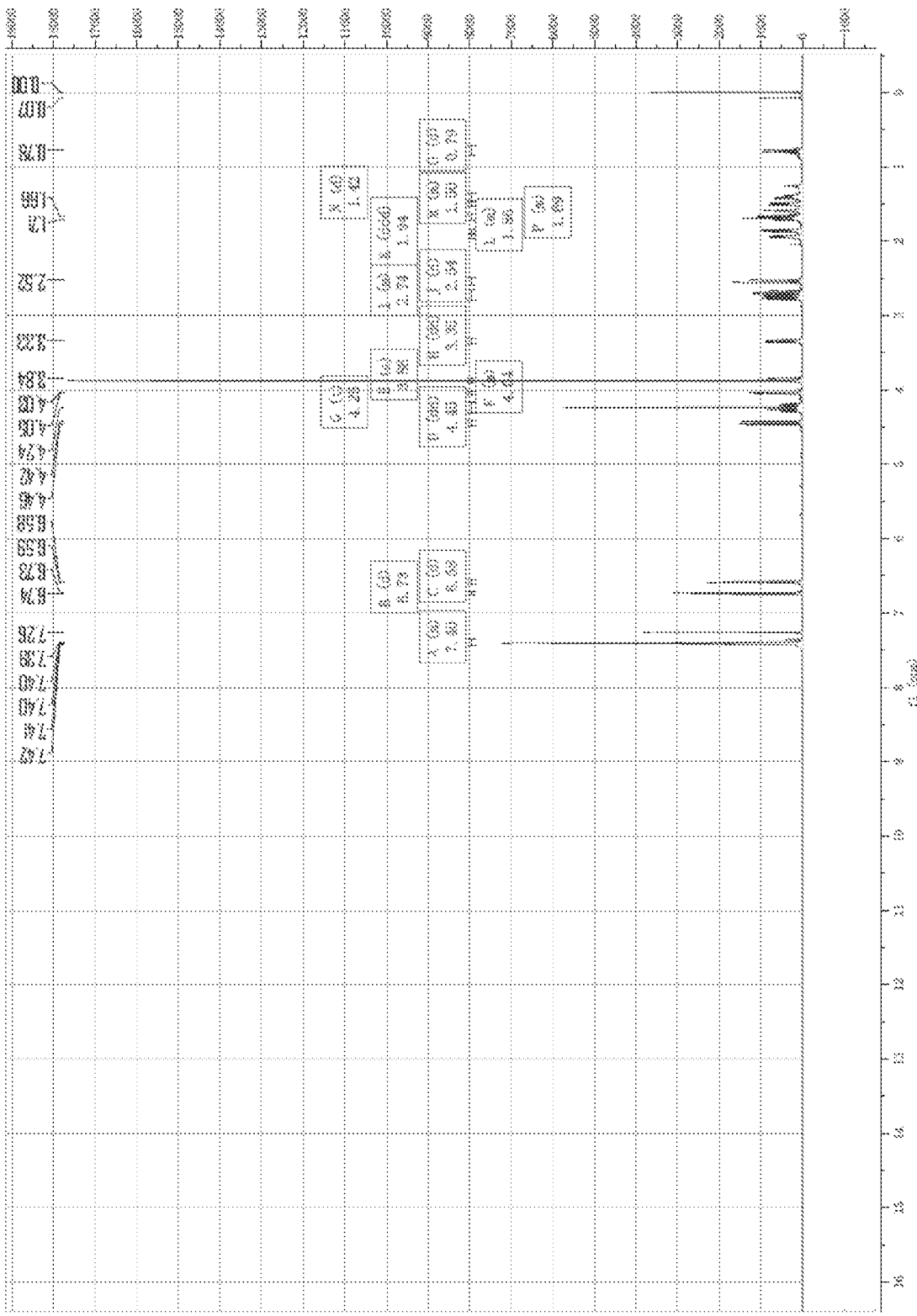
FIG. 29 shows a $^1$H NMR spectrum of XT-217 in $CDCl_3$.

| Name | Structure | Spectrum | Characterization Data |
|---|---|---|---|
| XT-216 | 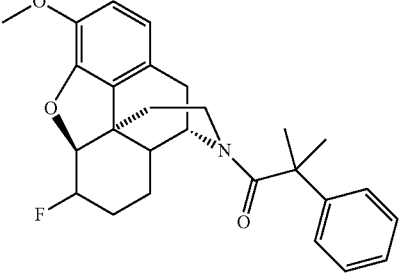 | FIG. 28 | $^1$H NMR (600 MHz, CDCl$_3$) δ 7.38 (s), 7.32 (s), 7.21 (s), 6.71 (d, J = 8.1 Hz), 6.63 (d, J = 7.9 Hz), 4.37 (dd, J = 20.7, 5.0 Hz), 4.28 (dd, J = 35.3, 28.7 Hz), 3.93-3.79 (m), 3.22 (d, J = 14.5 Hz), 2.92 (d, J = 4.5 Hz), 2.63-2.34 (m), 2.00-1.87 (m), 1.53 (dd, J = 40.1, 31.1 Hz), 1.34-1.10 (m), 0.97-0.84 (m). LCMS m/z: 436.2 [M + 1]. |
| XT-217 | 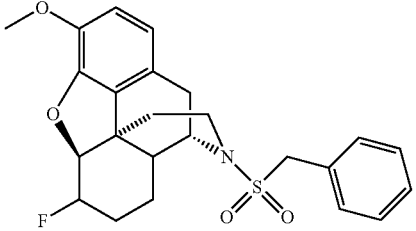 [SMILES: COc1ccc2c3c1O[C@@H]1C(F)CCC4[C@H](C2)N(S(=O)(=O)Cc2ccccc2)CC[C@]341] | FIG. 29 | $^1$H NMR (600 MHz, CDCl$_3$) δ 7.44-7.35 (m), 6.73 (d, J = 8.2 Hz), 6.58 (d, J = 8.2 Hz), 4.45 (dd, J = 20.7, 6.1 Hz), 4.25 (t, J = 7.7 Hz), 4.06-4.01 (m), 3.88 (s), 3.35 (dd, J = 13.6, 4.4 Hz), 2.79-2.65 (m), 2.54 (d, J = 18.4 Hz), 1.94 (ddd, J = 9.6, 5.1, 2.4 Hz), 1.89-1.83 (m), 1.73-1.63 (m), 1.53-1.47 (m), 1.42 (d, J = 2.7 Hz), 0.79 (d, J = 13.0 Hz). LCMS m/z: 444.1 [M + 1]. |

General Materials and Methods

Pathogen-free adult male Sprague-Dawley rats (300-375 g; Harlan Labs, Madison, Wis.) were used in all experiments. Rats were housed in temperature (23+/−3° C.) and light (12 hour:12 hour, light:dark cycle; lights on at 0700) controlled rooms with standard rodent chow and water available ad libitum.

Example 1

Chronic Constriction Injury (CCI) model: Neuropathic pain was induced using the CCI model of partial sciatic nerve injury (see, e.g., Bennett and Xie, Pain, 132:273-80 (2007)). CCI was performed at the mid-thigh level of the left hindleg as previously described in Milligan, et al., Eur. J. Neuroscience, 20:2294-2302 (2004). In brief, four sterile chromic gut sutures (cuticular 4-0 chromic gut, FS-2; Ethicon, Somerville, N.J., USA) were loosely tied around the gently isolated sciatic nerve. Drug testing was delayed until 10-14 days after surgery to ensure that neuropathic pain was well established prior to the initiation of drug delivery.

Figure 5A:
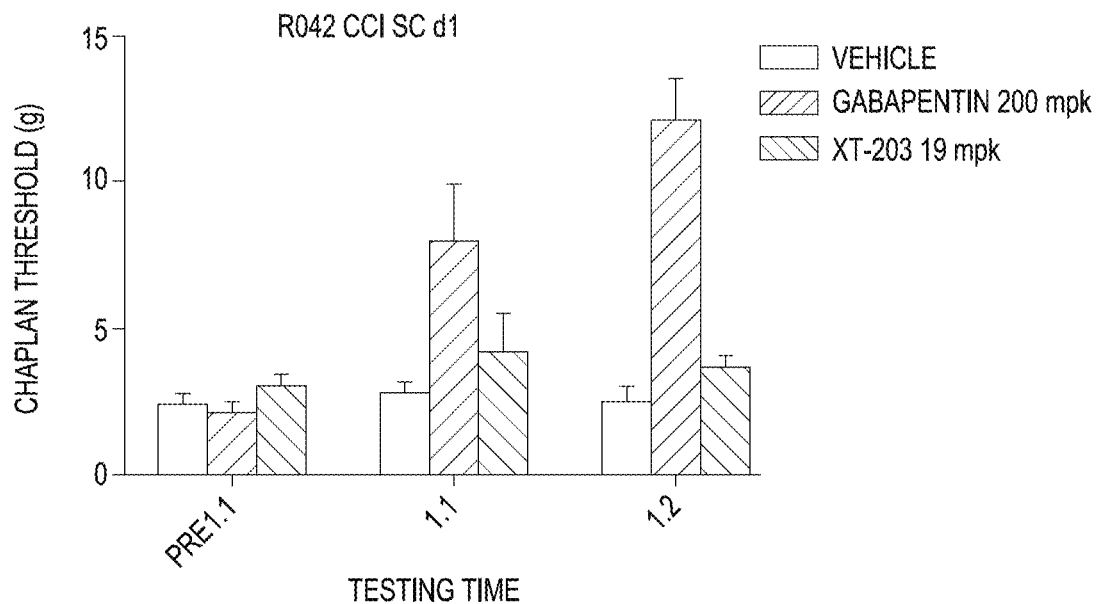
FIGS. 5A and 5B show the results of the effect of XT-203 (19 mg/kg) against vehicle and gabapentin (200 mg/kg) on rats subjected to CCI neuropathic pain model surgery after 1 day of dosing (FIG. 5A) and after five days of dosing (FIG. 5B) wherein dosing was carried out three times a day subcutaneously.
Figure 5B:
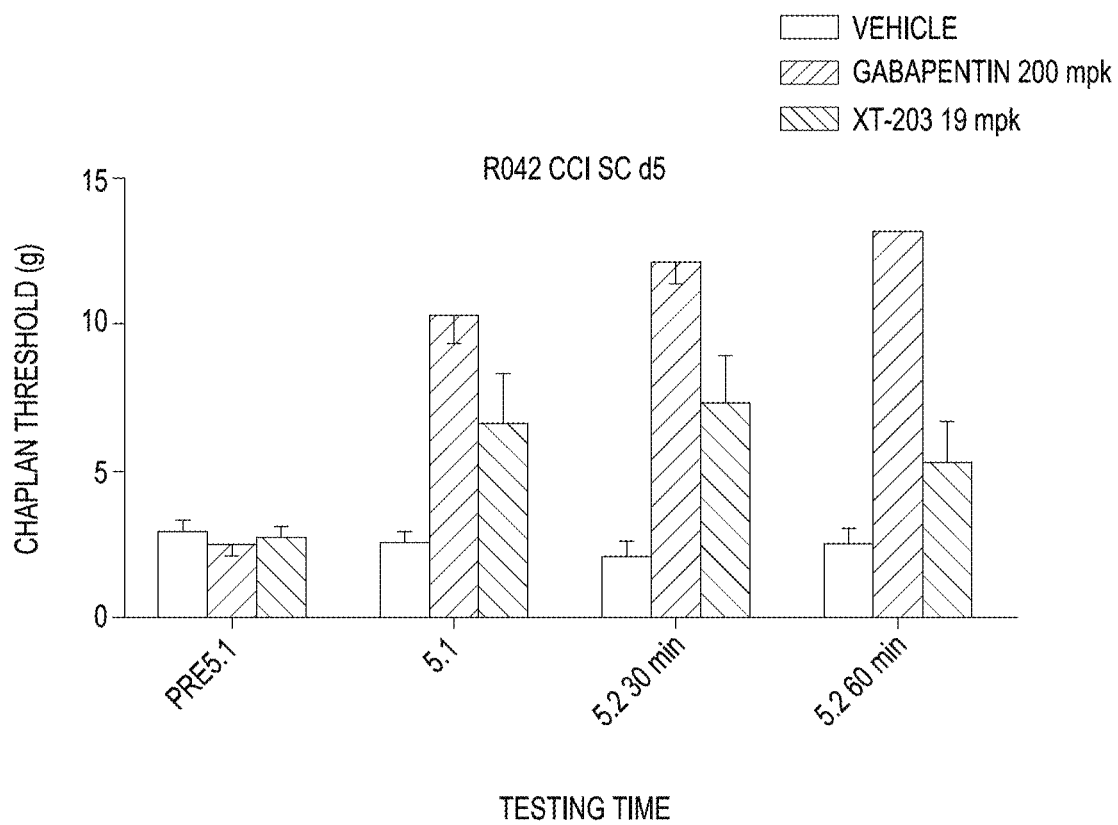

XT-203 CCI SC: Rats (10/group) were subjected to CCI neuropathic pain model surgery. After the pain state was established, they were dosed 3× per day for 5 days with XT-203 or a positive control (gabapentin) dose. Behavior testing for pain responses by von Frey testing was used to establish pain thresholds in the affected hind paw. Because dosage was 3×/day, behavior testing was performed after the first and second dose of day 1 dosing (1.1, 1.2) and after the first and second dose of day 5 dosing (5.1, 5.2). Testing sessions were performed 30 minutes after the dose was administered, except after the second dose of day 5, when the testing was performed at 30 and 60 minutes after the second dose (5.2 30 min and 5.2 60 min, respectively). FIGS. 5A and 5B show a minimal effect of XT-203 with day 1 dosing, but substantial effect during day 5 testing. (+)-NTX was not effective (data not shown).

Example 2

Von Frey Test for Mechanical Allodynia: Rats received at least three 60 min habituations to the test environment prior to behavioral testing. Response thresholds to calibrated light pressure stimuli applied to the plantar surface of the paws was measured using the von Frey test. The test was performed using 0.406-15.136 gm calibrated Semmes-Weinstein monofilaments (von Frey hairs; Stoelting, Wood Dale, Ill., USA) as described in detail previously (Milligan, et al., Brain Research, 861:105-116 (2000)). Briefly, rats were first assessed for baseline response thresholds (average of three consecutive withdrawal assessments) from each paw at 15 min intervals, and the average response threshold from both feet was calculated. All testing was conducted blind with respect to group assignment. The behavioral responses were used to calculate the threshold, by fitting a Gaussian integral psychometric function using a maximum-likelihood fitting method, as described in detail previously (Id.). Allodynia was assessed pre- and post-drug delivery.

Figure 6A:
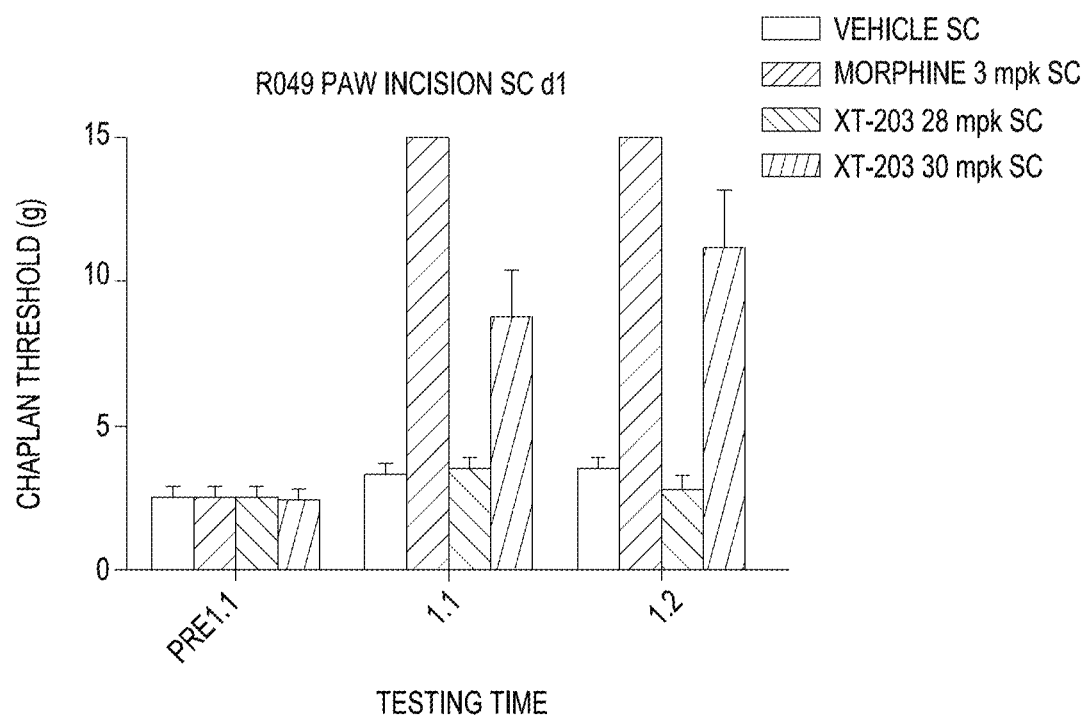
FIGS. 6A and 6B show the results of the effect of XT-203 (28 or 30 mg/kg) against vehicle and positive control (morphine at 3 mg/kg) groups on rats subjected to hind paw incision model surgery after 1 day of dosing (FIG. 6A) and after five days of dosing (FIG. 6B) wherein dosing was carried out three times a day subcutaneously.
Figure 6B:
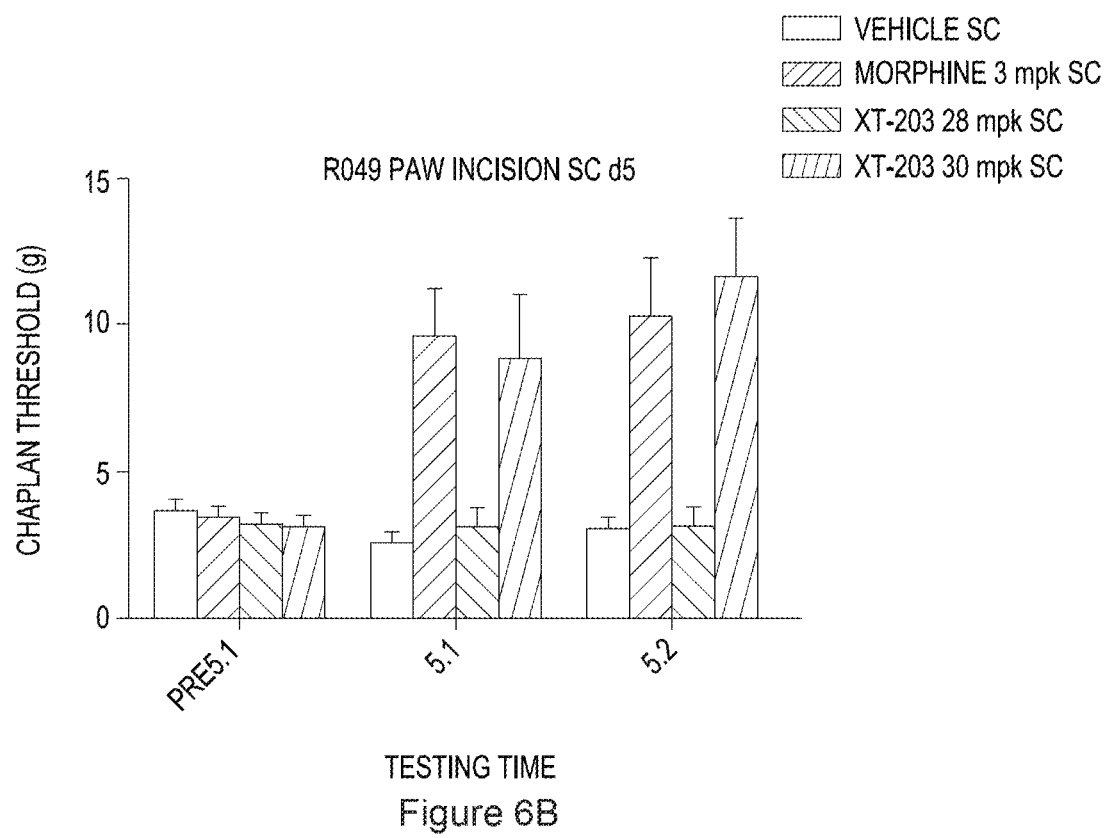

XT-203 Incisions SC: Rats (8/group) were subjected to hind paw incision pain model surgery. After the pain state was established, they were dosed 3× per day for 5 days with the indicated naltrexone or positive control (morphine) dose. Behavior testing for pain responses by von Frey testing was used to establish pain thresholds in the affected hind paw. Because dosage was 3×/day, behavior testing was performed after the first and second dose of day 1 dosing (1.1, 1.2) and after the first and second dose of day 5 dosing (5.1, 5.2). Testing sessions were performed 30 minutes after the dose was administered. FIGS. 6A and 6B show the substantial effects of XT-203 with day 1 and day 5 dosing, with the effect during day 5 testing matching the response to morphine. (+)-NTX was not effective (data not shown).

Example 3

NO assay: Microglia are the resident cells of the innate immune system in the central nervous system, and TLR4 is primarily expressed by microglia rather than astrocytes or neurons in the CNS. Given this expression profile, the BV-2 mouse microglia cell line was used as the model system of microglia, as these cells recapitulate many of the responses of primary microglia with high fidelity. TLR4 activation induces the downstream production of the inflammatory factor NO, which contributes to the development of neuropathic pain and drug addiction. BV-2 murine microglia were grown in supplemented DMEM (including 10% FBS, 50 unit mL$^{-1}$ penicillin, 50 µg·mL$^{-1}$ streptomycin). BV-2 cells were detached from the flask by trypsin digestion when ~80% confluence was reached. Cells were seeded at a density of 4×10$^4$ cells per well in 96-well plates. After overnight incubation, media was aspirated and changed to DMEM media without FBS. Cells were then treated with LPS (200 ng/ml) and different concentrations of the testing compounds. After 24 h treatment, 100 µL of supernatant media was removed after cells were treated for 24 h and added to flat black 96-well microfluor plates (Thermo Scientific, MA, USA). Subsequently, 10 µL of 2, 3-diaminonaphthalene (0.05 mg·mL$^{-1}$ in 0.62 M HCl) was added to each well and incubated for 15 min. The reaction was quenched by addition of 5 µL of 3 M NaOH and the plate was read on a Beckman Coulter DTX880 reader (Fullerton, Calif., USA) with excitation at 360 nm and emission at 430 nm.

Figure 7:
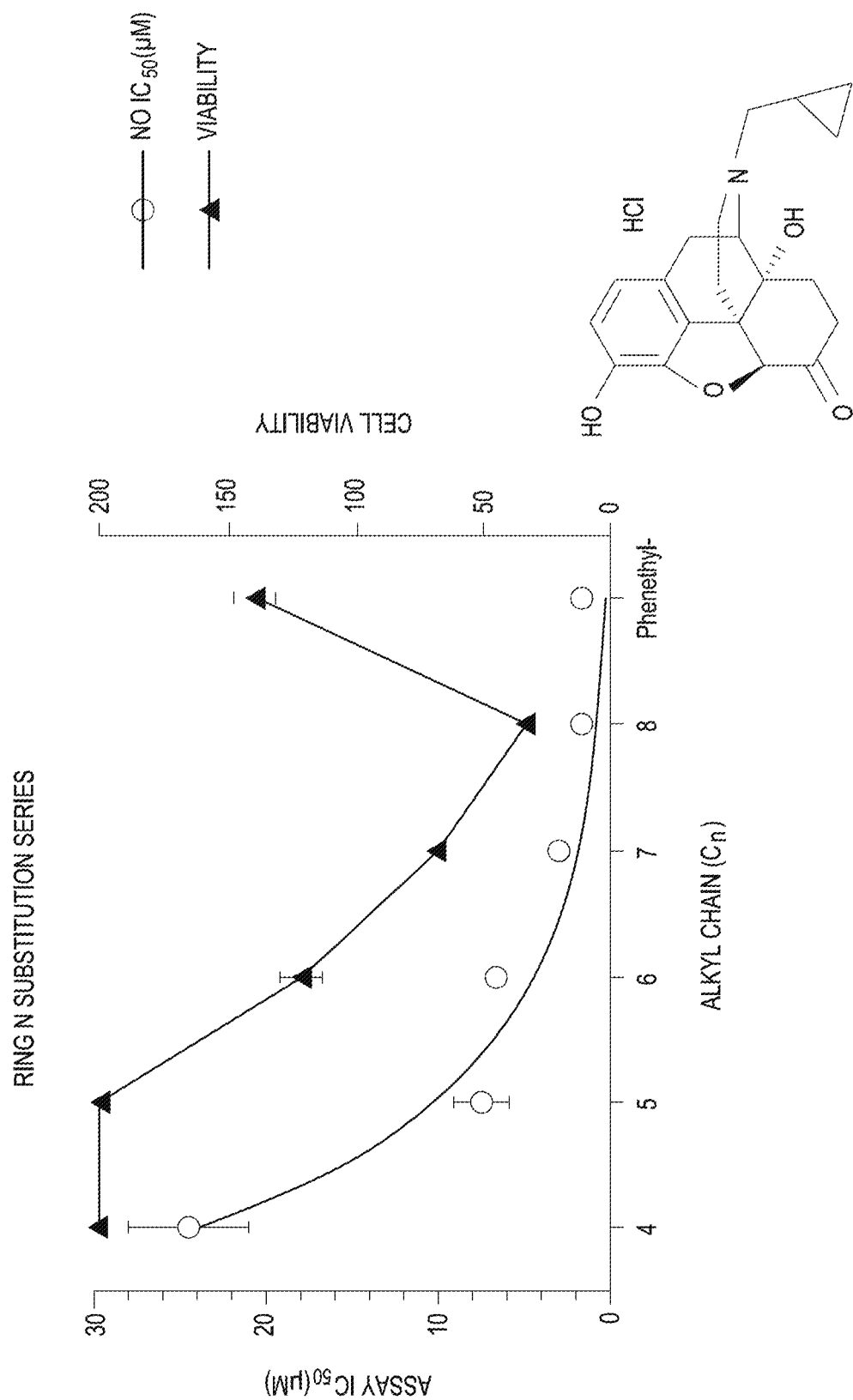
FIG. 7 shows a dose-inhibition curve graphed against the length of an N-alkyl chain for various tested compounds including a 4-, 5-, 6-, 7-, and 8-carbon chain, in addition to a phenethyl chain.

N chain NTX: This experimentation involved an in vitro assay where mouse BV2 cells were treated with LPS, which results in the release of nitric oxide (NO). Blockade of TLR4 activity results in reduced NO production. Therefore, IC$_{50}$ values were determined for test compounds that antagonize TLR4 activity. A series of test compounds were prepared, with different N-alkyl chains replacing the cyclopropyl methyl found in naltrexone. Cell viability was also measured by a standard assay, e.g., measurement of the release of cytoplasm-resident enzymes in the tissue culture supernatant or media to detect cell loss/lysis/rupture. A dose-inhibition curve was generated by testing the TLR4 antagonist compound for the ability to block LPS-stimulated iNOs induction. In FIG. 7, the inhibition levels across a range of doses are graphed, along with a regression curve. The IC$_{50}$ value—50% inhibition level—is also provided, graphed against the length of the alkyl chain. Note that with longer N-alkyl chain the IC$_{50}$ was reduced, although cell viability became problematic. However, a phenylethyl N-alkyl species exhibited the lowest mean IC$_{50}$ with improved cell viability.

Figure 8A:
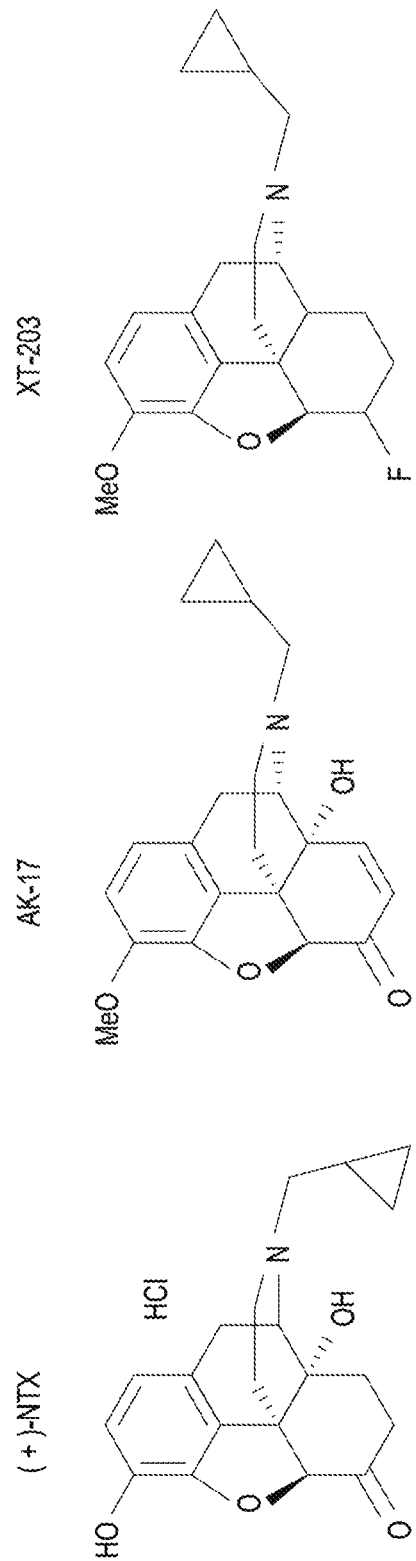
FIG. 8A shows the structure of three compounds tested for cell viability and inhibition of NO production ((+)-NTX, AK17, and XT-203).
Figure 8B:
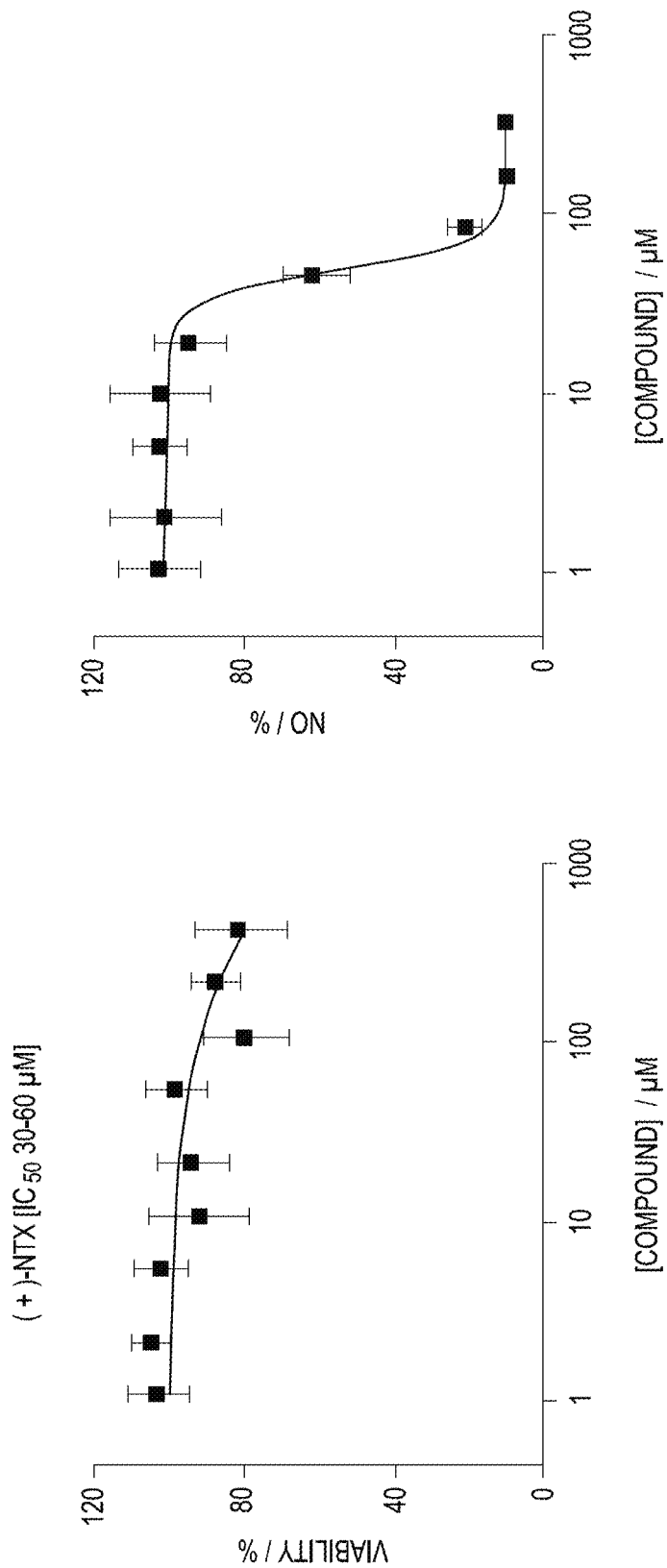
FIG. 8B shows the cell viability and inhibition of NO production for (+)-NTX.
Figure 8C:
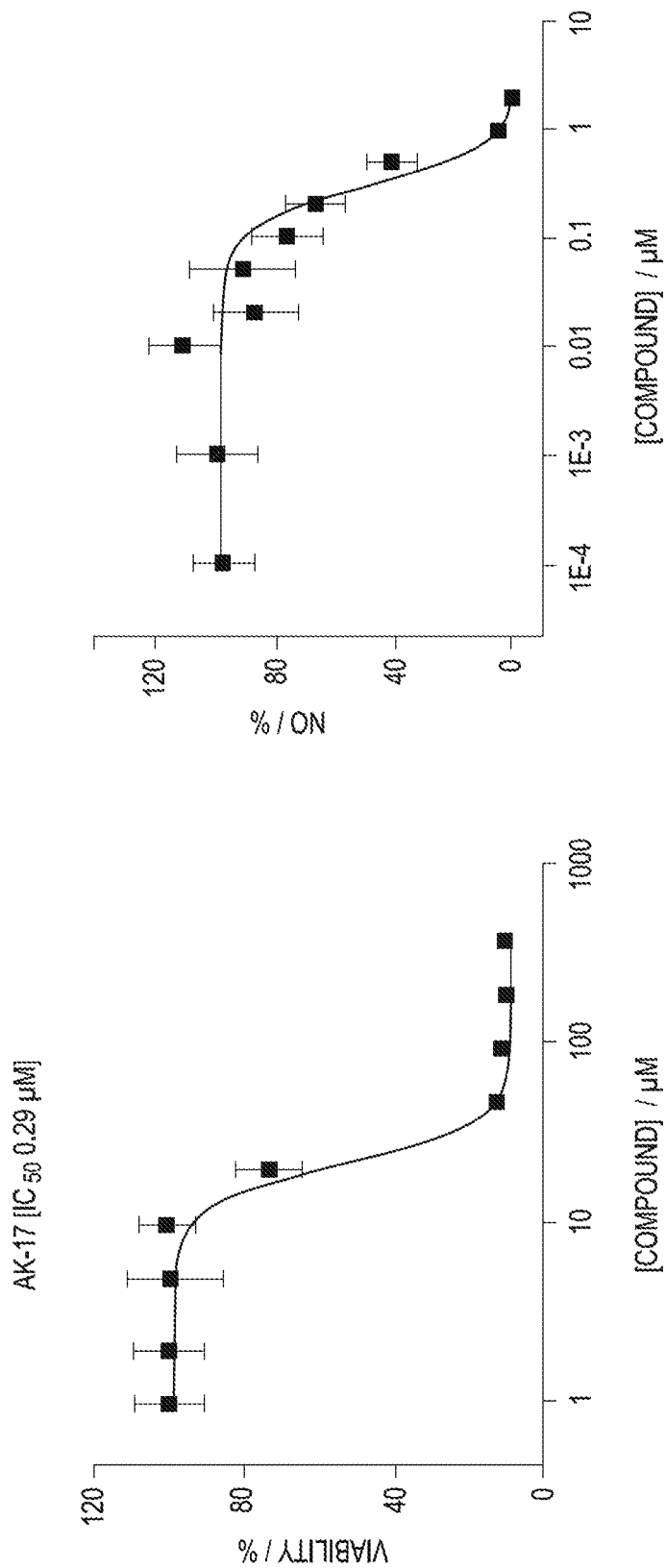
FIG. 8C shows the cell viability and inhibition of NO production for AK-17.
Figure 8D:
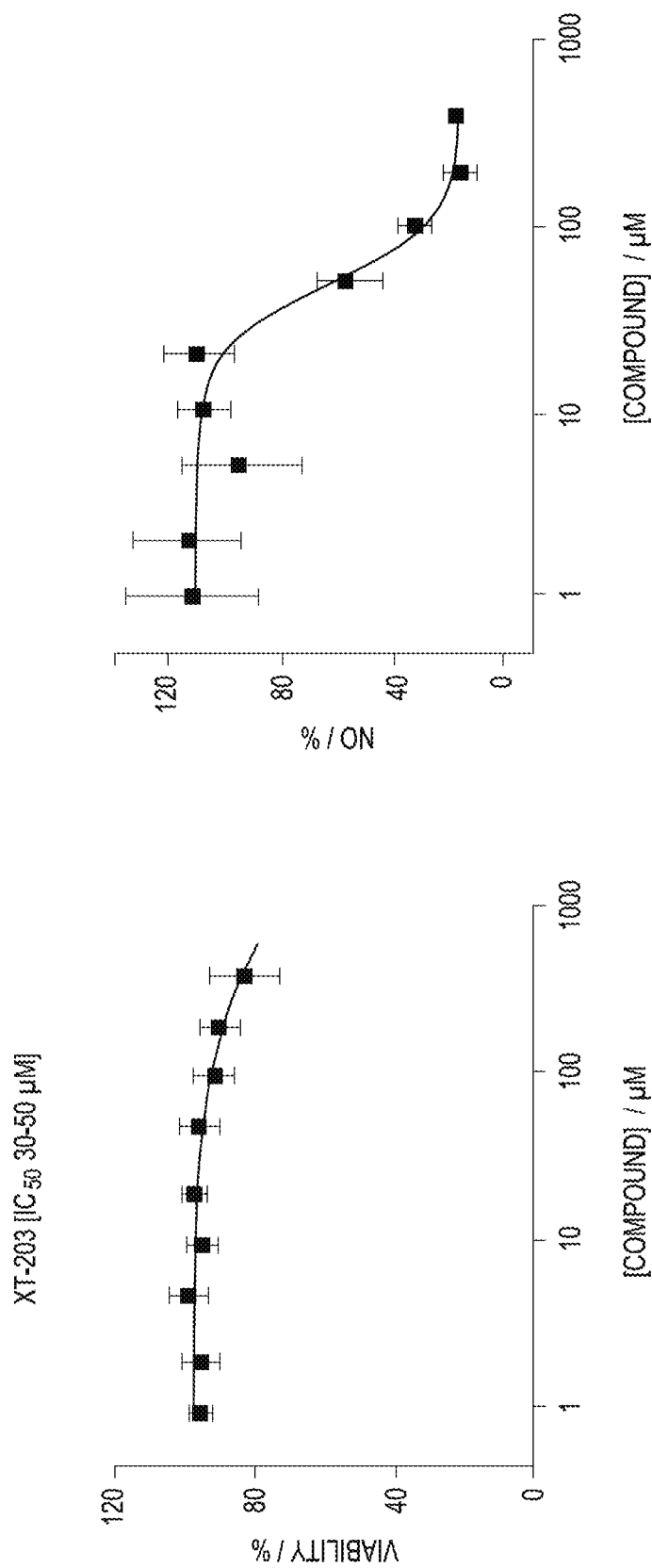
FIG. 8D shows the cell viability and inhibition of NO production for XT-203.

Efficacy of (+)-naltrexone, AK17 and XT-203: FIG. 8A shows the structure of two compounds known in the art ((+)-NTX ((+)-naltrexone) and AK-17) and an exemplary compound of Formula I (Formula VII, XT-203). FIGS. 8B to 8D show the results of the inhibition of NO production from LPS-stimulated BV2 cells using the assay described above. Note that (+)-NTX demonstrated both good viability and inhibition (FIG. 8B); AK-17 demonstrated good inhibition, but poor viability (FIG. 8C); and XT-203, like (+)-NTX, demonstrated good viability and inhibition (FIG. 8D). The results of the inhibition of NO production by compounds XT-206 to XT-217 are shown in Table 3 below.

TABLE 3

Cellular and Enzyme Inhibition of NO

| Compound | iNOS Cellular (µM) | iNOS Enzyme (µM) |
|---|---|---|
| (+)-naltrexone | 50-60 | N/A |
| XT-203 | 30-50 | N/A |
| XT-206 | >10 | >10 |
| XT-207 | >10 | >10 |
| XT-208 | >10 | >10 |
| XT-209 | >10 | >10 |
| XT-210 | >10 | >10 |

TABLE 3-continued

Cellular and Enzyme Inhibition of NO

| Compound | iNOS Cellular (µM) | iNOS Enzyme (µM) |
|---|---|---|
| XT-211 | >10 | N/A |
| XT-212 | >10 | N/A |
| XT-213 | >10 | N/A |
| XT-214 | >10 | N/A |
| XT-215 | >10 | N/A |
| XT-216 | >10 | N/A |
| XT-217 | >10 | N/A |

Example 4

Hepatocyte Elimination: (+)-NTX, AK-17 and XT-203 were incubated with cultured hepatocytes from the species listed in FIG. 9 and Table 4, and samples of the culture supernatant were collected over time. Samples were concentrated by nitrogen drying followed by reconstitution with 40% methanol for LC/MS analysis The data points were analyzed using the WinNonLin pharmacokinetics software package, and a half-life was determined that describes the rate of parent elimination. Note that XT-203 exhibited an enhanced half-life in human subjects compared to both (+)-NTX and AK-17. Replacement of the ketone group of (+)-NTX with fluorine (Formula VII, XT-203) thus results in an increase in half life in vitro, without significantly changing observed efficacy. The corresponding hepatocyte elimination half-life results for compounds XT-206 to XT-214 appear below in Table 4.

TABLE 4

Parent compound hepatocyte elimination half-life, $t_{1/2}$ (min)

| Compound | Mouse | Rat | Dog | Monkey | Human |
|---|---|---|---|---|---|
| (+)-naltrexone | 28.8 | 12.43 | 22.13 | 38.89 | 32.43 |
| AK-17 | 20.02 | 17.71 | 29.74 | 19.18 | 23.49 |
| XT-203 | 26.28 | 13.15 | 24.3 | 13.73 | 54.27 |
| XT-206 | 18.3 | 14.4 | 80.8 | 15.5 | 120.4 |
| XT-207 | 22.4 | 11.6 | 39.8 | 12.4 | 37.4 |
| XT-208 | 10.9 | 12.7 | 14.6 | 8.7 | 19.7 |
| XT-209 | 22.4 | 15.3 | 89 | 39.4 | 296.2 |
| XT-210 | 18.1 | 10.3 | 27.9 | 15.3 | 53.8 |
| XT-211 | 19 | 11.9 | 19.1 | 12.9 | 32.5 |
| XT-212 | 19.8 | 14.4 | 86.4 | 21.2 | 61.2 |
| XT-213 | 25.8 | 13.3 | 24.5 | 17.7 | 38.5 |
| XT-214 | 18.7 | 11.8 | 37.7 | 14.1 | 52.9 |
| XT-215 | 20.7 | 12.7 | 19.6 | 22.1 | 65.6 |
| XT-216 | 20.8 | 11.3 | 17.1 | 10.6 | 31.5 |
| XT-217 | 12.6 | 10.2 | 9.7 | 9.2 | 14.1 |

Example 5

Rat chronic constriction injury model-Oral and subcutaneous (+)-NTX and XT-203: An efficacy study was conducted in the rat chronic constriction injury (CCI) model (Study R042). The study design comprised two phases. A five-day period of oral (PO) dosing and behavioral testing was followed by a five-day period of subcutaneous (SC) dosing, with a two-day washout period between these periods. Dosing on each day was performed three times a day (TID). Behavioral testing for mechanical allodynia was performed on the first and fifth days of dosing, at three times on those days: before the first dose of the day, 30 minutes after the first dose of the day, and 30 minutes after the second dose of the day. Thus, day 5 testing is designated as pre5.1

Figure 10A:
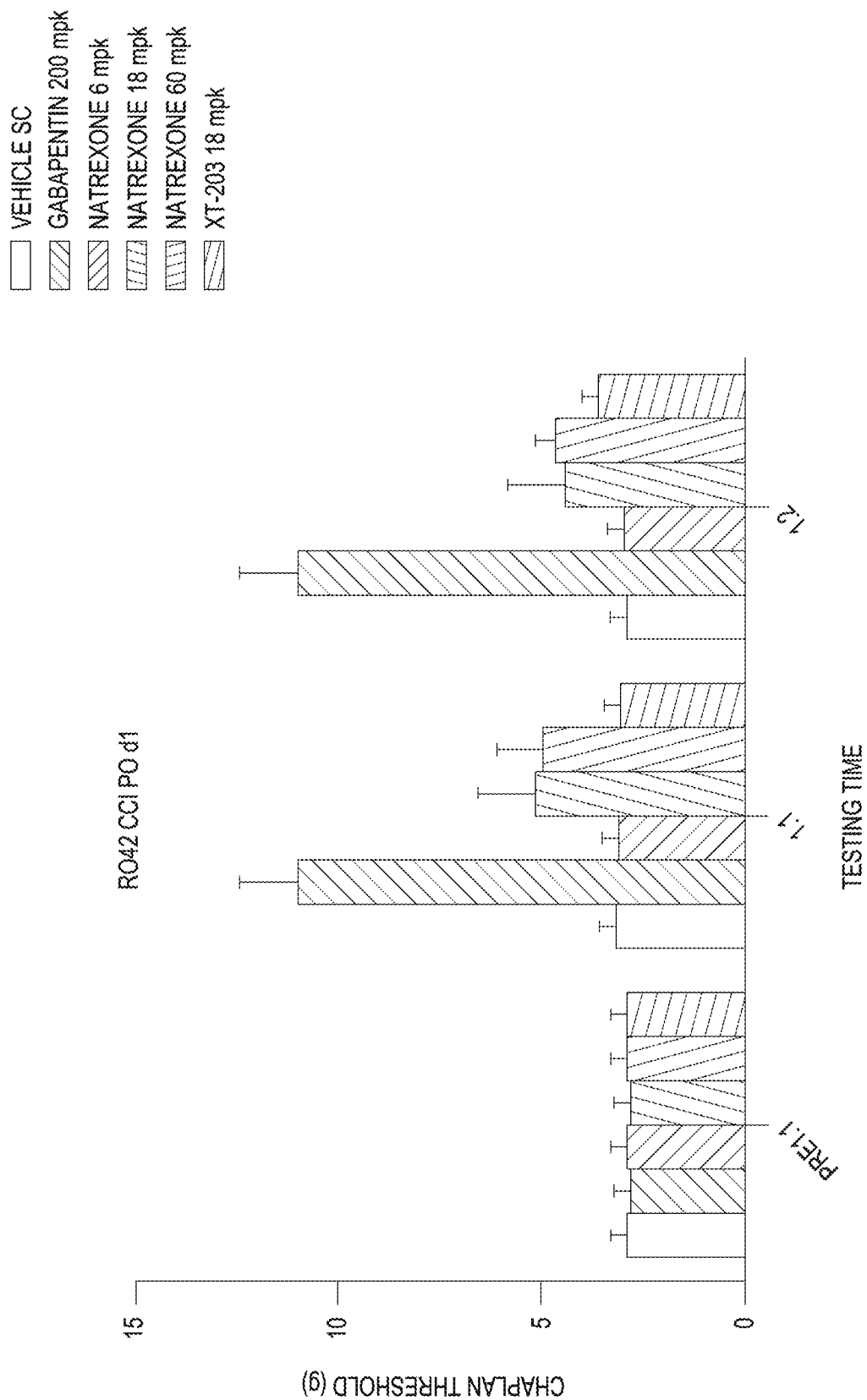
FIGS. 10A to 10D show the results of the effect of (+)-naltrexone (6, 18, and 60 mg/kg) and XT-203 (18 mg/kg) against vehicle and gabapentin (200 mg/kg) groups on rats subjected to CCI neuropathic pain model surgery after 1 day of oral phase dosing (FIG. 10A), 5 days of oral phase dosing (FIG. 10B), 1 day of subcutaneous dosing (FIG. 10C), and 5 days of subcutaneous dosing (FIG. 10D) wherein dosing was carried out three times a day.
Figure 10B:
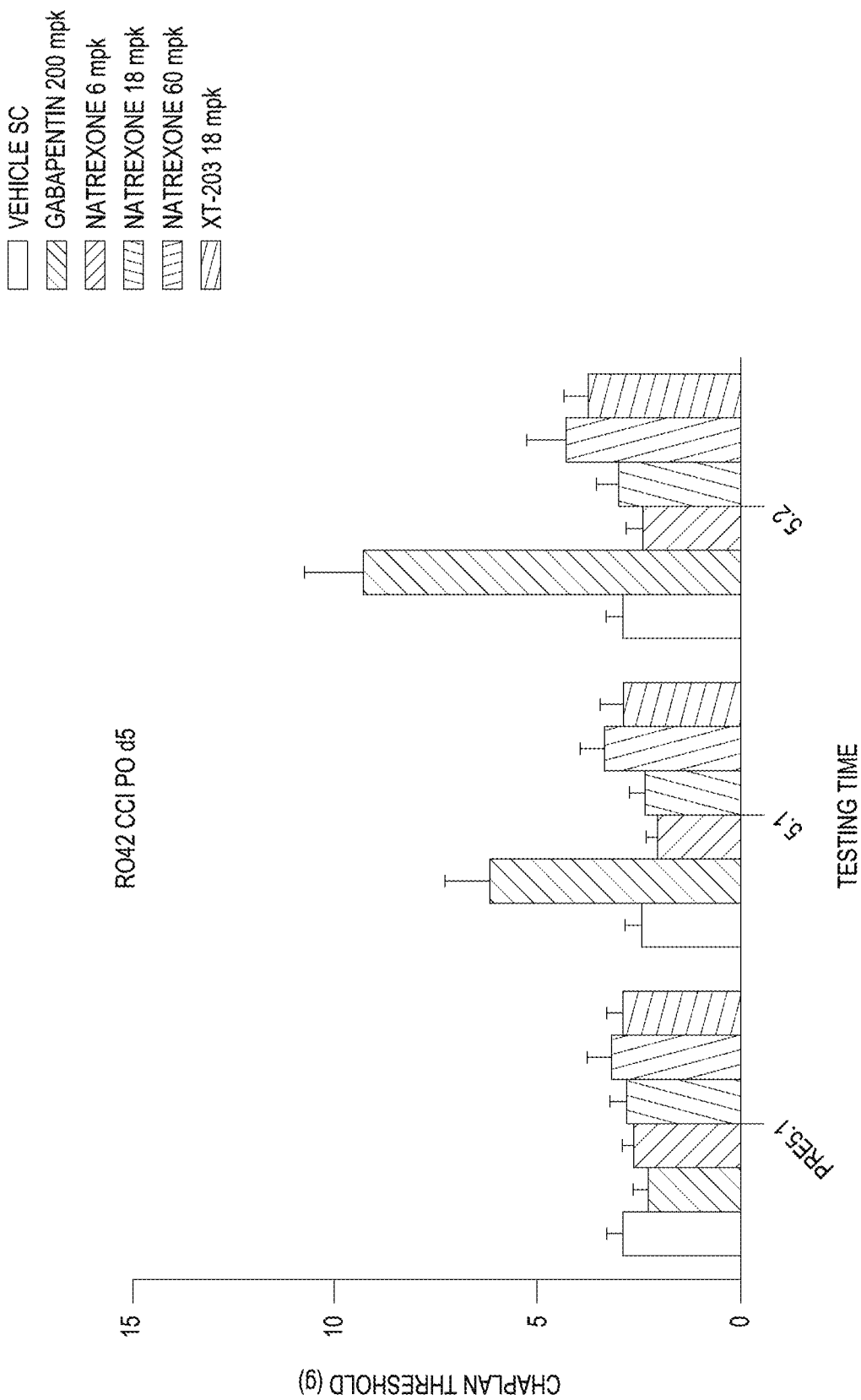
Figure 10C:
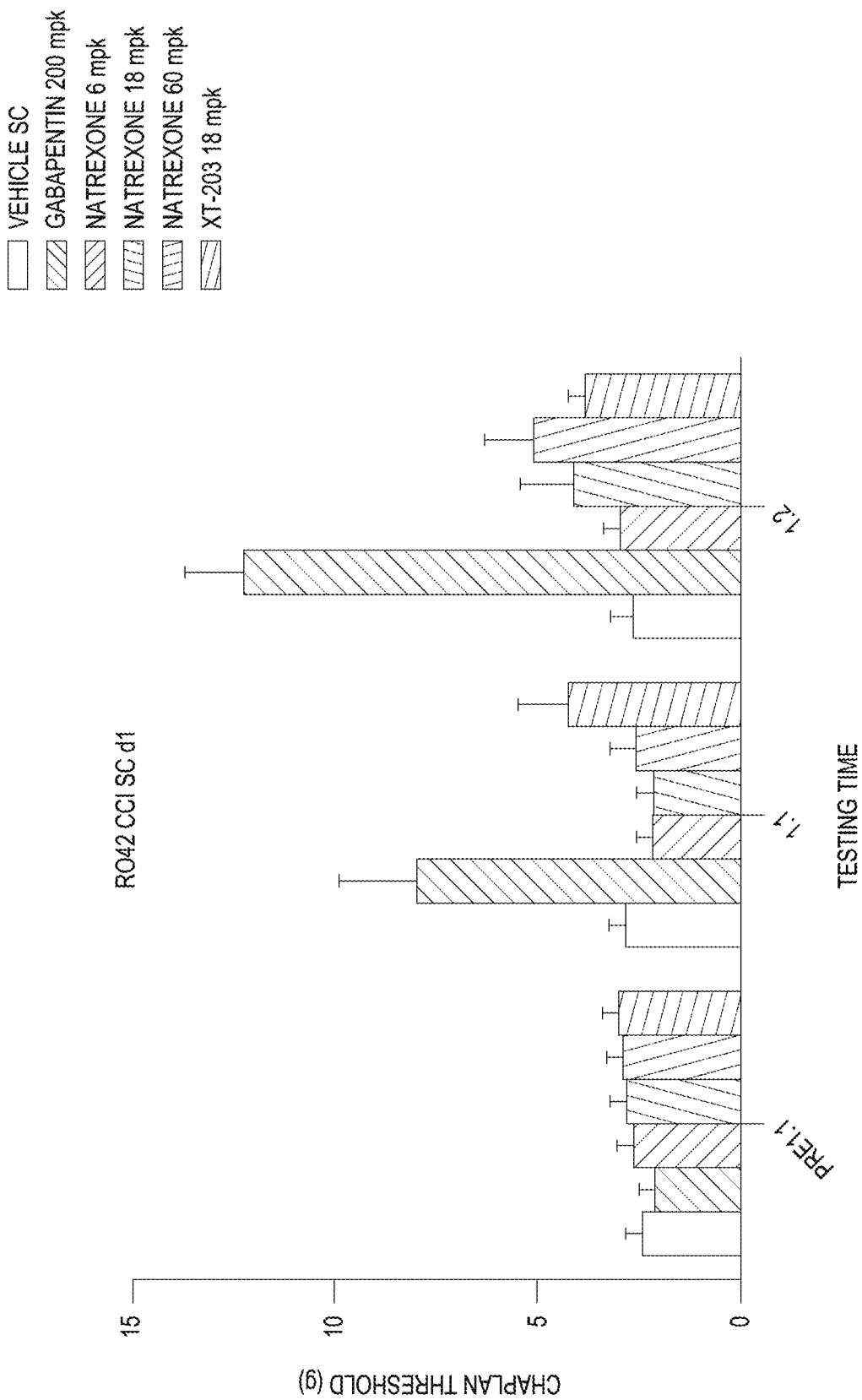
Figure 10D:
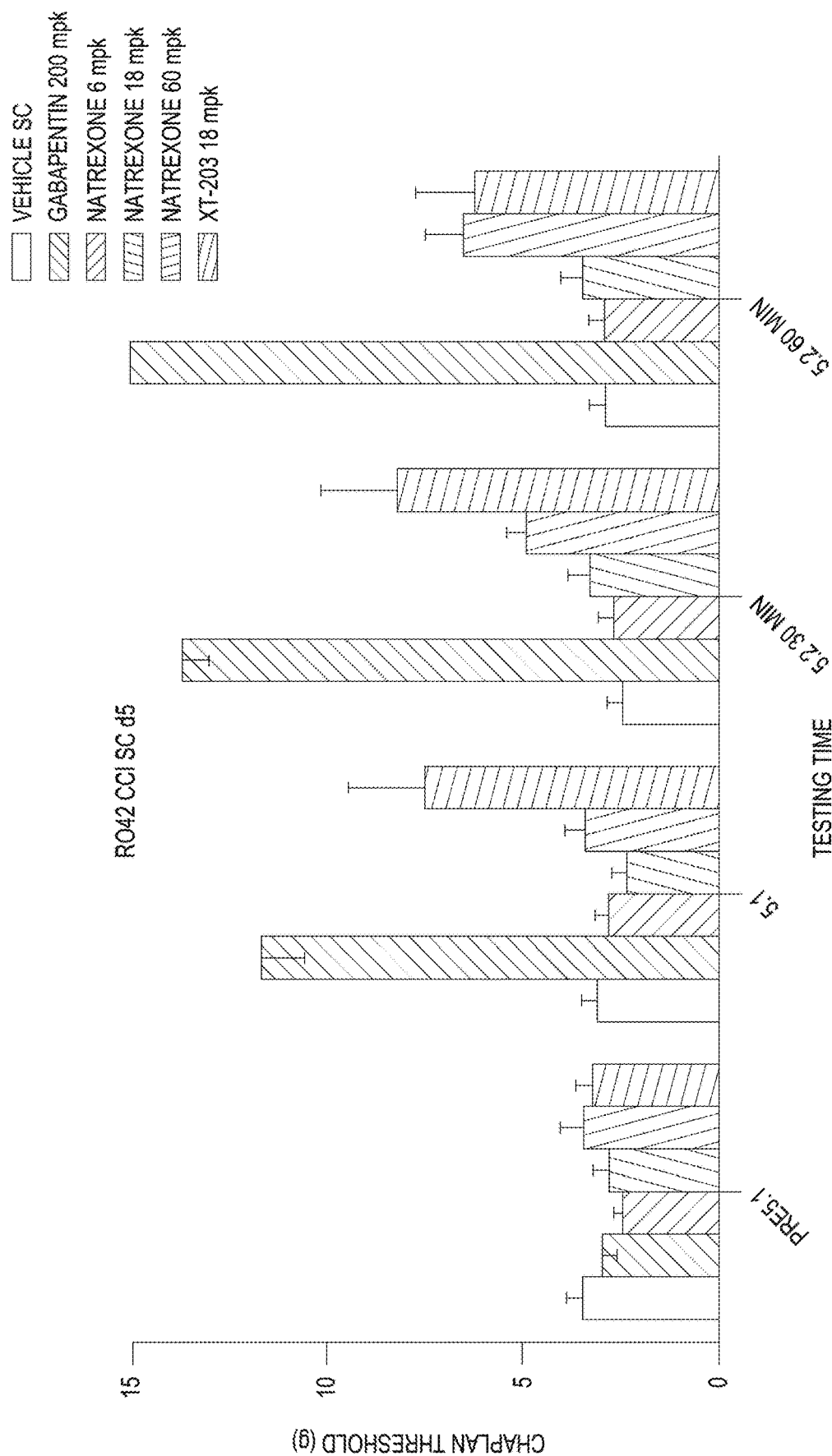

(before the first dose of the day), 5.1 (fifth day, after first dose) or 5.2 (fifth day, after second dose). On day 5 of the subcutaneous dosing phase, a second testing period was introduced 60 minutes after the second dose. (+)-NTX (6, 18, and 60 mg/kg) and XT-203. Mechanical allodynia was tested manually, using the Chaplan up-down testing method. The results are shown in FIGS. 10A and 10B, with the oral (PO) phase presented as the first pair of graphs. After the two-day washout, the subcutaneous (SC) phase was carried out with the results shown in the graphs at FIGS. 10C and 10D.

The CCI model was well established in this study, with allodynic response thresholds between 2 and 3 grams (pre-surgical baseline thresholds at 15 g, not shown). Both the vehicle and gabapentin controls worked appropriately, with reversals of allodynia at 200 mg/kg gabapentin. (+)-NTX, at medium and high doses, was able to demonstrate some efficacy at various points during this neuropathic pain model study (see PO d1, SC d1, and SC d5 panels in particular). This is especially remarkable given the extremely rapid metabolism and pharmacokinetics of (+)-NTX (see FIG. 9). Here, the dampening of efficacy due to lack of significant amounts of parent compound is particularly evident. Thus, the appropriate dose-ranging conditions in animal models should reflect (+)-NTX serum levels during efficacy testing, to match pharmacokinetics with pharmacodynamics. XT-203 at 18 mg/kg shows some significant efficacy when administered subcutaneously (see SC d5 panel). This is not a cumulative effect, as the pre5.1 test period does not show reversal of allodynia for the XT-203 group. Efficacy is only observed after the first dose on day 5. Thus, changes designed to improve compound stability do provide improved efficacy.

Example 6

Figure 11A:
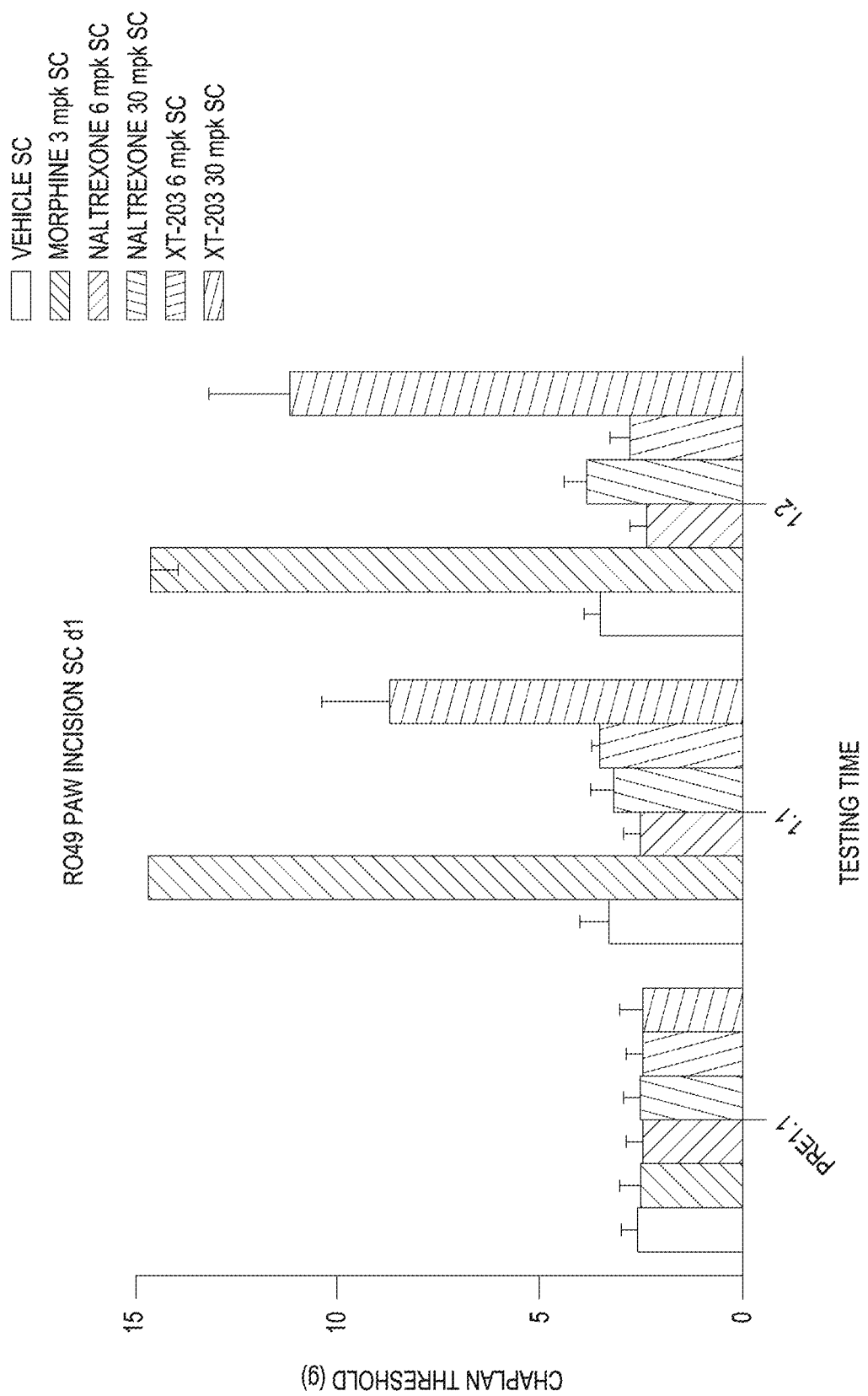
FIGS. 11A and 11B show the results of the effect of morphine, (+)-naltrexone, and XT-203 (6 or 30 mg/kg) against vehicle and positive control (morphine at 3 mg/kg) groups on rats subjected to hind paw incision surgery after 1 day of dosing (FIG. 11A) and after five days of dosing (FIG. 11B) wherein dosing was carried out three times a day subcutaneously.
Figure 11B:
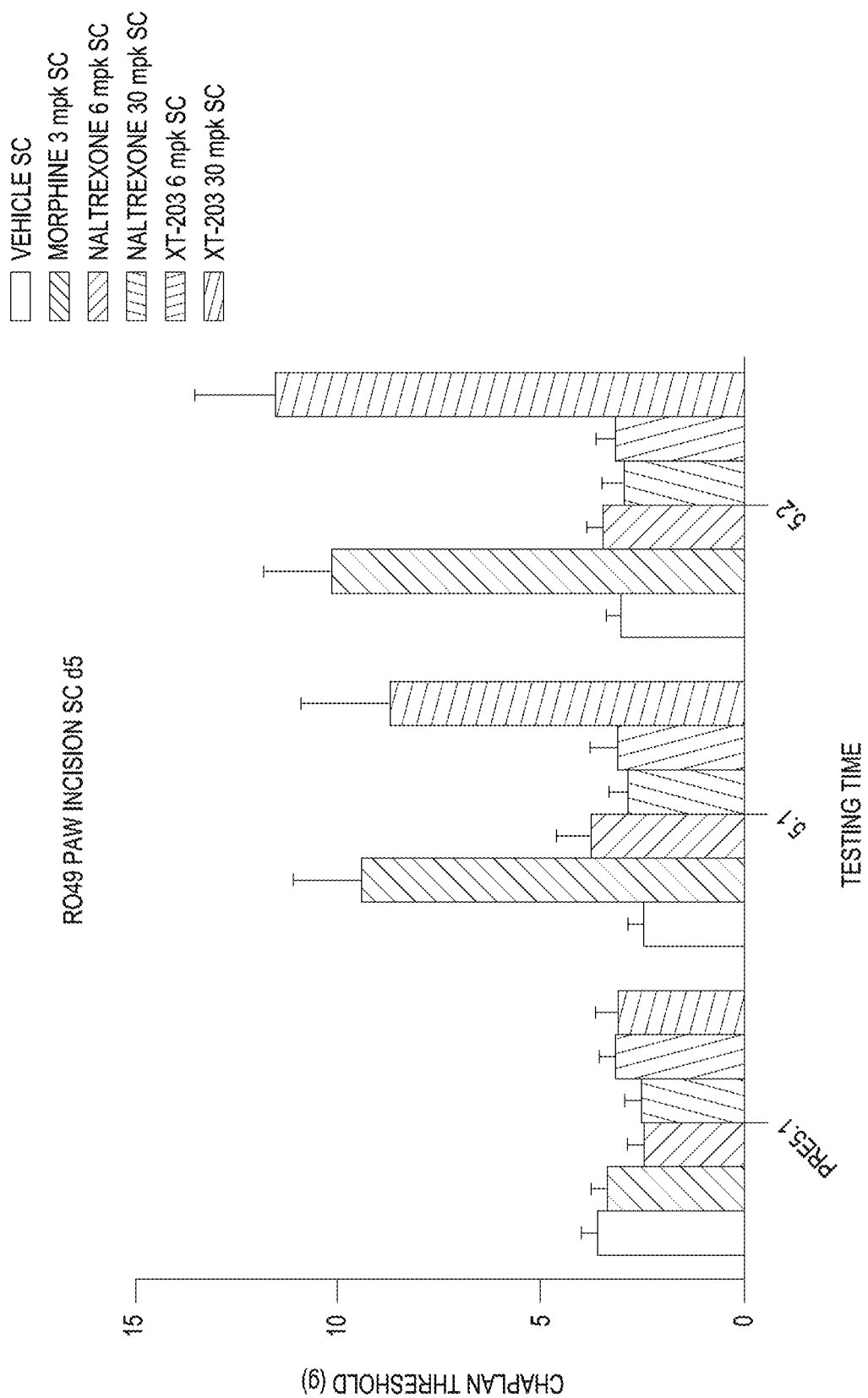

Rat paw incision model-Subcutaneous (+)-NTX and XT-203: The second efficacy study, R049, examined the efficacy of both (+)-NTX and XT-203 in an acute nociceptive pain model, the rat paw incision model. FIGS. 11A and 11B show the results of the effect of five days of TID subcutaneous dosing of the compounds (6 or 30 mg/kg) was compared against vehicle and positive control (morphine at 3 mg/kg) groups. Once again, the pharmacokinetics of (+)-NTX in the rat undercuts any efficacy that could be observed here, especially given the clear efficacy of (+)-NTX obtained in other studies with more targeted delivery.

XT-203 exhibited significant efficacy in this model at the high dose. This efficacy was at or near morphine levels, demonstrating that XT-203 is an effective compound in this model, even after the first dose. This class of non-opiate TLR4 antagonist compounds produces significant analgesic effects particularly when the rapid metabolism can be attenuated, and is the first demonstration that the intended systemic use of TLR4 antagonists, in immediate post-trauma or post-surgical situations, is appropriate. Without the opioid interference and glial activation, compounds like XT-203 and (+)-NTX are transformative in the treatment of post-surgical/post-trauma pain, eliminating the need for administration of highly addictive compounds such as morphine.

Mouse paw incision model-Intraperitoneal (+)-NTX and XT-203: Dose-response ranging was performed in this model, comparing morphine (control), (+)-NTX, and XT-203. In this model, 8-10 week old C57 B16 male mice received a 0.5 cm incision made on the plantar surface, underlying muscle and tendon incised longitudinally, followed by wound closure, under aseptic surgery with isoflurane anesthesia. A single dose of antibiotic (Amoxipen 100 mg/kg, IP) was administered for prevention of infection after surgery. The test articles were administered at the doses provided with a volume of administration of 5 mL/kg intraperitoneally.

Manual testing with von Frey hairs was performed at the times indicated in the graphs. The animals were placed in individual Perspex boxes on a raised metal mesh for at least 40 min before the test. A series of graduated von Frey hairs (0.07, 0.16, 0.4, 0.6, and 1.0 g) were applied to the plantar surface of the left paw, in sequence. Each von Frey hair was applied 10 times on a one-sec-on-one-sec-off protocol, with each hair slightly bent. A paw withdrawal upon this hind-paw stimulation for a given von Frey hair registering 5 responses out of 10 trials was recorded the paw withdrawal threshold (PWT). A baseline PWT was determined each day for 3 days before surgery. The PWT was assessed 5-10 days after surgery to demonstrate the pain response as a result of the surgery. In addition, the PWT was determined before dosing and 1, 2, and 4 hours after dosing.

The reasons for the dose-response ranging are two-fold. First, the efficacy of each compound at a given dose helps target dose levels for subsequent toxicology studies and dose scaling to human doses. Second, low dose of each compound, with minimal efficacy, may be used to determine whether (+)-NTX or XT-203 can work synergistically with morphine.

Figure 12A:
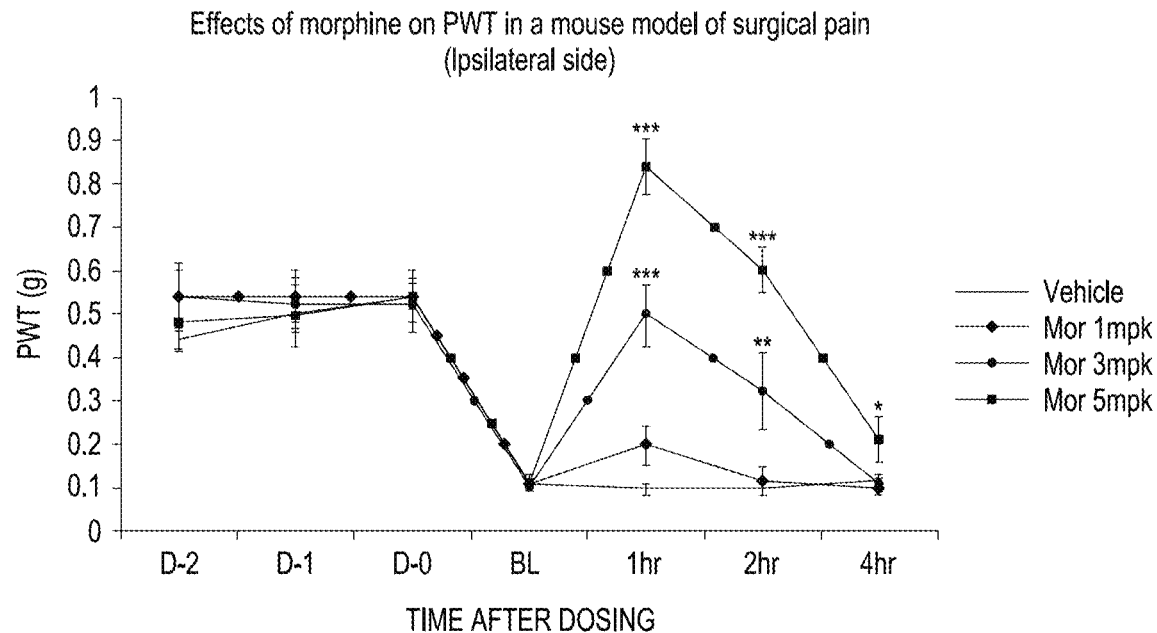
FIG. 12A to 12C consists of graphs showing the effects of morphine (FIG. 12A), (+)-naltrexone (FIG. 12B), and XT-203 (Formula VII, FIG. 12C) on paw withdrawal threshold in a mouse model of surgical pain.
Figure 12B:
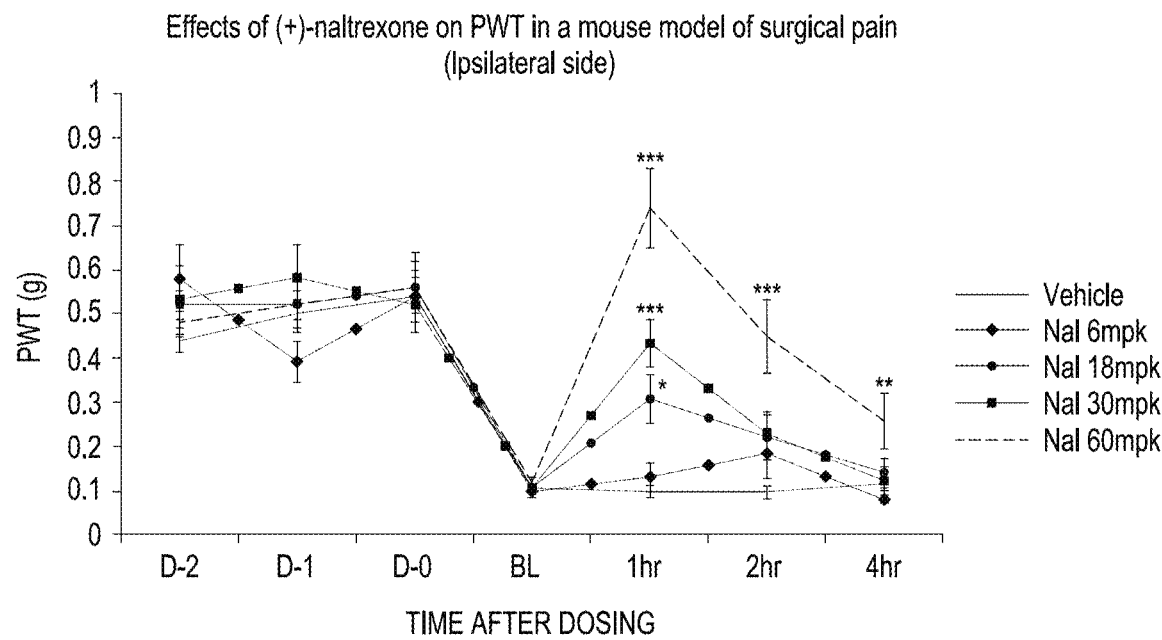
Figure 12C:
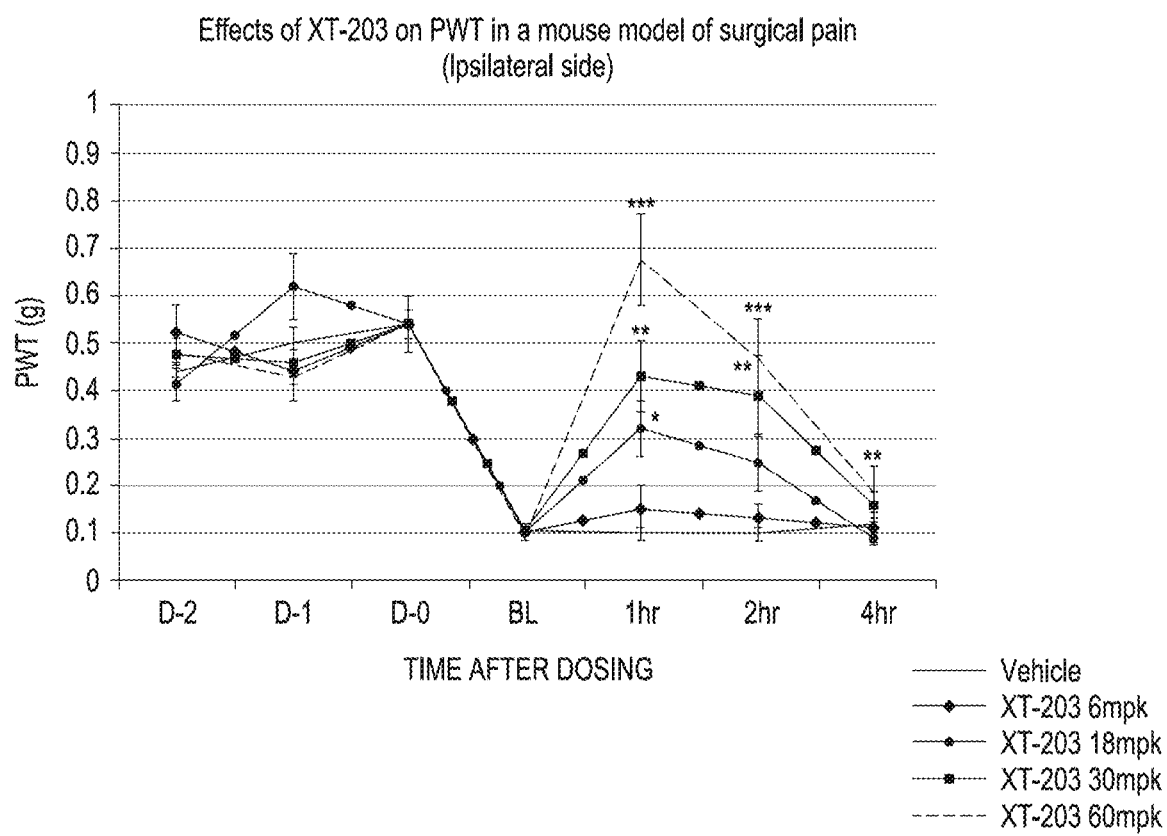

For the graphs in FIGS. 12A, 12B, and 12C, *, , *: $p<0.05$, 0.01 and 0.001, respectively, compared to the vehicle group, one-way ANOVA. Each group had n=10 mice.

All three compounds had evident efficacy at the first dose, with significant efficacy above control, with similar levels of efficacy at 18 mg/kg (+)-NTX and 10 mg/kg XT-203. These effects were sustained at the high doses for at least two hours. This profile is reasonably consistent with the in vitro parent compound elimination observed previously (~27 minute half-lives for both compounds, see FIG. 9 and Table 4).

Example 7

Mouse paw incision model—Morphine potentiation—Intraperitoneal (+)-NTX and XT-203: Morphine is known to oppose its own pain efficacy by binding to TLR4 and driving glial activation. Co-administration of morphine with a TLR4 antagonist like (+)-NTX or XT-203 produces a synergistic effect, such that less morphine would be is to attain the same level of pain relief. This synergy has the added benefit of reducing the total amount of morphine required, which reduces the incidence of adverse opioid side effects and decreases the likelihood of tolerance and dependence.

Studies thus were carried out to determine whether (+)-NTX or XT-203, or both, could synergize with low-dose morphine to produce a more-than-additive analgesic effect.

A low dose of each compound, with minimal efficacy, was used to determine whether (+)-NTX or XT-203 can work synergistically with morphine. In both cases, morphine was dosed at 1 mg/kg IP. In one group of animals, morphine was combined with XT-203 at 10 mg/kg, and in the second group, morphine was combined with (+)-NTX at 18 mg/kg. Each of these doses, independently, produced minimal or subthreshold responses compared to the vehicle group.

Figure 13A:
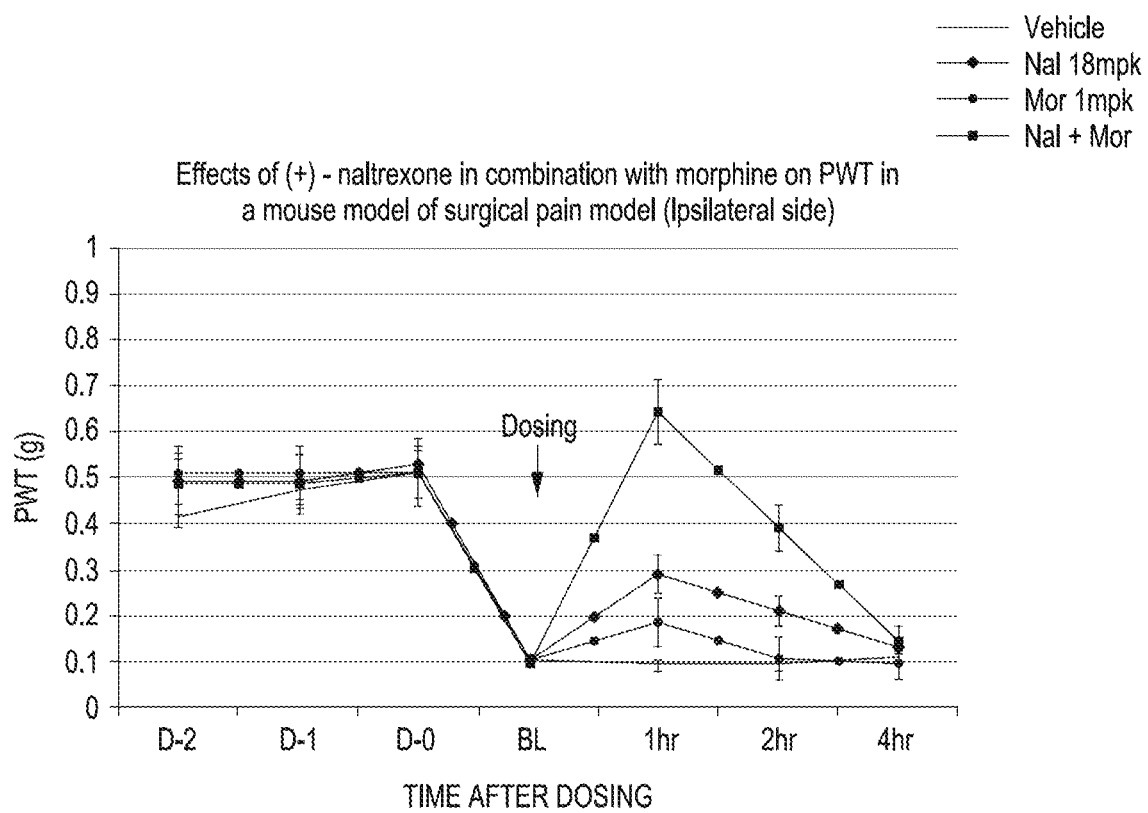
FIG. 13A consists of a graph showing the effects of (+)-naltrexone in combination with morphine, and FIG. 13B consists of a graph showing the effects of XT-203 (Formula VII) in combination with morphine, on paw withdrawal threshold in a mouse model of surgical pain.
Figure 13B:
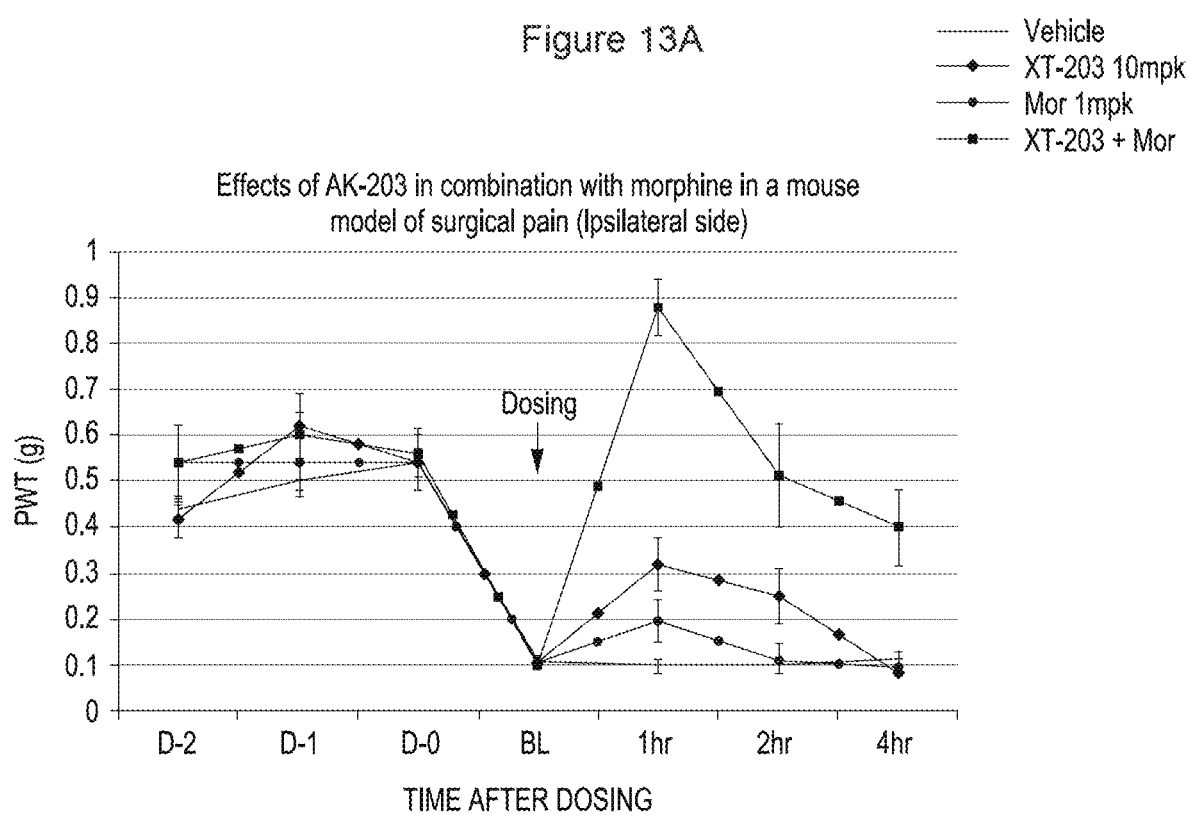

For the graphs in FIGS. 13A and 13B, *, , *: $p<0.05$, 0.01 and 0.001, respectively, compared to the vehicle group, one-way ANOVA. Each group had n=10 mice.

The graph of FIG. 13A shows (+)-NTX, at 18 mg/kg, administered together with morphine at 1 mg/kg, a 'sub-effective' dose, produced an effect that was amplified and prolonged compared to that induced by (+)-NTX or morphine alone. The effect of the combination treatment was also greater than the sum of the effects induced by (+)-NTX and morphine alone, in the ipsilateral hind-paws. (+)-NTX, dosed at 18 mg/kg, slightly but significantly increased the paw withdrawal threshold (PWT) of the ipsilateral hind-paw from the baseline level of 0.11±0.015 g to 0.31±0.056 g, 0.22±0.050 g and 0.14±0.32 g at the 1, 2 and 4 hour time points post-dosing, respectively. Morphine, at 1 mg/kg, produced a slight and short-lasting increase in PWT. Following dosing, the PWT amounted to 0.20±0.046 g, 0.11±0.033 g and 0.10±0.014 g, at 1, 2 and 4 hour time points after dosing. However, when (+)-NTX at 18 mg/kg was administered together with morphine at 1 mg/kg, the PWT change was greater than that induced by (+)-NTX or morphine alone. The PWT increased from 0.11±0.015 g before dosing to 0.68±0.074 g, 0.41±0.051 g and 0.16±0.030 g at 1, 2 and 4 hours following dosing, respectively.

The graph of FIG. 13B shows XT-203 at 10 mg/kg, when administered with morphine at 1 mg/kg, a 'sub-effective' dose in the ipsilateral hind-paws, produced an effect that was amplified and prolonged compared to that induced by XT-203 and morphine administered alone. The effect was also increased in magnitude compared to the sum of the effects induced by XT-203 and by morphine. In the 10 mg/kg XT-203 group, the PWT increased from 0.11±0.015 g before dosing to 0.32±0.058 g, 0.25±0.059 g and 0.09±0.012 g at the 1, 2 and 4 hour time points after dosing, respectively. Morphine, at 1 mg/kg, only slightly increased the PWT from the baseline level of 0.11±0.015 g to 0.20±0.046 g at the 1 hour time point after dosing. The PWT (0.11±0.033 g and 0.10±0.014 g) at the 2 and 4 hour time points following dosing with morphine (1 mg/kg), were neither significantly different from that of baseline levels, nor from that of vehicle at the same time points. However, following dosing with XT-203, together with morphine, the PWT increased from the baseline level of 0.11±0.015 g to 0.88±0.061 g, 0.51±0.114 g and 0.40±0.083 at 1, 2 and 4 hours post dosing, respectively. At all time points, the PWT following dosing were also significantly higher than that of vehicle at the same time points. Furthermore, the PWT produced by the combination of XT-203 and morphine was higher than the sum of the effects of dosing with XT-203 and morphine alone (0.52, 0.36 and 0.19 g at 1, 2 and 4 hours post dosing, respectively). No significant adverse effects were observed in any morphine dose groups throughout the period of observation. The XT-203/morphine combination exhibited superior pain reversal in this model than the (+)-NTX/morphine combination, both in absolute level of reversal and duration of effect.

Example 8

Mouse bone fracture model—Intraperitoneal (+)-NTX and XT-203. Male adult C57BL6 mice, 8-10 weeks old, were anaesthetized with isoflurane mixed with oxygen throughout the surgical procedure. Animals were placed on a thermo-blanket temperature control system. The left knee area was disinfected with povidone/iodine-soaked cotton. A 0.5 cm incision was made on the knee, exposing the front area of the knee. A 27-gauge sterile needle was inserted into the tibial bone medullar canal to secure the fractured bone. The left tibia bone was gently broken using a pair of cushioned pliers. A single dose of antibiotic (Amoxipen 100 mg/kg, IP) was administered for prevention of infection after surgery. The animal was placed in a temperature-controlled recovery chamber until fully awake before being placed in a plastic cage bedded with clean, soft sawdust, with food and water easily accessible. The condition of the animals was closely monitored and recorded. All compounds, dissolved in normal saline, were dosed intraperitoneally in a volume of 5 ml/kg. PWT testing, as described above, was performed at 1, 2, and 4 hours.

Figure 14A:
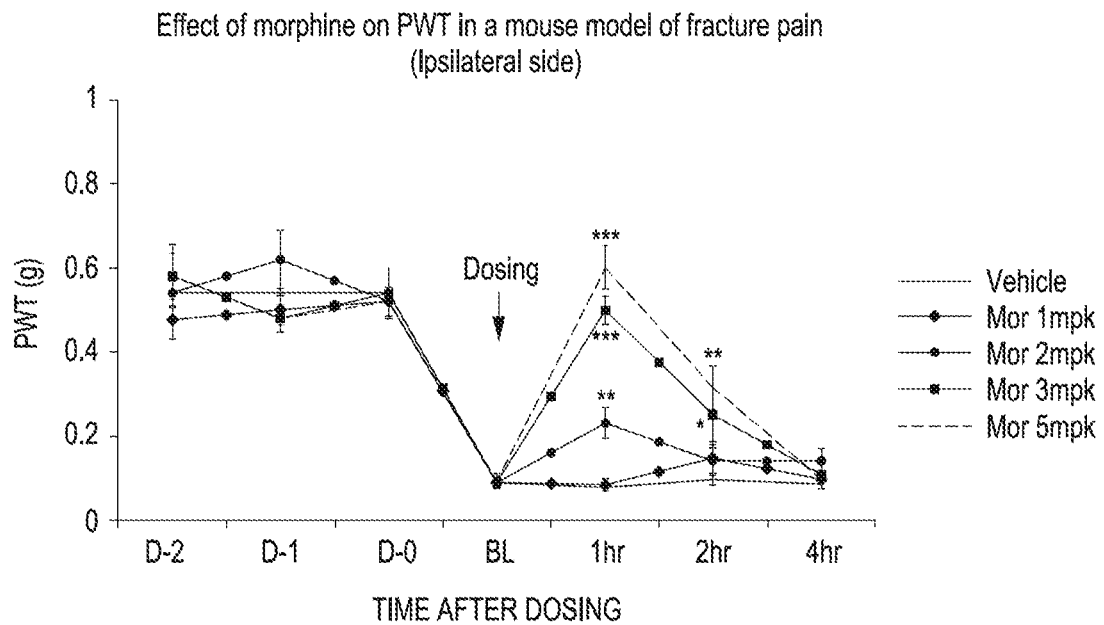
FIG. 14A to 14C consists of graphs showing the effects of morphine (FIG. 14A), (+)-naltrexone (FIG. 14B), and XT-203 (Formula VII, FIG. 14C) in a mouse model of fracture pain.
Figure 14B:
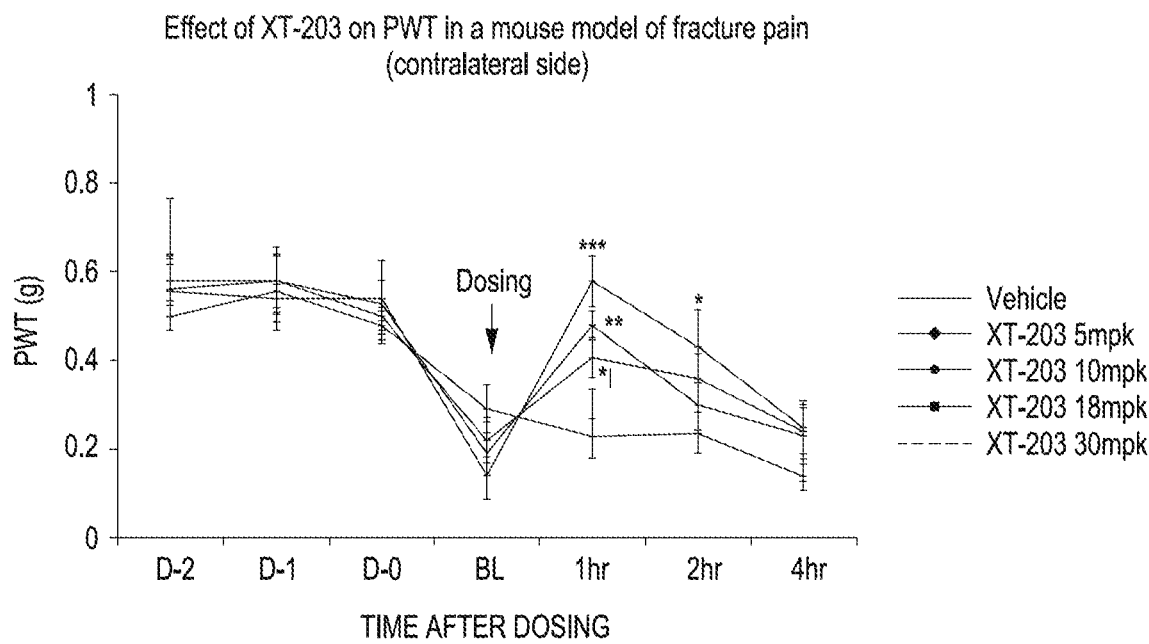
Figure 14C:
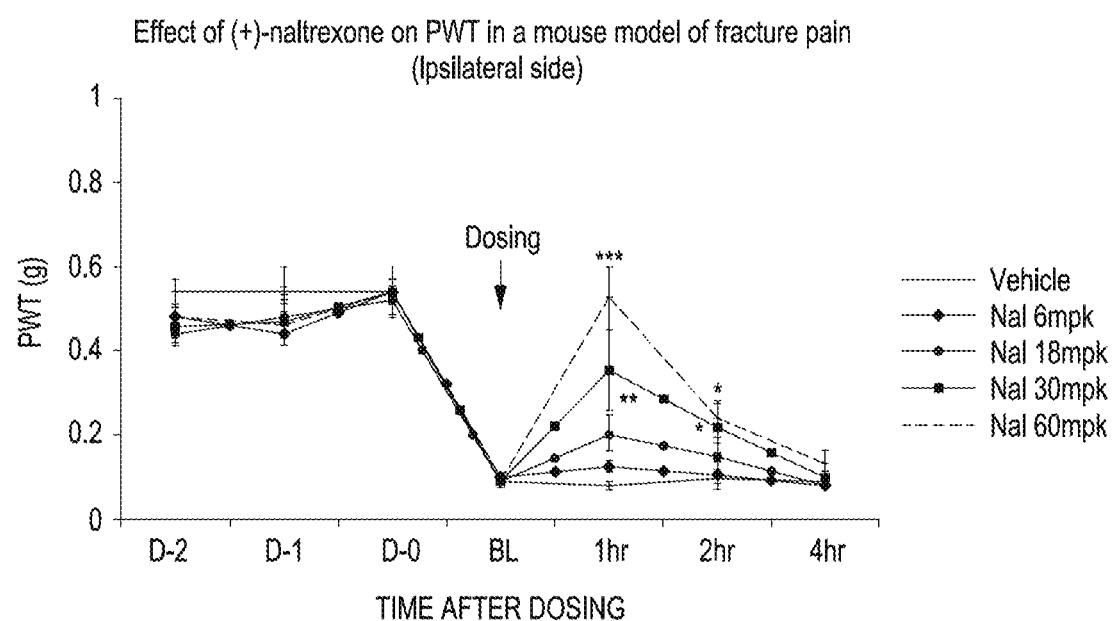

For the data provided in the three graphs in FIGS. 14A, 14B, and 14C: *, , *: $p<0.05$, 0.01 and 0.001, respectively, compared to the vehicle group, one-way ANOVA. Each group had n=10 mice.

Summary of Results: 1) Morphine, at 1, 2, 3 and 5 mg/kg, increased the PWT in the hind-paw in this mouse model of bone fracture pain in a dose-dependent manner. The results are in line with the historical data from the laboratory. 2.) XT-203, at 6, 10, 18 and 30 mg/kg, increased the PWT in this mouse fracture pain model in a dose-dependent manner. 3.) (+)-NTX, at 6, 18, 30 and 60 mg/kg, increased the PWT in this mouse fracture pain model in a dose-dependent manner. 4.) No significant adverse effects were observed in any XT-203 or (+)-NTX dose groups throughout the period of observation. However, at 5 mg/kg, there were some mice showing walking anti-clockwise at 1 hour after dosing. From two hours onward, this phenomenon disappeared.

Example 9

Figure 15A:
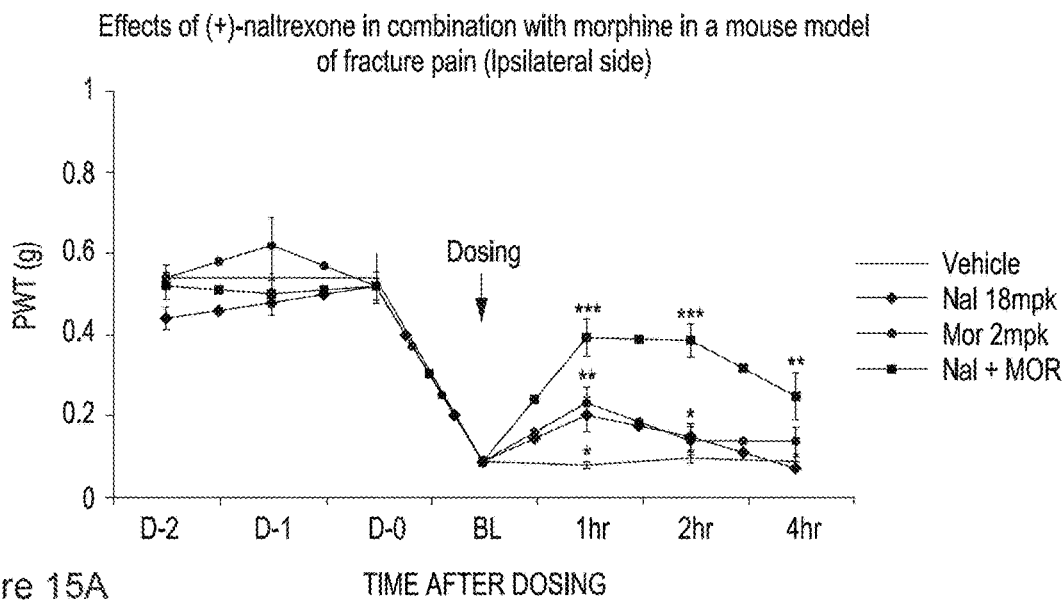
FIG. 15A consists of a graph showing the effects of (+)-naltrexone in combination with morphine, and FIG. 15B consists of a graph showing the effects of XT-203 (Formula VII) in combination with morphine, on paw withdrawal threshold in a mouse model of fracture pain.
Figure 15B:
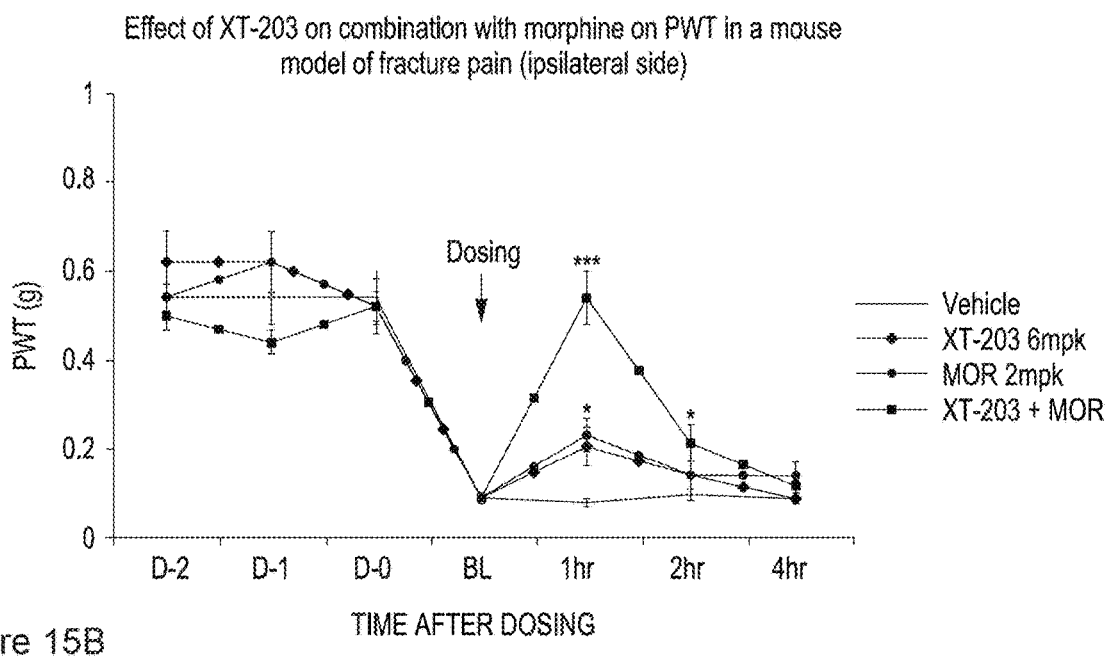

Mouse bone fracture model—Morphine potentiation—Intraperitoneal (+)-NTX and XT-203: As above in the paw incision model, a low dose of each compound, with minimal efficacy, was used to determine whether (+)-NTX or XT-203 could work synergistically with morphine. In both cases, morphine was dosed at 2 mg/kg IP. In one group of animals, morphine was combined with XT-203 at 6 mg/kg, and in the second group, morphine was combined with (+)-NTX at 18 mg/kg. Each of these doses, independently, produced minimal or subthreshold responses compared to the vehicle group. The results are shown in FIGS. 15A and 15B.

Summary of Results: 1.) (+)-Naltrexone, at 18 mg/kg, in combination with morphine at 2 mg/kg, produced an effect greater than either compound administered alone. The synergetic effects appeared around the 2 hour time point. 2.) XT-203, at 6 mg/kg, in combination with morphine at 2 mg/kg, a 'marginally-effective' dose, produced a greater effect on ipsilateral PWT than either compound administered alone in the mouse fracture pain model. This data suggests a synergistic analgesic effect of the two compounds. 3.) No significant adverse effects were observed in any XT-203 or (+)-NTX dose groups throughout the period of observation. 4.) For both models, a lower dose of XT-203 was required to demonstrate morphine synergy compared to (+)-NTX. This may be due in part to observed significantly higher glucuronidation of (+)-NTX parent compound in mouse hepatocytes, despite a similar parent elimination half-life for both compounds.

Example 10

In addition to the animal studies presented above in Examples 1-9, the results of in vitro testing of several of the compounds (i.e., XT-203, XT-204, and XT-206 through XT-217) are shown in Table 5 and Table 6. Compound XT-202 is (+)-naltrexone. Note, none of these compounds exhibited significant activity at the hERG channel, an early development signal of downstream disqualifying cardiovascular effects. XT-203 did exhibit activity at two targets in the screening results at 10 M test concentration, but those activities were reduced below the 50% level at the 1 M test concentration. Nine additional compounds had two or fewer off-target hits in the screening. Of these, five had no off-target hits (XT-204, -206, -207, -211, and -212), two had one off-target hit (XT-209 and -214), and two had two off-target hits (XT-208 and -217). These compounds spanned all of the tested N-modification classes. Two sulfonamides exhibited the same off-target hit patterns (XT-208 and -217), without significant improvements in parent compound elimination half-life values across species. In some cases, significant variability across species for the half-lives is observed (e.g., XT-206 values range from 14.4 to 120.4 minutes, XT-209 values range from 15.3 to 296.2 minutes), and in other cases the half-life variability is suppressed across species compared to XT-203 (e.g., XT-208 values range from 8.7 to 19.7 minutes, and XT-217 values range from 9.2 to 14.1 minutes, compared with 13.15 to 54.27 minutes for XT-203). With regard to the parent compound elimination half-life in human hepatocytes, three of the low off-target hit compounds exhibited longer parent duration than (+)-naltrexone: XT-206, -207, -209, -212, and -214. Three of these compounds (XT-206, -209, and -212) exhibited longer parent duration than XT-203 in this assay, with truly significant improvements for XT-206 and XT-209 (120.4 and 296.2 minutes, respectively, compared to 32.43 minutes for (+)-naltrexone and 54.27 minutes for XT-203). Thus, the medicinal chemistry approach taken in this series of fluorinated compounds can yield low off-target activity and longer metabolic lifetime while preserving TLR4 antagonism. It is appreciated that further development of compounds in this class, using techniques known to those skilled in the art, may yield additional compounds with desirable pharmacologic and toxicologic characteristics.

TABLE 5

Off-Target Inhibition and hERG Inhibition

| Compound | % Inhibition at 10 μM | | hERG inhibition IC$_{50}$ uM) |
|---|---|---|---|
| (+)-naltrexone | none | N/O | >100 |
| XT 203 | Adrenergic α2A (retest at 1 μM) | 64 | >100 |
|  | Sodium channel site 2 (retest at 1 μM) | 54 |  |
| XT-206 | none | N/O | >10 |
| XT-207 | none | N/O | >10 |
| XT-208 | Adenosine A2A | 64 | >10 |
|  | Cannabinoid CB1 | 54 |  |
| XT-209 | Protein tyrosine kinase LCK | 61 | >10 |
| XT-210 | Adrenergic α1A | 87 | >10 |
|  | Adrenergic α1B | 97 |  |
|  | Adrenergic α1D | 82 |  |

TABLE 5-continued

Off-Target Inhibition and hERG Inhibition

| Compound | % Inhibition at 10 μM | | hERG inhibition IC$_{50}$ uM) |
|---|---|---|---|
|  | Adrenergic α2A | 97 |  |
|  | Adrenergic α2B | 104 |  |
|  | Calcium channel L-Type phenylalkylamine | 51 |  |
|  | Dopamine D2L | 75 |  |
|  | Dopamine D2S | 77 |  |
|  | Sodium channel site 2 | 70 |  |
| XT-211 | none | N/O | N/A |
| XT-212 | none | N/O | N/A |
| XT-213 | Adrenergic α1B | 72 | N/A |
|  | Adrenergic α1D | 79 |  |
|  | Adrenergic α2A | 83 |  |
|  | Calcium channel L-Type phenylalkylamine | 59 |  |
|  | Opiate κ (OP2, KOP) | 52 |  |
|  | Serotonin (5-hydroxytryptamine) 5-HT2B | 90 |  |
|  | Sodium channel site 2 | 100 |  |
| XT-214 | Adrenergic α2A | 51 | N/A |
| XT-215 | Adrenergic α1A | 85 | 10(51%) |
|  | Adrenergic α1B | 99 |  |
|  | Adrenergic α1D | 92 |  |
|  | Adrenergic α2A | 96 |  |
|  | Adrenergic α2B | 105 |  |
|  | Calcium channel L-Type, benzothiazepine | 51 |  |
|  | Calcium channel L-Type, phenylalkylamine | 73 |  |
|  | Cannabinoid CB1 | 57 |  |
|  | Dopamine D2L | 65 |  |
|  | Dopamine D2S | 81 |  |
|  | Histamine H2 | 82 |  |
|  | Opiate κ (OP2, KOP) | 79 |  |
|  | Opiate κ (OP3, MOP) | 79 |  |
|  | Sodium channel site 2 | 101 |  |
|  | Tachykinin NK1 | 55 |  |
|  | Transporter, Norepinephrine (NET) | 61 |  |
| XT-216 | Adenosine A2A | 57 | N/A |
|  | Cannabinoid CB1 | 82 |  |
|  | GABA A, chloride channel, TBOB | 54 |  |
|  | Opiate κ (OP2, KOP) | 69 |  |
|  | Progesterone, PR-B | 50 |  |
|  | Transporter, Adenosine | 60 |  |
|  | Transporter, Dopamine (DAT) | 52 |  |
|  | Transporter, Norepinephrine (NET) | 59 |  |
|  | Vasopressin V1A | 69 |  |
| XT-217 | Adenosine A2A | 61 | N/A |
|  | Cannabinoid CB1 | 56 |  |

TABLE 6

Compiled Data

| Cmpd | Assay | % inhibition at 10 μM | iNOS cellular** | iNOS enzyme | Mouse* | Rat* | *Dog | NHP* | Human* | hERG inhibition IC50 (μM) |
|---|---|---|---|---|---|---|---|---|---|---|
| XT-202 (+)-Naltrexone | NONE |  | 50-60 | N/A | 28.8 | 12.43 | 22.13 | 38.89 | 32.43 | >100 |
| XT-203 | Adrenergic α2A | 99 (19% at 1 μM) | 30-30 | N/A | 26.28 | 13.15 | 24.3 | 13.73 | 54.27 | >100 |
|  | Na channel site 2 | 64 (18% at 1 μM) |  |  |  |  |  |  |  |  |

TABLE 6-continued

Compiled Data

| Cmpd | Assay | % inhibition at 10 µM | iNOS cellular** | iNOS enzyme | Mouse* | Rat* | *Dog | NHP* | Human* | hERG inhibition IC50 (µM) |
|---|---|---|---|---|---|---|---|---|---|---|
| XT-204 | none | | 0.29 | N/A | 20.05 | 17.71 | 29.74 | 19.18 | 23.49 | >10 |
| XT-206 | none | | >10 | >10 | 18.3 | 14.4 | 80.8 | 15.5 | 120.4 | >10 |
| XT-207 | none | | >10 | >10 | 22.4 | 11.6 | 39.8 | 12.4 | 37.4 | >10 |
| XT-208 | Adrenergic α2 Cannabinoid CB1 | | >10 | >10 | 10.9 | 12.7 | 14.6 | 8.7 | 19.7 | >10 |
| XT-209 | Protein kinase LCK | | >10 | >10 | 22.4 | 15.3 | 89 | 39.4 | 296.2 | >10 |
| XT-210 | Adrenergic α1A | 87 | >10 | >10 | 18.1 | 10.3 | 27.9 | 15.3 | 53.8 | >10 |
| | Adrenergic α21B | 97 | | | | | | | | |
| | Adrenergic α21D | 82 | | | | | | | | |
| | Adrenergic α2A | 97 | | | | | | | | |
| | Adrenergic α2B | 104 | | | | | | | | |
| | Ca channel L-type*** | 51 | | | | | | | | |
| | Dopamine D2L | 75 | | | | | | | | |
| | Dopamine D2S | 77 | | | | | | | | |
| | Na channel site 2 | 70 | | | | | | | | |
| XT-211 | none | | >10 | na | 19 | 11.9 | 19.1 | 12.9 | 32.5 | >10 |
| XT-212 | none | | >10 | na | 19.8 | 14.4 | 86.4 | 21.2 | 61.2 | >10 |
| XT-213 | Adrenergic α21B | 72 | >10 | na | 25.8 | 13.3 | 24.5 | 17.7 | 38.5 | >10 |
| | Adrenergic α21D | 79 | | | | | | | | |
| | Adrenergic α2A | 83 | | | | | | | | |
| | Ca channel L-type*** | 59 | | | | | | | | |
| | Opiate κ (OP2,KOP) | 52 | | | | | | | | |
| | Serotonin 5-HT2B | 90 | | | | | | | | |
| | Na channel site 2 | | | | | | | | | |
| XT-214 | Adrenergic α2A | 51 | >10 | na | 18.7 | 11.8 | 37.7 | 14.1 | 52.9 | >10 |
| XT-215 | Adrenergic α1A | 99 | >10 | na | 20.7 | 12.7 | 19.6 | 22.1 | 65.6 | 51% |
| | Adrenergic α21D | 92 | | | | | | | | |
| | Adrenergic α2A | 96 | | | | | | | | |
| | Ca channel L-type**** | 73 | | | | | | | | |
| | Ca channel L-type*** | 51 | | | | | | | | |
| | Cannabinoid CB1 | 57 | | | | | | | | |
| | Dopamine D2L | 65 | | | | | | | | |
| | Dopamine D2S | 81 | | | | | | | | |
| | Histamine H2 | 82 | | | | | | | | |
| | Opiate κ (OP2,KOP) | 79 | | | | | | | | |
| | Opiate µ (OP3,KOP) | 79 | | | | | | | | |
| | Na channel site 2 | 101 | | | | | | | | |
| | Tachykinin NK1 | 55 | | | | | | | | |
| | Transporter, Norepinephrine | 61 | | | | | | | | |
| XT-216 | Adenosine A2A | 57 | >10 | na | 20.8 | 11.3 | 17.1 | 10.6 | 31.5 | >10 |
| | Cannabinoid CB1 | 82 | | | | | | | | |
| | GABA A, chloride channel | 54 | | | | | | | | |
| | Opiate κ (OP2,KOP) | 69 | | | | | | | | |
| | Progesterone, PR-B | 50 | | | | | | | | |
| | Transporter, adenosine | 60 | | | | | | | | |
| | Transporter, dopamine | 52 | | | | | | | | |
| | Transporter, norepinephrine | 59 | | | | | | | | |
| | Vasopressin V1 | 69 | | | | | | | | |
| XTT-217 | Adenosine 2A | 61 | >10 | na | 12.6 | 10.2 | 9.7 | 9.2 | 14.1 | >10 |
| | Cannabinoid CB1 | 56 | | | | | | | | |

*Hepatocyte elimination half-life (min)
**Indicator of TL4 antagonism
***Ca channel L-type, phenylalkylamine
****Ca channel L-type, benzothiazepine

Example 11

The Experimental Autoimmune Encephalomyelitis (EAE) Model has been developed as a rat model of multiple sclerosis (Sloane, E. et al. *Brain Behav. Immun.* 2009, 23, 92-100). The model encompasses the injection of myelin oligodendrocyte glycoprotein (MOG) or similar glycoprotein to establish and antibody reaction that damages spinal nerve fibers leading to a progression of motor and sensory deficits. The rapid progression of deficits can be slowed by reduction of the MOG dose, enabling testing for pain responses prior to the development of hind limb paresis.

Reduced-dose MOG or saline (sham) was administered intradermally at the base of the tail. Mechanical allodynia pain testing was performed on hind left and right paws by application of Semmes-Weinstein ("von Frey") monofilaments calibrated for different bending forces for 8 seconds to determine the paw-withdrawal threshold. On day 15 post EAE induction, after reduction in the paw-withdrawal threshold (establishment of mechanical allodynia pain), subcutaneous injection of 15 mg/kg XT-203 or saline was administered three times/day for 15 days. Behavioral data were analyzed with two-way ANOVA. For all tests, statistical significance was set to $p<0.05$ (*).

Figure 16A:
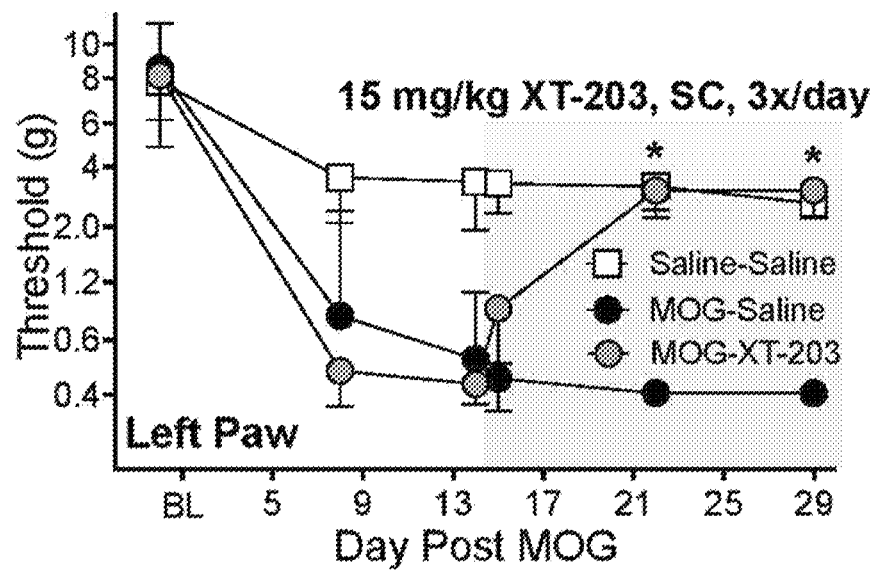
FIG. 16A shows a graph of the Experimental Autoimmune Encephalomyelitis (EAE) model from the left paw of a rat.
Figure 16B:
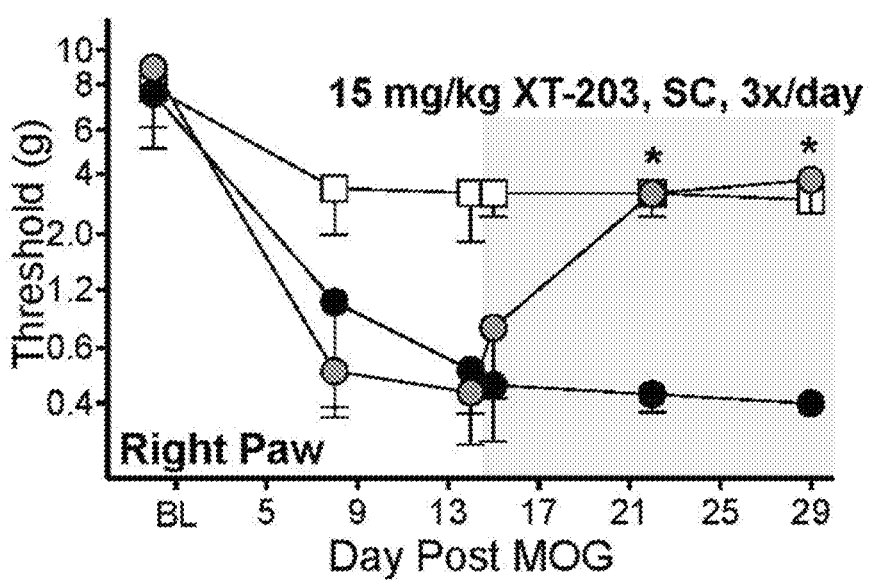
FIG. 16B shows a graph of the Experimental Autoimmune Encephalomyelitis (EAE) model from the right paw of a rat.

For both paws, XT-203 subcutaneous had no effect on the pain response in sham non-MOG rats (FIGS. 16A and 16B). Saline had no effect in the progression of pain responses in MOG-treated rats. XT-203 subcutaneous did reverse pain responses in MOG-treated rats, returning their pain responses to those observed in the sham rats.

It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. § 112, 6.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any one of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula IC, wherein the compound is the (+)-isomers of Formula IC or a pharmaceutically acceptable salt thereof:

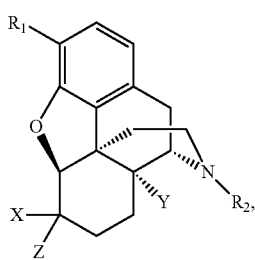

Formula IC wherein:

R₁ is selected from the group consisting of hydroxyl, alkoxy, and aryloxy;

R₂ is selected from the group consisting of hydrogen, alkyl, alkynyl, alkenyl, alkoxy, hydrocarbyl, substituted hydrocarbyl, cycloalkyl, alkylaryl, substituted alkylaryl

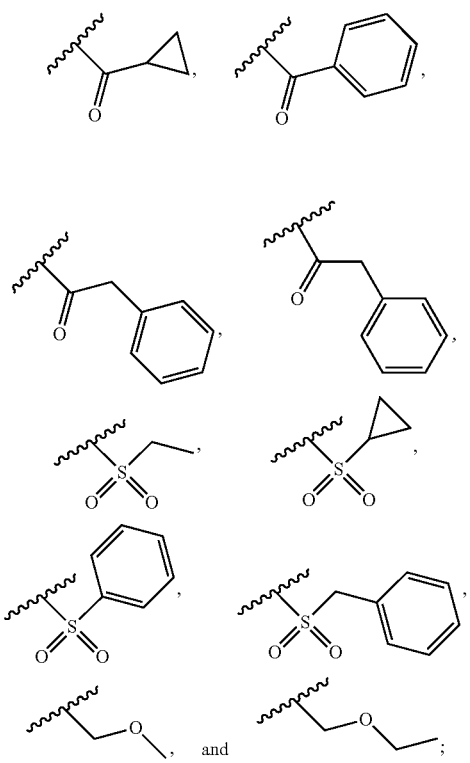

Y is selected from the group consisting of hydrogen and hydroxy;

X is fluorine; and

Z is hydrogen; provided that when R₁ is hydroxyl, R₂ is not cyclopropylmethyl.

2. The compound of claim 1, wherein Y is hydrogen.

3. The compound of claim 1, wherein Y is hydroxy.

4. The compound of claim 1, wherein R₁ is hydroxyl or methoxy.

5. The compound of claim 1, wherein R₂ is cyclopropylmethyl, propenyl, or phenethyl.

6. A compound of formula:

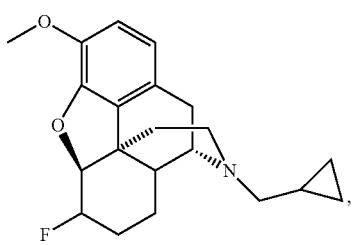

Formula VII or a pharmaceutically acceptable salt thereof.

7. The compound of claim 1, wherein wherein the compound is of the formula:

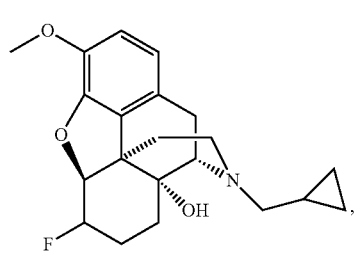

Formula IX or a pharmaceutically acceptable salt thereof.

8. A compound of Formula IC, wherein the compound is the (+)-isomer of Formula IC, or a pharmaceutically acceptable salt thereof:

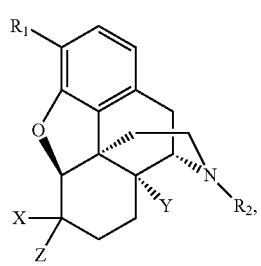

Formula IC wherein R₁ is methoxy, R₂ is cyclopropyl, Y is hydrogen, X is fluorine, and Z is hydrogen.

9. The compound of claim 1, wherein the (+)-isomer of Formula IC is of the formula:

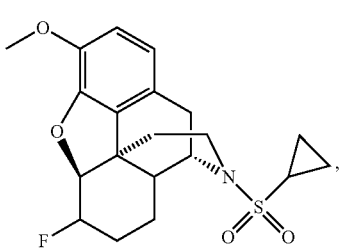

Formula XXXIII or a pharmaceutically acceptable salt thereof.

10. The compound of claim 1, wherein the compound of Formula IC is selected from the group consisting of:
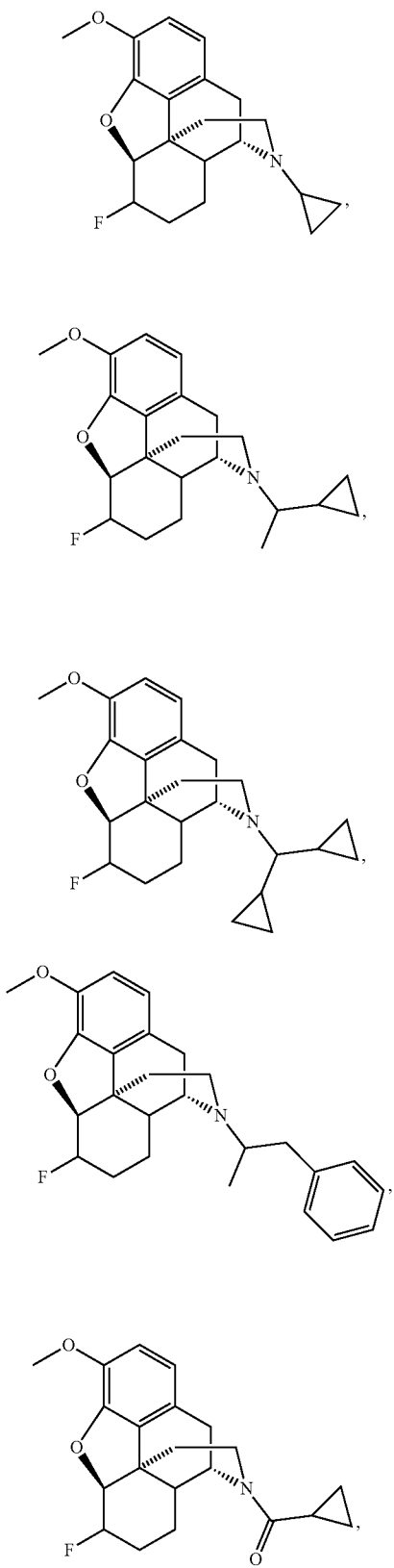
Formula XXII
Formula XXIII
Formula XXIV
Formula XXVII
Formula XXVIII
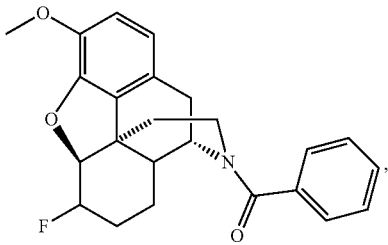
Formula XXIX
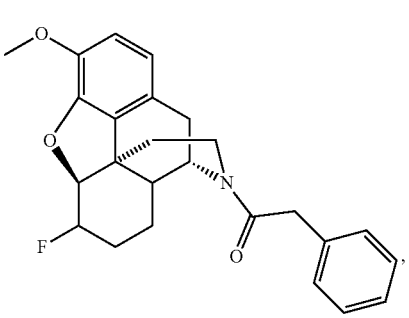
Formula XXX
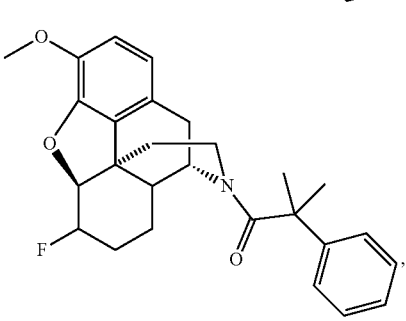
Formula XXXI
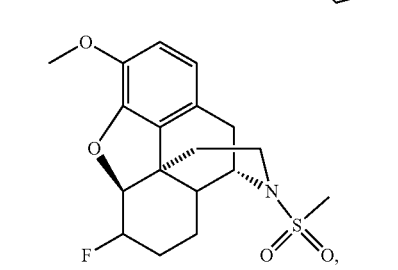
Formula XXXII
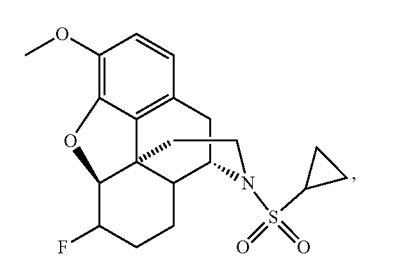
Formula XXXIII
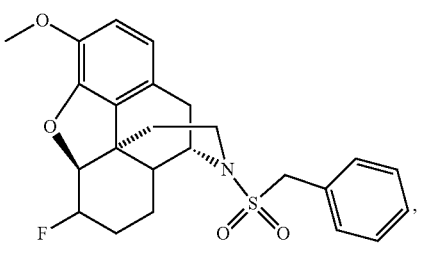
Formula XXXV
and pharmaceutically acceptable salts thereof.

11. A method for potentiating the analgesic effects of an opioid in a subject comprising administering to the subject an effective amount of the compound of claim 1.

12. A method for reducing the risk of developing an opioid dependency in a subject during opioid therapy, comprising the step of administering to the subject who is on opioid therapy an effective amount of the compound of claim 1.

13. A method for treating a subject with a clinical condition associated with Toll-like receptor (TLR) glial activation comprising the step of administering to the subject an effective amount of the compound of claim 1; wherein the clinical condition is acute nociceptive pain, neuropathic pain, pain associated with neurological diseases, pain associated with neuronal damage, pain caused by burns, pain caused by osteoarthritis, pain caused by chemotherapy, pain caused by trauma, acute and repetitive opioid analgesia, the reward effects of drug abuse, chronic pain, or other pain associated with opioid dependency.

14. A method for treating a subject suffering from or susceptible to neuropathic pain, the method comprising administering to the subject an effective amount of the compound of claim 1.

15. A method for treating a subject suffering from or susceptible to nociceptive pain, the method comprising administering to the subject an effective amount of the compound of claim 1.

16. The method of claim 14, wherein the neuropathic pain is due to a condition selected from the group consisting of spinal cord injury, multiple sclerosis, stroke, diabetes, sciatica, herpes zoster infection, HIV, neuralgia, nutritional deficiencies, toxins, tumors, immune mediated disorders, physical trauma to a nerve trunk, cancer, chemotherapy, radiation injury, invasive medical procedures, surgery, non-specific lower back pain, carpal tunnel syndrome, fibromyalgia, and a chronic inflammatory condition.

17. The method of claim 14, wherein the neuropathic pain is due to multiple sclerosis.

18. The method of claim 14, wherein the neuropathic pain is due to cancer.

19. The method of claim 14, wherein the neuropathic pain is due to chemotherapy.

20. The method of claim 13, wherein the Toll-like receptor is TLR-4.

21. The compound of claim 1, wherein R2 is hydrogen, methyl, ethyl, n-propyl, isopropyl, n-butyl, tert-butyl, sec-butyl, isobutyl, n-pentyl, neopentyl, tert-pentyl, isopentyl, sec-pentyl, 3-pentyl, sec-isopentyl, n-hexyl, hexyl, cyclopropylmethyl, dicyclopropylmethyl, 1-cyclopropylethyl, 2-propenyl, cyclohexyl, 1-phenylethyl, 1-methyl-2-phenylethyl, benzyl,

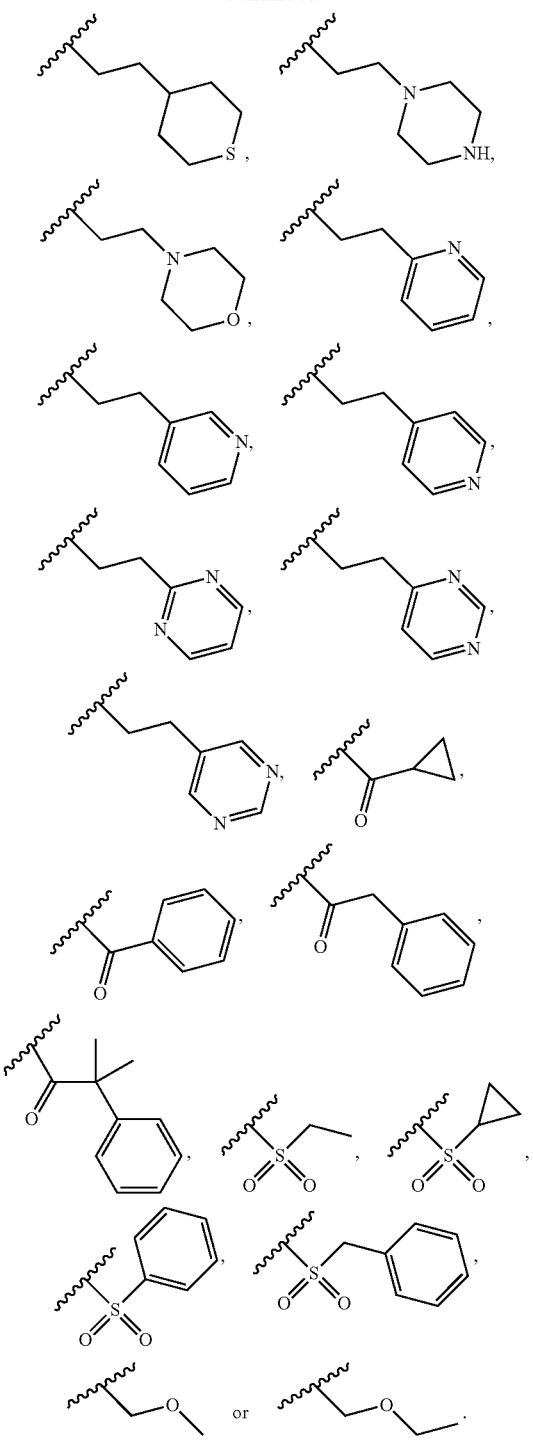

* * * * *